United States Patent
Elisseeff et al.

(10) Patent No.: US 11,458,227 B2
(45) Date of Patent: Oct. 4, 2022

(54) COMPOSITIONS AND METHODS FOR MODULATING WOUND HEALING AND REGENERATION

(71) Applicant: The Johns Hopkins University, Baltimore, MD (US)

(72) Inventors: Jennifer H. Elisseeff, Baltimore, MD (US); Kaitlyn Sadtler, Baltimore, MD (US); Drew M. Pardoll, Brookeville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/750,795

(22) PCT Filed: Aug. 5, 2016

(86) PCT No.: PCT/US2016/045720
§ 371 (c)(1),
(2) Date: Feb. 6, 2018

(87) PCT Pub. No.: WO2017/027353
PCT Pub. Date: Feb. 16, 2017

(65) Prior Publication Data
US 2019/0060524 A1 Feb. 28, 2019

Related U.S. Application Data

(60) Provisional application No. 62/202,537, filed on Aug. 7, 2015.

(51) Int. Cl.
*A61L 27/54* (2006.01)
*A61L 27/24* (2006.01)
*A61L 27/36* (2006.01)

(52) U.S. Cl.
CPC ............... *A61L 27/54* (2013.01); *A61L 27/24* (2013.01); *A61L 27/3633* (2013.01); *A61L 2300/25* (2013.01); *A61L 2300/256* (2013.01); *A61L 2300/412* (2013.01); *A61L 2300/426* (2013.01); *A61L 2430/34* (2013.01)

(58) Field of Classification Search
CPC ...... A61L 27/54; A61L 27/24; A61L 27/3633; A61L 2300/25; A61L 2300/256; A61L 2300/412; A61L 2300/426; A61L 2430/34
See application file for complete search history.

(56) References Cited

U.S. PATENT DOCUMENTS

| | | | | |
|---|---|---|---|---|
| 5,110,604 | A * | 5/1992 | Chu | A61K 38/39 128/DIG. 8 |
| 5,654,267 | A * | 8/1997 | Vuori | A61K 47/6435 424/85.2 |
| 2006/0177418 | A1* | 8/2006 | Braiman-Wiksman | A61K 31/22 424/85.1 |
| 2009/0202617 | A1 | 8/2009 | Ward et al. | |
| 2010/0254900 | A1* | 10/2010 | Campbell | A61L 27/18 424/1.65 |
| 2010/0303886 | A1 | 12/2010 | Janis | |
| 2012/0276202 | A1* | 11/2012 | Selim | A61K 35/30 424/484 |
| 2013/0323201 | A1 | 12/2013 | Wise et al. | |
| 2015/0139960 | A1 | 5/2015 | Tumey et al. | |

OTHER PUBLICATIONS

Worthington et al., Immunobiology, 217(12), pp. 1259-1265. (Year: 2012).*
Mohan et al., Indian J Med Res, 138(5), pp. 779-795. (Year: 2013).*
Boehler, et al. "Tissue engineering tools for modulation of the immune response", Biotechniques, Oct. 31, 2011 (Oct. 31, 2011), vol. 51, No. 4, pp. 1-20.
International Search Report/Written of International Application PCT/US2016/045720, dated Dec. 13, 2015.

* cited by examiner

*Primary Examiner* — Abigail Vanhorn
(74) *Attorney, Agent, or Firm* — Fox Rothschild LLP

(57) ABSTRACT

The present disclosure relates to compositions and methods for modulating wound healing and regeneration. More particularly, the present disclosure relates to immunomodulatory agents that promote wound healing and tissue regeneration, and that may be optionally used in combination with synthetic or biomaterial scaffolds.

8 Claims, 58 Drawing Sheets
Specification includes a Sequence Listing.

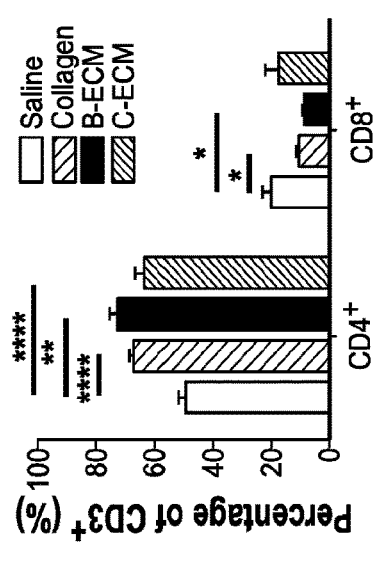
FIG. 1B
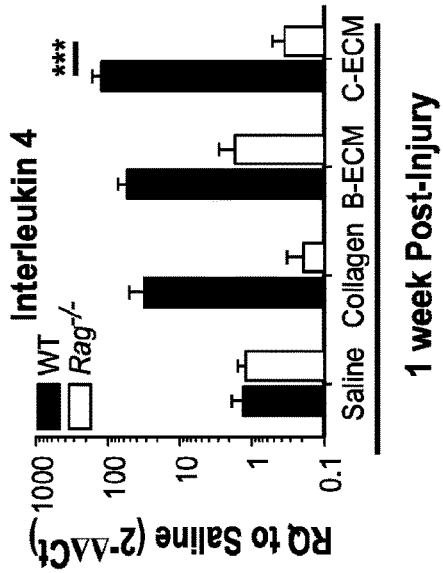
FIG. 1C
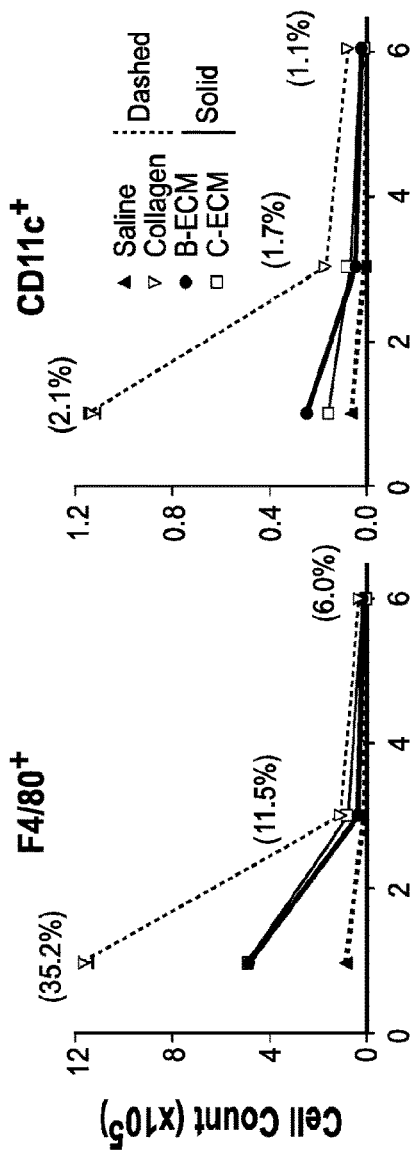
FIG. 1A
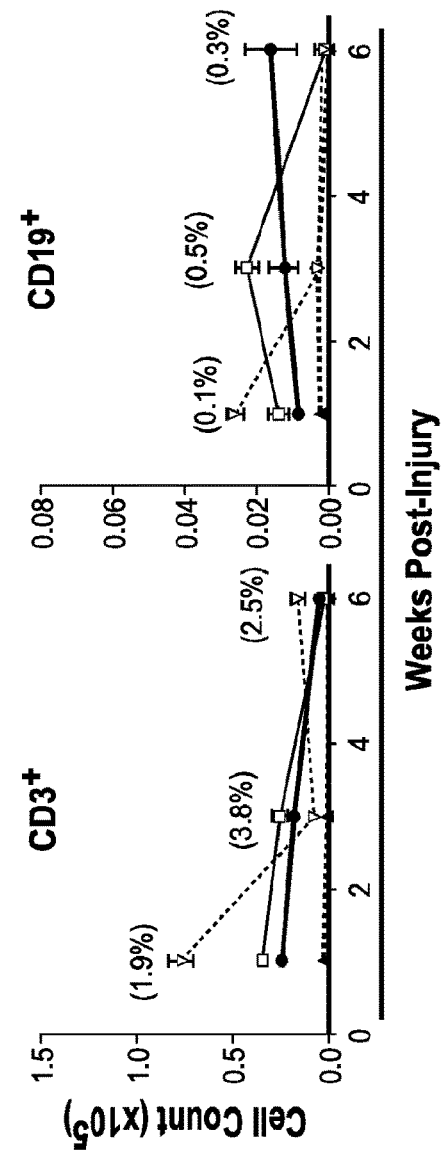

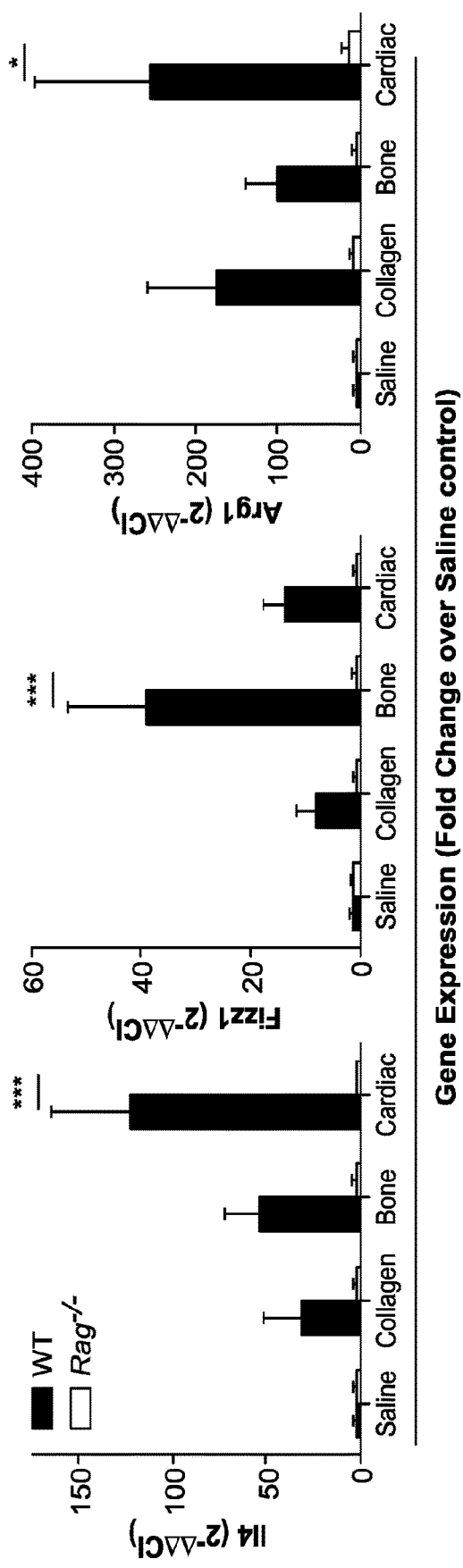

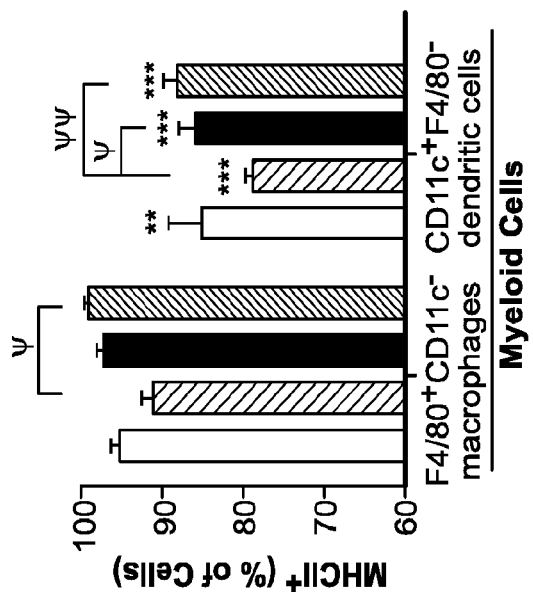
FIG. 6G
FIG. 6H
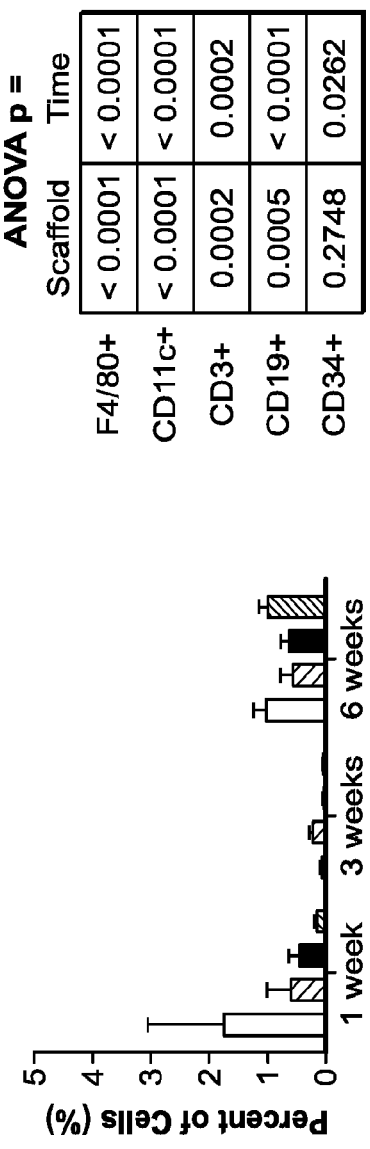

FIG. 7A
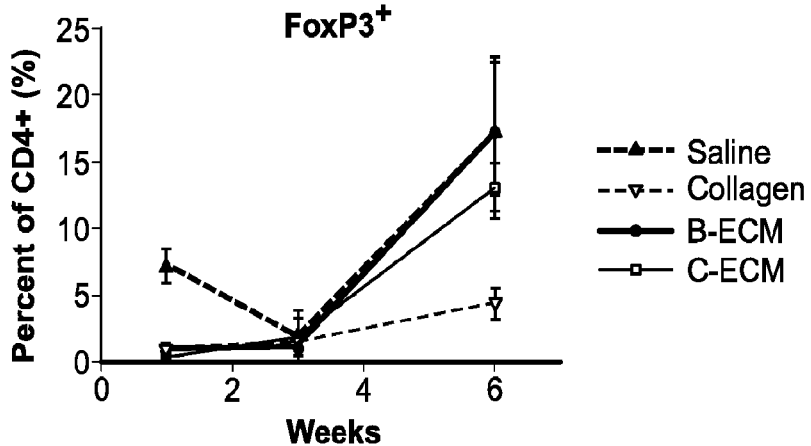
FIG. 7B
Scaffold 0.0185
Time < 0.0001
FIG. 7C
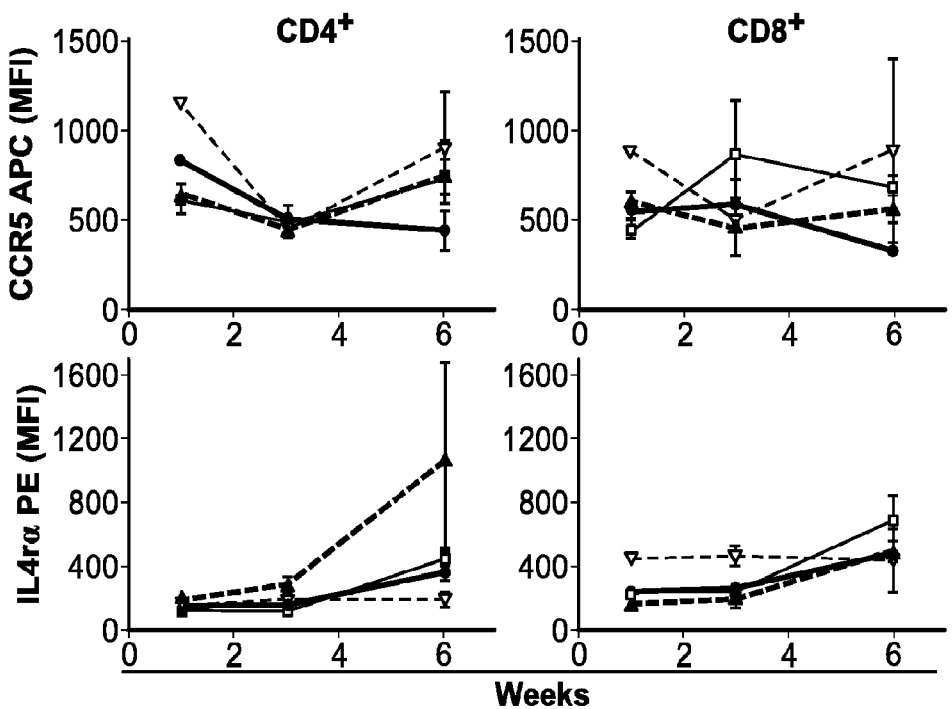
FIG. 7D
|  | CD4 | | CD8 | |
|---|---|---|---|---|
|  | CCR5 | IL4ra | CCR5 | IL4ra |
| Scaffold | 0.0567 | 0.0845 | 0.3208 | 0.1045 |
| Time | 0.0007 | 0.0093 | 0.9914 | 0.0001 |

FIG. 9
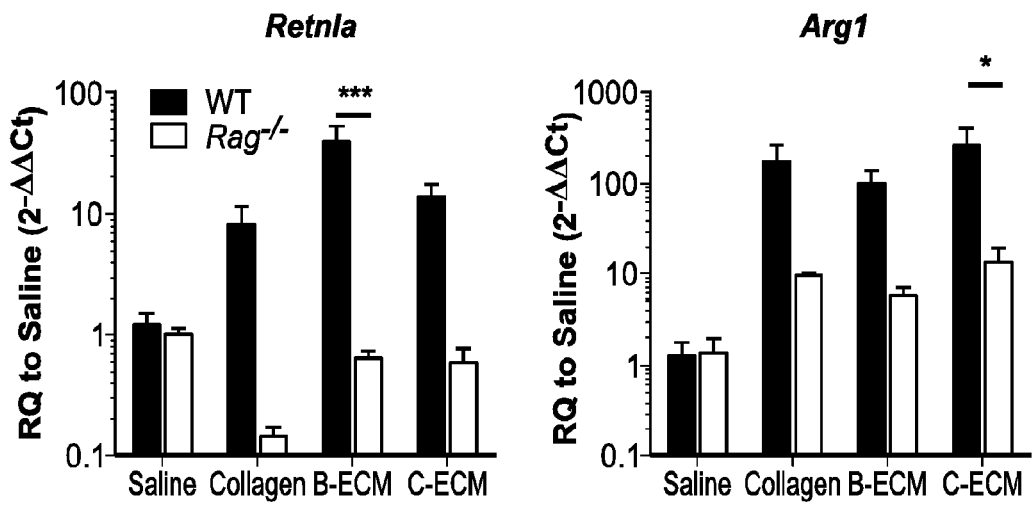
FIG. 10A
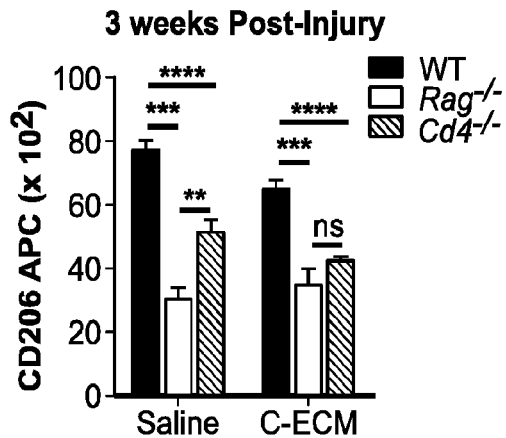
FIG. 10B
| ANOVA | | Genotype | Scaffold |
|---|---|---|---|
| 1wk | CD86 | 0.0476 | < 0.0001 |
| | CD206 | < 0.0001 | 0.0018 |
| 3wk | CD86 | < 0.0001 | < 0.0001 |
| | CD206 | < 0.0001 | < 0.0001 |

| ANOVA to Saline: | | 1wk | | 3wk | |
|---|---|---|---|---|---|
| | | CD86 | CD206 | CD86 | CD206 |
| WT | Collagen | ns | ns | ns | **** |
| | B-ECM | * | ns | ns | ns |
| | C-ECM | ** | ns | * | * |
| Rag-/- | Collagen | ns | **** | **** | **** |
| | B-ECM | ns | ns | ns | ns |
| | C-ECM | *** | * | ns | ns |

FIG. 11B Pre-Injection (d0)

FIG. 11C Day 11 Post-Injection (d11)

FIG. 13B-1

| GO_id | Term | # Of Genes | P-value | FDR | Bonferroni |
|---|---|---|---|---|---|
| GO:0048660 | regulation of smooth muscle cell proliferation | 9 | 4.04E-14 | 1.09E-11 | 5.44E-10 |
| GO:0051094 | positive regulation of developmental process | 16 | 1.59E-12 | 2.91E-10 | 2.14E-08 |
| GO:1903034 | regulation of response to wounding | 10 | 5.42E-11 | 6.23E-09 | 7.29E-07 |
| GO:0043771 | tissue remodeling | 7 | 1.38E-10 | 1.40E-03 | 1.86E-06 |
| GO:0050703 | regulation of developmental process | 18 | 1.49E-10 | 1.47E-03 | 2.00E-06 |
| GO:0032963 | collagen metabolic process | 5 | 2.37E-09 | 1.82E-07 | 3.19E-05 |
| GO:0045595 | regulation of cell differentiation | 14 | 1.07E-08 | 7.14E-07 | 1.44E-04 |
| GO:0030879 | mammary gland development | 6 | 1.56E-08 | 1.01E-06 | 2.10E-04 |
| GO:1903035 | positive regulation of response to wounding | 6 | 4.91E-08 | 2.90E-06 | 6.61E-04 |
| GO:2000177 | regulation of neural precursor cell proliferation | 5 | 2.07E-07 | 1.06E-06 | 2.79E-03 |
| GO:0022603 | regulation of anatomical structure morphogenesis | 10 | 2.39E-07 | 1.20E-05 | 3.21E-03 |
| GO:0045765 | regulation of angiogenesis | 6 | 4.52E-07 | 2.12E-05 | 6.07E-03 |
| GO:0022612 | gland morphogenesis | 5 | 6.48E-07 | 2.90E-05 | 8.71E-03 |
| GO:1901342 | regulation of vasculature development | 6 | 7.02E-07 | 3.11E-05 | 9.44E-03 |
| GO:0048856 | anatomical structure development | 19 | 7.64E-07 | 3.34E-05 | 1.03E-02 |
| GO:0048732 | gland development | 7 | 8.30E-07 | 3.60E-05 | 1.12E-02 |
| GO:0061180 | mammary gland epithelium development | 4 | 1.65E-06 | 6.38E-05 | 2.22E-02 |
| GO:0032502 | developmental process | 19 | 1.95E-06 | 7.44E-05 | 2.62E-02 |
| GO:0060688 | regulation of morphogenesis of a branching structure | 4 | 2.04E-06 | 7.68E-05 | 2.74E-02 |
| GO:0050679 | positive regulation of epithelial cell proliferation | 5 | 3.07E-06 | 1.11E-04 | 4.13E-02 |
| GO:1901514 | regulation of neuron death | 6 | 3.08E-06 | 1.11E-04 | 4.14E-02 |
| GO:0030674 | collagen catabolic process | 3 | 5.09E-06 | 1.75E-04 | 6.84E-02 |
| GO:0060429 | epithelium development | 9 | 5.99E-06 | 2.01E-04 | 8.05E-02 |
| GO:0007275 | multicellular organismal development | 17 | 6.26E-06 | 2.09E-04 | 8.41E-02 |
| GO:0010634 | positive regulation of epithelial cell migration | 4 | 1.01E-05 | 3.18E-04 | 1.36E-01 |
| GO:0010574 | regulation of vascular endothelial growth factor production | 3 | 1.08E-05 | 3.36E-04 | 1.45E-01 |

FIG. 13B-2

| GO ID | Description | | | |
|---|---|---|---|---|
| GO:1902692 | regulation of neuroblast proliferation | 3 | 2.13E-05 | 6.16E-04 | 2.87E-01 |
| GO:0001974 | blood vessel remodeling | 3 | 2.53E-05 | 7.17E-04 | 3.40E-01 |
| GO:0045766 | positive regulation of angiogenesis | 4 | 2.82E-05 | 7.89E-04 | 3.79E-01 |
| GO:0003006 | developmental process involved in reproduction | 7 | 3.41E-05 | 9.31E-04 | 4.59E-01 |
| GO:0009887 | organ morphogenesis | 8 | 3.44E-05 | 9.31E-04 | 4.62E-01 |
| GO:1904018 | positive regulation of vasculature development | 4 | 3.68E-05 | 9.86E-04 | 4.94E-01 |
| GO:0048513 | organ development | 13 | 4.44E-05 | 1.17E-03 | 5.97E-01 |
| GO:0090594 | inflammatory response to wounding | 2 | 4.84E-05 | 1.25E-03 | 6.51E-01 |
| GO:0002245 | wound healing involved in inflammatory response | 2 | 4.84E-05 | 1.25E-03 | 6.51E-01 |
| GO:0030855 | epithelial cell differentiation | 6 | 5.14E-05 | 1.31E-03 | 6.91E-01 |
| GO:0010660 | regulation of muscle cell apoptotic process | 3 | 5.92E-05 | 1.50E-00 | 7.96E-01 |
| GO:0034393 | positive regulation of smooth muscle cell apoptotic process | 2 | 6.45E-05 | 1.62E-03 | 8.67E-01 |
| GO:2000179 | positive regulation of neural precursor cell proliferation | 3 | 6.67E-05 | 1.66E-03 | 8.97E-01 |
| GO:0010632 | regulation of epithelial cell migration | 4 | 7.21E-05 | 1.79E-03 | 9.69E-01 |
| GO:0060426 | lung vasculature development | 2 | 8.28E-05 | 2.01E-03 | 1.00E+00 |
| GO:0009653 | anatomical structure morphogenesis | 11 | 8.68E-05 | 2.10E-03 | 1.00E+00 |
| GO:0031099 | regeneration | 3 | 1.20E-04 | 2.77E-03 | 1.00E+00 |
| GO:0030198 | extracellular matrix organization | 4 | 1.62E-04 | 3.60E-03 | 1.00E+00 |
| GO:0043062 | extracellular structure organization | 4 | 1.66E-04 | 3.67E-03 | 1.00E+00 |
| GO:0060644 | mammary gland epithelial cell differentiation | 2 | 1.79E-04 | 3.87E-03 | 1.00E+00 |
| GO:0061138 | morphogenesis of a branching epithelium | 4 | 1.84E-04 | 3.98E-03 | 1.00E+00 |
| GO:0033598 | mammary gland epithelial cell proliferation | 2 | 2.08E-04 | 4.42E-03 | 1.00E+00 |
| GO:0001763 | morphogenesis of a branching structure | 4 | 2.21E-04 | 4.63E-03 | 1.00E+00 |
| GO:0010661 | positive regulation of muscle cell apoptotic process | 2 | 2.40E-04 | 4.98E-03 | 1.00E+00 |
| GO:0048608 | reproductive structure development | 5 | 2.48E-04 | 5.13E-03 | 1.00E+00 |
| GO:0009888 | tissue development | 9 | 2.57E-04 | 5.30E-03 | 1.00E+00 |
| GO:0061458 | reproductive system development | 5 | 2.64E-04 | 5.40E-03 | 1.00E+00 |

FIG. 13B-3

| | | | |
|---|---|---|---|
| GO:0031100 | organ regeneration | 2 | 2.74E-04 | 5.55E-03 | 1.00E+00 |
| GO:0050673 | epithelial cell proliferation | 3 | 2.95E-04 | 5.92E-03 | 1.00E+00 |
| GO:0001936 | regulation of endothelial cell proliferation | 3 | 3.27E-04 | 6.43E-03 | 1.00E+00 |
| GO:0042060 | wound healing | 4 | 9.95E-04 | 7.61E-03 | 1.00E+00 |
| GO:0001501 | skeletal system development | 5 | 4.72E-04 | 8.90E-03 | 1.00E+00 |
| GO:0048568 | embryonic organ development | 5 | 5.03E-04 | 9.42E-03 | 1.00E+00 |
| GO:0001892 | embryonic placenta development | 3 | 5.07E-04 | 9.42E-03 | 1.00E+00 |
| GO:0060749 | mammary gland alveolus development | 2 | 5.25E-04 | 9.60E-03 | 1.00E+00 |
| GO:0061377 | mammary gland lobule development | 2 | 5.25E-04 | 9.60E-03 | 1.00E+00 |
| GO:0002009 | morphogenesis of an epithelium | 5 | 5.30E-04 | 9.68E-03 | 1.00E+00 |

| GO_id | Term | Number Of Genes | p-value | p-value bonferroni |
|---|---|---|---|---|
| GO:0048660 | regulation of smooth muscle cell proliferation | 7 | 2.87E-11 | 1.61E-08 |
| GO:0048661 | positive regulation of smooth muscle cell proliferation | 6 | 1.36E-10 | 6.07E-08 |
| GO:0048771 | tissue remodeling | 6 | 1.54E-09 | 4.22E-07 |
| GO:0032963 | collagen metabolic process | 4 | 9.16E-08 | 1.47E-05 |
| GO:0045597 | positive regulation of cell differentiation | 8 | 2.89E-06 | 2.32E-04 |
| GO:0060429 | epithelium development | 8 | 6.25E-06 | 4.35E-04 |
| GO:1903034 | regulation of response to wounding | 5 | 4.11E-05 | 2.19E-03 |
| GO:0045765 | regulation of angiogenesis | 4 | 7.52E-05 | 3.64E-03 |
| GO:1901342 | regulation of vasculature development | 4 | 1.01E-04 | 4.54E-03 |
| GO:0071542 | dopaminergic neuron differentiation | 2 | 1.62E-04 | 6.55E-03 |
| GO:0009888 | tissue development | 8 | 1.94E-04 | 7.57E-03 |
| GO:0045595 | regulation of cell differentiation | 8 | 1.94E-04 | 7.57E-03 |
| GO:0045766 | positive regulation of angiogenesis | 3 | 3.32E-04 | 1.17E-02 |
| GO:0002052 | positive regulation of neuroblast proliferation | 2 | 4.03E-04 | 1.39E-02 |
| GO:1903036 | positive regulation of response to wounding | 3 | 5.10E-04 | 1.65E-02 |
| GO:0043524 | negative regulation of neuron apoptotic process | 3 | 7.11E-04 | 2.20E-02 |
| GO:0014911 | positive regulation of smooth muscle cell migration | 2 | 7.49E-04 | 2.29E-02 |
| GO:1902692 | regulation of neuroblast proliferation | 2 | 7.93E-04 | 2.42E-02 |
| GO:0001974 | blood vessel remodeling | 2 | 8.87E-04 | 2.69E-02 |
| GO:0048856 | anatomical structure development | 12 | 9.40E-04 | 2.78E-02 |
| GO:0051146 | striated muscle cell differentiation | 3 | 1.14E-03 | 3.30E-02 |
| GO:0001701 | in utero embryonic development | 4 | 1.33E-03 | 3.78E-02 |
| GO:0061138 | morphogenesis of a branching epithelium | 3 | 1.35E-03 | 3.83E-02 |
| GO:0045600 | positive regulation of fat cell differentiation | 2 | 1.43E-03 | 4.01E-02 |
| GO:0001763 | morphogenesis of a branching structure | 3 | 1.55E-03 | 4.29E-02 |
| GO:0010660 | regulation of muscle cell apoptotic process | 2 | 1.55E-03 | 4.29E-02 |
| GO:0032502 | developmental process | 12 | 1.62E-03 | 4.41E-02 |
| GO:0048568 | embryonic organ development | 4 | 1.63E-03 | 4.43E-02 |
| GO:0002009 | morphogenesis of an epithelium | 4 | 1.70E-03 | 4.60E-02 |
| GO:0051962 | positive regulation of nervous system development | 4 | 1.81E-03 | 4.82E-02 |
| GO:0014910 | regulation of smooth muscle cell migration | 2 | 1.81E-03 | 4.82E-02 |
| GO:0060249 | anatomical structure homeostasis | 3 | 1.87E-03 | 4.95E-02 |

FIG. 13F smooth positive process angiogenesis developmental structure migration response morphogenesis remodeling differentiation embryonic fat striated organ metabolic dopaminorgic neuroblast branching vessel neuron collagen system muscle negative homeostasis blood epithelium nervous tissue anatomical apoptotic wounding development vasculature utero proliferation cell regulation

FIG. 18A

| Gene | Saline vs | | |
|---|---|---|---|
| | B-ECM | C-ECM | Collagen |
| Cd1d1 | 0.029 | 0.029 | 0.200 |
| Cd4 | 0.343 | 0.343 | 0.029 |
| Cd8a | 0.029 | 0.029 | 0.029 |
| Ifng | 0.029 | 0.029 | 0.029 |
| Tbx21 | 0.029 | 0.029 | 0.029 |
| Gata3 | 0.886 | 0.343 | 0.029 |
| Il4 | 0.029 | 0.029 | 0.029 |
| Il5 | 0.686 | 0.886 | 0.686 |
| Il17a | 0.200 | 0.486 | 0.029 |
| Il21 | 1.000 | 0.886 | 0.029 |
| Il22;Iltifb | 0.486 | 0.486 | 0.343 |
| Irf4 | 0.029 | 0.029 | 0.486 |
| Rorc | 0.029 | 0.029 | 0.486 |
| Foxp3 | 0.343 | 0.886 | 0.029 |
| Il10 | 0.029 | 0.029 | 0.029 |
| Il2ra | 0.486 | 0.886 | 0.029 |
| Tgfb1 | 0.029 | 0.029 | 1.000 |
| Cd28 | 0.029 | 0.029 | 0.029 |
| Cd40lg | 0.029 | 0.029 | 0.029 |
| Ctla4 | 0.200 | 0.886 | 0.029 |
| Fasl | 0.029 | 0.029 | 0.029 |
| Pdcd1 | 0.029 | 0.029 | 0.029 |
| Tnfrsf9 | 1.000 | 0.886 | 0.200 |
| Cxcl12 | 0.343 | 0.486 | 0.686 |
| Cxcr4 | 0.057 | 0.029 | 0.057 |
| Il15 | 1.000 | 0.686 | 0.114 |
| Il18 | 0.886 | 0.686 | 0.886 |
| Tnf | 1.000 | 0.200 | 0.029 |
| Il2 | 0.029 | 0.114 | 0.343 |
| Socs5 | 0.057 | 0.029 | 0.029 |
| Bad | 0.343 | 0.886 | 0.057 |
| Cblb | 0.029 | 0.029 | 0.029 |
| Ccnd3 | 0.686 | 0.200 | 0.029 |
| Cd27 | 0.114 | 0.057 | 0.686 |
| Glmn | 0.029 | 0.029 | 0.029 |
| Icos | 0.029 | 0.029 | 0.486 |
| Jag2 | 0.114 | 0.057 | 0.029 |
| Sit1 | 0.029 | 0.029 | 0.029 |
| Sla2 | 0.200 | 0.114 | 0.486 |
| Spp1 | 0.057 | 0.029 | 0.029 |
| Tnfsf14 | 0.029 | 0.029 | 0.114 |
| Tslp | 0.029 | 0.309 | 0.309 |

FIG. 18B

| Gene Group | Saline vs | | |
|---|---|---|---|
| | B-ECM | C-ECM | Collagen |
| NKT | 0.024 | 0.025 | 0.208 |
| Th | 0.328 | 0.35 | 0.023 |
| CTL | 0.024 | 0.025 | 0.023 |
| Th1 | 0.024 | 0.025 | 0.023 |
| Th2 | 0.087 | 0.079 | 0.057 |
| Th17 | 0.12 | 0.12 | 0.112 |
| Treg | 0.75 | 0.085 | 0.048 |
| T cell act | 0.076 | 0.078 | 0.052 |
| Inflamm | 0.251 | 0.152 | 0.144 |
| IL2 | 0.059 | 0.053 | 0.045 |

FIG. 19A

| | WT | | | Rag$^{-/-}$ | | |
|---|---|---|---|---|---|---|
| | Saline vs | | | Saline vs | | |
| Gene | B-ECM | C-ECM | Collagen | B-ECM | C-ECM | Collagen |
| Ccr2 | 1.000 | 0.343 | 0.057 | 0.686 | 0.029 | 0.343 |
| Csf1r | 0.029 | 0.114 | 0.886 | 0.029 | 0.114 | 0.057 |
| Csf2rb | 0.200 | 0.029 | 0.029 | 0.114 | 0.686 | 0.029 |
| Emr1 | 0.057 | 0.029 | 0.886 | 0.343 | 1.000 | 0.886 |
| Arg1 | 0.029 | 0.029 | 0.029 | 0.029 | 0.114 | 0.029 |
| Cebpb | 0.114 | 0.029 | 0.029 | 0.029 | 0.057 | 0.029 |
| Igf1 | 0.029 | 0.029 | 1.000 | 0.343 | 0.029 | 0.343 |
| Il10 | 0.029 | 0.029 | 0.029 | 0.029 | 0.200 | 0.029 |
| Il10ra | 0.029 | 0.029 | 0.686 | 0.114 | 0.686 | 0.057 |
| Il12a | 0.029 | 0.029 | 0.029 | 1.000 | 1.000 | 0.343 |
| Il12b | 0.114 | 0.486 | 0.343 | 0.029 | 0.114 | 1.000 |
| Il1r1 | 0.057 | 0.029 | 0.029 | 0.343 | 0.343 | 0.029 |
| Il4ra | 0.200 | 0.886 | 0.029 | 0.886 | 0.486 | 0.029 |
| Mmp9 | 0.029 | 0.029 | 0.686 | 0.686 | 0.114 | 0.886 |
| Retnla | 0.029 | 0.029 | 0.114 | 0.029 | 0.029 | 0.057 |
| Stat3 | 0.029 | 0.029 | 0.200 | 0.029 | 0.114 | 0.029 |
| Stat6 | 0.343 | 0.114 | 0.057 | 0.029 | 0.343 | 0.029 |
| Tgfb1 | 1.000 | 0.057 | 1.000 | 0.886 | 0.486 | 0.114 |
| Timp1 | 0.029 | 0.029 | 0.029 | 0.029 | 0.486 | 0.343 |
| Vegfa | 0.486 | 0.343 | 0.057 | 0.029 | 0.029 | 0.029 |
| Ccl5 | 0.029 | 0.029 | 0.029 | 0.114 | 0.114 | 0.200 |
| Cybb | 0.029 | 0.029 | 0.029 | 0.029 | 0.200 | 0.029 |
| Ebi3 | 0.686 | 0.029 | 0.029 | 0.029 | 0.486 | 0.029 |
| H2-Ab1 | 1.000 | 0.200 | 0.200 | 1.000 | 0.486 | 0.886 |
| Hif1a | 0.886 | 0.057 | 0.114 | 0.029 | 1.000 | 0.486 |
| Ido1 | 1.000 | 0.686 | 0.029 | 0.029 | 0.343 | 0.029 |
| Ifngr1 | 0.486 | 0.686 | 1.000 | 0.886 | 0.114 | 0.029 |
| Il1b | 0.029 | 0.057 | 0.029 | 0.686 | 0.029 | 0.114 |
| Il23a | 0.029 | 0.029 | 0.029 | 0.029 | 0.029 | 0.057 |
| Il6 | 0.486 | 0.114 | 0.686 | 0.029 | 0.029 | 0.029 |
| Myd88 | 0.686 | 0.029 | 0.029 | 0.686 | 0.057 | 0.029 |
| Nos2 | 0.029 | 0.029 | 0.029 | 0.029 | 0.343 | 0.200 |
| Ptgs2 | 0.057 | 0.114 | 0.029 | 0.029 | 0.057 | 0.029 |
| Stat1 | 0.029 | 0.114 | 0.886 | 0.029 | 0.057 | 0.029 |
| Tnf | 0.886 | 0.057 | 0.486 | 0.686 | 0.029 | 0.029 |
| Casp1 | 0.029 | 0.029 | 0.029 | 0.029 | 0.029 | 0.029 |
| Cd274 | 0.029 | 0.029 | 0.029 | 0.343 | 0.057 | 0.029 |
| Ctsk | 0.029 | 0.029 | 0.029 | 0.057 | 0.057 | 0.486 |
| Il17ra | 0.486 | 0.029 | 0.029 | 0.029 | 0.029 | 0.200 |
| Il23r | 0.686 | 0.343 | 0.343 | 0.029 | 0.029 | 0.029 |
| Mmp16 | 0.029 | 0.029 | 0.029 | 0.029 | 0.057 | 0.029 |
| S100a8 | 0.114 | 0.029 | 0.029 | 0.029 | 0.200 | 0.029 |

FIG. 19B

| Gene | WT vs Rag⁻/⁻ | | |
|---|---|---|---|
| | B-ECM | C-ECM | Collagen |
| Ccr2 | 0.71 | 0.843 | 0.002 |
| Csf1r | 0.991 | 0.111 | <0.001 |
| Csf2rb | 0.023 | 0.004 | <0.001 |
| Arg1 | <0.001 | <0.001 | <0.001 |
| Cebpb | 0.008 | <0.001 | <0.001 |
| Igf1 | 0.007 | <0.001 | 0.724 |
| Il10 | 0.004 | <0.001 | <0.001 |
| Il12a | 0.021 | 0.12 | 0.568 |
| Il12b | 0.413 | 0.234 | 0.032 |
| Il1r1 | 0.237 | 0.393 | <0.001 |
| Il4ra | 0.131 | 0.022 | <0.001 |
| Mmp9 | 0.002 | 0.029 | 0.435 |
| Retnla | 0.001 | <0.001 | 0.002 |
| Stat6 | 0.289 | 0.051 | 0.008 |
| Tgfb1 | 0.261 | 0.979 | 0.003 |
| Timp1 | <0.001 | <0.001 | <0.001 |
| Vegfa | 0.011 | 0.006 | <0.001 |
| Ccl5 | <0.001 | <0.001 | <0.001 |
| Cybb | 0.021 | 0.004 | 0.005 |
| Ebi3 | 0.142 | 0.008 | <0.001 |
| H2-Ab1 | 0.115 | 0.003 | <0.001 |
| Hif1a | 0.071 | 0.211 | 0.003 |
| Ifngr1 | 0.413 | 0.028 | <0.001 |
| Il1b | 0.051 | 0.276 | <0.001 |
| Il23a | 0.06 | 0.023 | 0.119 |
| Myd88 | 0.021 | <0.001 | <0.001 |
| Nos2 | 0.039 | <0.001 | 0.08 |
| Stat1 | 0.002 | 0.787 | <0.001 |
| Tnf | 0.336 | 0.033 | 0.022 |
| Casp1 | <0.001 | 0.007 | <0.001 |
| Cd274 | <0.001 | <0.001 | 0.007 |
| Ctsk | <0.001 | <0.001 | <0.001 |
| Il17ra | 0.775 | 0.022 | <0.001 |
| Mmp16 | 0.063 | 0.748 | <0.001 |
| S100a8 | 0.177 | 0.042 | 0.358 |

FIG. 19C

| Gene | WT Saline vs | | | Rag⁻/⁻ Saline vs | |
|---|---|---|---|---|---|
| | Bone | Cardiac | Collagen | Bone | Cardiac |
| Ccr2 | 1.000 | 0.343 | 0.057 | 0.686 | 0.029 |
| Csf1r | 0.029 | 0.114 | 0.886 | 0.029 | 0.029 |
| Csf2rb | 0.200 | 0.029 | 0.029 | 0.343 | 0.057 |
| Emr1 | 0.057 | 0.029 | 0.886 | 0.029 | 0.029 |
| Arg1 | 0.029 | 0.029 | 0.029 | 0.114 | 0.114 |
| Cebpb | 0.114 | 0.029 | 0.029 | 0.057 | 0.029 |
| Igf1 | 0.029 | 0.029 | 1.000 | 0.114 | 0.029 |
| Il10 | 0.029 | 0.029 | 0.029 | 0.686 | 0.343 |
| Il10ra | 0.029 | 0.029 | 0.686 | 0.029 | 0.029 |
| Il12a | 0.029 | 0.029 | 0.029 | 0.343 | 0.886 |
| Il12b | 0.114 | 0.486 | 0.343 | 1.000 | 0.486 |
| Il1r1 | 0.057 | 0.029 | 0.029 | 0.886 | 0.114 |
| Il4ra | 0.200 | 0.886 | 0.029 | 0.029 | 0.029 |
| Mmp9 | 0.029 | 0.029 | 0.686 | 0.114 | 0.486 |
| Retnla | 0.029 | 0.029 | 0.114 | 0.029 | 0.343 |
| Stat3 | 0.029 | 0.029 | 0.200 | 0.029 | 0.029 |
| Stat6 | 0.343 | 0.114 | 0.057 | 0.057 | 0.029 |
| Tgfb1 | 1.000 | 0.057 | 1.000 | 0.029 | 0.029 |
| Timp1 | 0.029 | 0.029 | 0.029 | 0.343 | 0.114 |
| Vegfa | 0.486 | 0.343 | 0.057 | 0.029 | 0.114 |
| Ccl5 | 0.029 | 0.029 | 0.029 | 0.343 | 0.200 |
| Cybb | 0.029 | 0.029 | 0.029 | 0.029 | 0.029 |
| Ebi3 | 0.686 | 0.029 | 0.029 | 0.200 | 0.200 |
| H2-Ab1 | 1.000 | 0.200 | 0.200 | 0.029 | 0.029 |
| Hif1a | 0.886 | 0.057 | 0.114 | 0.114 | 0.029 |
| Ido1 | 1.000 | 0.686 | 0.029 | 0.686 | 0.486 |
| Ifngr1 | 0.486 | 0.686 | 1.000 | 0.057 | 0.029 |
| Il1b | 0.029 | 0.057 | 0.029 | 1.000 | 1.000 |
| Il23a | 0.029 | 0.029 | 0.029 | 1.000 | 0.486 |
| Il6 | 0.486 | 0.114 | 0.686 | 0.343 | 0.886 |
| Myd88 | 0.686 | 0.029 | 0.029 | 0.029 | 0.029 |
| Nos2 | 0.029 | 0.029 | 0.029 | 0.114 | 1.000 |
| Ptgs2 | 0.057 | 0.114 | 0.029 | 1.000 | 0.486 |
| Stat1 | 0.029 | 0.114 | 0.886 | 0.343 | 0.029 |
| Tnf | 0.886 | 0.057 | 0.486 | 0.343 | 0.343 |
| Casp1 | 0.029 | 0.029 | 0.029 | 0.029 | 0.029 |
| Cd274 | 0.029 | 0.029 | 0.029 | 0.886 | 0.886 |
| Ctsk | 0.029 | 0.029 | 0.029 | 0.486 | 0.114 |
| Il17ra | 0.486 | 0.029 | 0.029 | 0.029 | 0.029 |
| Il23r | 0.686 | 0.343 | 0.343 | 0.686 | 0.686 |
| Mmp16 | 0.029 | 0.029 | 0.029 | 0.114 | 0.029 |
| S100a8 | 0.114 | 0.029 | 0.029 | 0.886 | 0.114 |

FIG. 19D

| | WT vs Rag⁻/⁻ | |
|---|---|---|
| Gene | Bone | Cardiac |
| Csf2rb | 0.037 | 0.009 |
| Arg1 | <0.001 | <0.001 |
| Cebpb | 0.02 | <0.001 |
| Igf1 | <0.001 | <0.001 |
| Il10 | 0.002 | <0.001 |
| Il12a | 0.033 | 0.149 |
| Il4ra | 0.128 | 0..022 |
| Mmp9 | 0.002 | 0.03 |
| Retnla | <0.001 | <0.001 |
| Stat6 | 0.181 | 0.017 |
| Timp1 | <0.001 | <0.001 |
| Vegfa | 0.015 | 0.009 |
| Ccl5 | 0.002 | <0.001 |
| Cybb | 0.019 | 0.004 |
| Ebi3 | 0.176 | 0.016 |
| H2-Ab1 | 0.145 | 0.007 |
| Hif1a | 0.025 | 0.113 |
| Ifngr1 | 0.284 | 0.006 |
| Il23a | 0.059 | 0.023 |
| Myd88 | 0.018 | <0.001 |
| Nos2 | 0.039 | <0.001 |
| Stat1 | 0.004 | 0.796 |
| Casp1 | <0.001 | 0.007 |
| Cd274 | 0.002 | <0.001 |
| Ctsk | <0.001 | <0.001 |
| Il17ra | 0.744 | 0.012 |
| S100a8 | 0.181 | 0.045 |

# COMPOSITIONS AND METHODS FOR MODULATING WOUND HEALING AND REGENERATION

RELATED APPLICATIONS

This application is a National Phase application filed under 35 U.S.C. § 371 of PCT International Patent Application No. PCT/US2016/045720, with an International Filing Date of Aug. 5, 2016, which claims the benefit of priority under 35 U.S.C. § 119(e) to U.S. Provisional Application No. 62/202,537, filed on Aug. 7, 2015 entitled, "Compositions and methods for modulating wound healing and regeneration", which are incorporated herein by reference in their entirety.

FEDERALLY SPONSORED RESEARCH

This work was funded by the Maryland Stem Cell Research Fund (MSCRF) #113345 and the Jules Stein Professorship from the RPB Foundation.

SEQUENCE LISTING

The instant application contains a Sequence Listing which has been submitted electronically in ASCII format and is hereby incorporated by reference in its entirety. Said ASCII copy, created on Sep. 7, 2016, is named 048317-502N01US_SL.txt and is 5,336 bytes in size.

FIELD OF THE DISCLOSURE

The present disclosure relates to compositions and methods for modulating wound healing and regeneration. More particularly, the present disclosure relates to biomaterial scaffolds that may promote and expedite wound healing and regeneration.

BACKGROUND OF THE DISCLOSURE

Wounds are external or internal injuries caused by, for example, mechanical, chemical, thermal, or pathogenic means that result in the physical disruption of tissue integrity. For example, a wound may be a type of bodily injury in which the epidermis is torn, cut, or punctured.

Wound healing (e.g., the restoration of tissue integrity) is orchestrated by various growth factors and cytokines that regulate cell growth, cell migration, cell differentiation, and cell proliferation, and is generally sub-divided into three broad phases: inflammation, proliferation, and maturation. Numerous factors are involved in the complex process of wound healing following injury, and cytokines are considered to play a key role in the regulation of the entire process.

Wounds may be categorized as acute (e.g., fast healing) or chronic. Chronic wounds are those that fail to close spontaneously or have not healed within approximately six weeks. These wounds remain in a particular phase of wound healing, such as the inflammatory stage, for longer than normal. Acute and chronic wounds represent a substantial disease burden to the United States, affecting nearly ten million people every year at a cost in excess of $25 billion. Additionally, such wounds can cause patients severe emotional, physical, and financial stress.

Promotion of wound healing and regeneration remains the focus of intensive research and study, and there are currently numerous methods and compositions available to treat wounds and promote wound healing, including a myriad of passive and active dressings and bandages, and topical medicaments, as well as physical and/or chemical debridement of necrotic tissue. Despite this, the results of prior art methods have been inconsistent, and the treatment of chronic or slow healing wounds continues to pose a serious challenge. Accordingly, there is an urgent need for new compositions and methods for promoting wound healing and regeneration.

SUMMARY OF THE DISCLOSURE

The present disclosure relates to compositions and methods for modulating wound healing and regeneration. More particularly, the present disclosure relates to biomaterial scaffolds that may promote and expedite wound healing and regeneration.

In one aspect, the present disclosure provides a method for treating a wound in a subject that includes administering to the subject an effective amount of a scaffold and an immunomodulatory agent, thereby treating the wound.

In an embodiment, the scaffold comprises a biomaterial or a synthetic material. In some aspects, the biomaterial scaffold is a tissue-derived scaffold or a collagen scaffold.

In an embodiment, the immunomodulatory agent induces an adaptive immune system response.

In an embodiment, the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, a rate of wound healing is increased by 2%, 4%, 6%, 8%, or 10%.

In an embodiment, the scaffold is impregnated with the immunomodulatory agent.

In an embodiment, the wound is an acute wound, a chronic wound, or a surgical wound.

In an aspect, the present disclosure provides a method for treating a wound in a subject that includes administering to the subject an effective amount of an immunomodulatory agent, thereby treating the wound.

In an embodiment, the immunomodulatory agent is administered with a scaffold.

In an embodiment, the scaffold comprises a biomaterial or a synthetic material.

In an embodiment, the biomaterial scaffold is a tissue-derived scaffold or a collagen scaffold.

In an embodiment, the immunomodulatory agent induces an adaptive immune system response.

In an embodiment, the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, a rate of wound healing is increased by 2%, 4%, 6%, 8%, or 10%.

In an embodiment, the wound is an acute wound, a chronic wound, or a surgical wound.

In an aspect, the present disclosure provides a pharmaceutical composition for the treatment of a wound, the composition comprising an effective amount of an immunomodulatory agent.

In an embodiment, the composition is formulated to be impregnated in a scaffold.

In an embodiment, the scaffold comprises a biomaterial or a synthetic material.

In an embodiment, the biomaterial scaffold is a tissue-derived scaffold or a collagen scaffold.

In an embodiment, the composition is formulated for topical administration.

In an embodiment, the composition is formulated for administration with a biomaterial scaffold.

In an embodiment, the immunomodulatory agent induces an adaptive immune system response.

In an embodiment, the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, the composition increases a rate of wound healing by 2%, 4%, 6%, 8%, or 10%.

In an embodiment, the composition treats an acute wound, a chronic wound, or a surgical wound.

In an aspect, the present disclosure provides a method for promoting wound healing or tissue regeneration in a subject, the method comprising administering to said subject an effective amount of a scaffold and an immunomodulatory agent, thereby increasing the rate of at which the wound heals or the tissue regenerates.

In an embodiment, the scaffold comprises a biomaterial or a synthetic material.

In an embodiment, the biomaterial scaffold is a tissue-derived scaffold or a collagen scaffold.

In an embodiment, the immunomodulatory agent induces an adaptive immune system response.

In an embodiment, the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, a rate of wound healing is increased by 2%, 4%, 6%, 8%, or 10%.

In an embodiment, the scaffold is impregnated with the immunomodulatory agent.

In an embodiment, the wound is an acute wound, a chronic wound, or a surgical wound.

In an aspect, the present disclosure provides a kit for the treatment of a wound, the kit comprising an effective amount of an immunomodulatory agent and a biomaterial scaffold, and directions for the use of the kit for the treatment of the wound.

In an embodiment, the biomaterial scaffold is a tissue-derived scaffold or a collagen scaffold.

In an embodiment, the immunomodulatory agent is selected from the group consisting of wherein the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, the scaffold is modified to enhance immunomodulation.

In an embodiment, the scaffold fills the wound.

In an embodiment, the scaffold partially fills the wound.

In an embodiment, the immunomodulatory agent induces a T cell response.

In an embodiment, the immunomodulatory agent induces a T cell response in combination with a scaffold, wherein the scaffold is a biomaterial or a synthetic material.

In an embodiment, the immunomodulatory agent induces a T cell response.

In an aspect, the present disclosure provides a scaffold composition for the treatment of a wound that includes an effective amount of an immunomodulatory agent.

In an embodiment, the scaffold composition is formulated to be impregnated with the immunomodulatory agent.

In an embodiment, the scaffold composition comprises a biomaterial or a synthetic material.

In an embodiment, the biomaterial is a tissue-derived scaffold or a collagen scaffold.

In an embodiment, the scaffold composition is formulated for topical administration.

In an embodiment, the scaffold composition is formulated for co-administration with the immunomodulatory agent.

In an embodiment, the immunomodulatory agent induces an adaptive immune system response.

In an embodiment, the immunomodulatory agent is selected from the group consisting of Mineral salt adjuvants, Tensoactive adjuvants, Bacteria-derived adjuvants, Adjuvant emulsions, Liposome adjuvants, Polymeric microsphere adjuvants, Cytokines as adjuvants, Inulin-derived adjuvants, carbohydrate adjuvants, Adjuvant formulations, Mucosal adjuvants, Cytokines, and Cancer vaccine adjuvants.

In an embodiment, the immunomodulatory agent is a protein or small molecule.

In an embodiment, the small molecule is a peptide.

In an embodiment, the scaffold composition increases a rate of wound healing by 2%, 4%, 6%, 8%, or 10%.

In an embodiment, the scaffold composition treats an acute wound, a chronic wound, or a surgical wound.

In an embodiment, the wound is selected from the group consisting of a skin wound, a muscle wound, a cartilage wound, and a nervous system wound.

Other features and advantages of the disclosure will be apparent from the detailed description, and from the claims.

Definitions

By "binding to" a molecule is meant having a physicochemical affinity for that molecule.

By "ameliorate" is meant decrease, suppress, attenuate, diminish, arrest, or stabilize the development or progression of a disease.

By "compound" is meant any small molecule chemical compound, antibody, nucleic acid molecule, or polypeptide, or fragments thereof.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

As used herein, "modulating" refers to an increase or decrease in an adaptive immune system response. In a preferred embodiment, this relates to an increased, up-regulated or enhanced adaptive immune system response. An effective amount of an immunomodulatory agent is an amount that when applied or administered in accordance to the techniques herein is sufficient to modulate, preferably up-regulate, an adaptive immune system response.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "subject" is meant a mammal, including, but not limited to, a human or non-human mammal, such as a bovine, equine, canine, ovine, or feline.

By "reference" is meant a standard or control condition. In one embodiment, the effect of an agent on a cell is compared to the effect of the agent on a control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the disclosure, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Therapeutic agent" means a substance that has the potential of affecting the function of an organism. Such a compound may be, for example, a naturally occurring, semi-synthetic, or synthetic agent. For example, an agent may be a drug that targets a specific function of an organism or an antibiotic. A therapeutic agent may decrease, suppress, attenuate, diminish, arrest, or stabilize the development or progression of disease, disorder, or infection in a eukaryotic host organism.

As used herein, a "wound" refers to a physical disruption of the continuity or integrity of a tissue structure. "Wound healing" refers to the process of restoring the integrity of the tissue. The skilled artisan will understand that this may refer to a partial or a full restoration of tissue integrity. Accordingly, treatment of a wound refers to the promotion, improvement, progression, or acceleration of one or more stages or processes associated with the wound healing process. The wound may be acute or chronic. Chronic wounds may simply be described as wounds that fail to heal on a normal timeframe, which may vary depending on the nature of the wound and the specific tissue affected. The wound may also be any internal wound, e.g. where the external structural integrity of the skin is maintained, but the integrity of an underlying tissue/structure is disrupted.

BRIEF DESCRIPTION OF THE DRAWINGS

FIGS. 1A-1D: Biomaterial scaffolds induce a Th2 response in volumetric muscle wounds. C57BL/6 (WT) and B6.129S7-Rag1$^{tm1Mom}$/J (Rag$^{-/-}$) mice received a critical size quadriceps muscle injury and were treated immediately with 0.05 mL of saline, particulate collagen, bone ECM (B-ECM), or cardiac ECM (C-ECM).

FIG. 1A present line graphs that show proportions of myeloid (F4/80$^+$ Macrophages and CD11c$^+$ Dendritic Cells) and lymphoid (CD3$^+$ T cells and CD19$^+$ B cells) cell populations in WT wound environment, determined by flow cytometry (%=mean fraction of live cells across all treatments, bolded at peak level).

FIG. 1B is a bar graph showing the proportion of CD3$^+$ T cells that are CD4$^+$ Helper T cells or CD8$^+$ Cytotoxic T lymphocytes at 1 week post-injury treated with saline, collagen, B-ECM or C-ECM. Saline=white bars, Collagen=Light grey striped bars, Bone ECM=black bars, Cardiac ECM=grey bars.

FIG. 1C is a bar graph showing interleukin 4 gene expression in WT and Rag$^{-/-}$ mice at 1 week post-injury.

FIG. 1D is a graph showing 1 week post-injury transcriptome of CD3 cells sorted from wounded muscles treated with saline, collagen, B-ECM or C-ECM. Data are displayed as RQ to Saline-treated wounds. Data are means±SEM, n=4, ANOVA P<0.0001=**, P<0.001=*, P<0.01=**, P<0.05=*.

FIGS. 2A and 2B are bar graphs that show macrophages in wounded muscle are characterized for CD86 (FIG. 2A) and CD206 (FIG. 2B) expression by flow cytometry at 1 and 3 weeks post-operation in presence of saline or ECM scaffold in WT (Blue bars) and Rag$^{-/-}$ (red bars) mice. Mean of fluorescence (MFI).

FIG. 2C is a bar graph that shows CD206 expression at 3 weeks post-injury in C-ECM treated WT, Il4ra$^{-/-}$, Rag$^{-/-}$ and Rag$^{-/-}$ mice reconstituted with either WT CD4+ T cells (T-WT, n=2) or Rictor$^{-/-}$ CD4+ T cells (T-Rictr$^{-/-}$; Th2-deficient).

FIG. 2D is a graph that shows representative comparison of CD206 expression between WT, Il4ra$^{-/-}$, Rag$^{-/-}$ and Rag$^{-/-}$ reconstituted with WT and Rictor$^{-/-}$ CD4+ T cells.

FIG. 2E is a graph that shows gene expression analysis in cell sorted macrophages from wounded muscles 1 week post-injury and treated with collagen (light grey striped bars), B-ECM (black solid bars) and C-ECM (grey solid bars) compared to saline control. RQ to saline=$2^{-\Delta\Delta Ct}$.

FIG. 2F is a graph that shows RQ to saline in WT and Rag$^{-/-}$ mice when wounds were treated with C-ECM. The figure shows a loss of scaffold-mediated macrophage polarization in Rag$^{-/-}$ mice. WT=blue bars, Rag$^{-/-}$=red bars. Data are means±SEM, n=4; ANOVA (A-B) and Students T-test (D) **=P<0.0001, *=P<0.001, **=P<0.01, *=P<0.05.

FIG. 3A are images showing inguinal lymph node morphology at 1 week post-operation in saline (left) and C-ECM (right) treated WT type animals. Hematoxylin and eosin staining, scale bars=500 µm for composite and 200 µm for inset.

FIG. 3B are bar graphs showing Il4 gene expression in local draining lymph nodes (inguinal, top bar graphs) and distal lymph nodes (axillary/brachial, bottom bar graphs) in WT, Rag$^{-/-}$, and Cd4$^{-/-}$ mice at 1 and 3 weeks after wound treatment with collagen, B-ECM and C-ECM. RQ to saline is $2^{-\Delta\Delta Ct}$. Data are means±SEM, n=4; ANOVA **=P<0.0001, =P<0.01, *=P<0.05.

FIG. 4A is a bar graph that shows a treadmill exhaustion assay of mice at 6 weeks post-injury to test muscle function in WT (blue bars) and Rag$^{-/-}$ (red bars) mice. Normalized to uninjured control (=100%). n=5 mice per condition and genotype.

FIG. 4B is a bar graph that shows treadmill exhaustion at 3 weeks in Cd4$^{-/-}$, and Rag$^{-/-}$ mice repopulated with WT (T-WT) or Rictor$^{-/-}$ (T-Rictr$^{-/-}$; Th2 deficient) CD4$^+$ T cells. n=4 mice (Cd4$^{-/-}$) or n=10 mice (T-WT and T-Rictr$^{-/-}$).

FIG. 4C are images showing transverse section of quadriceps muscle at 6 weeks post-operation in collagen and C-ECM treated WT and Rag$^{-/-}$ mice. Black arrow=injury/treatment area. A=anterior, P=posterior.

FIG. 4D are images showing C-ECM treated VML at 3 weeks post-injury in WT, Rag$^{-/-}$, and Cd4$^{-/-}$ mice stained with hematoxylin and eosin. Small muscle fibers and ectopic adipogenesis are present in Rag$^{-/-}$ and Cd4$^{-/-}$ wounds. Scale bars=50 µm.

FIG. 4E is a bar graph showing gene expression of Adipoq (adipose marker) and Col1a1 (collagen I) showing increased adipose gene expression in Rag$^{-/-}$ as well as increased collagen gene expression suggesting alterations in connective tissue deposition and possible scarring. n=4 mice.

FIG. 4F is a cartoon showing T cell activation and polarization induce local Th2/M(IL-4) polarization of the SIM, promoting regenerative phenotypes such as wound healing and myotube fusion, and inhibit intramuscular adipose formation and collagen deposition. Data are means±SEM; ANOVA (A, D) and Students T-test (E) **=P<0.0001, *=P<0.001, **=P<0.01, *=P<0.05*.

FIG. 5A depicts a schematic showing extracellular matrix (ECM) scaffold preparation.

FIG. 5B depicts histological staining (hematoxylin & eosin) images of tissues pre- and post-processing.

FIG. 5C are images of in vitro flow cytometric analysis of iBMM (immortalized bone marrow macrophage; De Palma 2014) cell line cultured on varying ECM substrates identifies Bone (B-ECM) and Cardiac (C-ECM) as strong immuno-modulatory scaffolds. CD86=type-1 inflammatory macrophage, CD206=type-2 alternative macrophage.

FIG. 5D is a bar graph of in vitro flow cytometric analysis of iBMM (immortalized bone marrow macrophage and data are expressed as fold change over TCP control in the corresponding media condition (M1, M2, or M0). Data are means±SEM n=3.

FIG. 5E shows the mechanical properties of ECM scaffolds. Data represent means, Collagen n=2, Bone & Cardiac, n=3.

FIGS. 6A-6F Cell recruitment to muscle injury.

FIG. 6A shows gross images of mouse quadriceps muscle at 3 weeks post-operation.

FIG. 6B is a bar graph showing the total number of cells infiltrating saline- and scaffold-treated wounds.

FIG. 6C are bar graphs showing the percent of overall cell population identified as F4/80$^+$ macrophages, CD11c$^+$ dendritic cells, CD3$^+$ T cells or CD19$^+$ B cells. Data are means±SEM n=4.

FIGS. 6D-6F show bar graphs of type-2 (pro-regenerative) gene expression in wound environment with (WT, blue bars) and without (Rag$^{-/-}$, red bars) adaptive immune cells. Data are displayed as RQ to Saline-treated wounds.

FIG. 6G is a bar graph that shows fraction of myeloid cells positive for MHCII (I-A/I-E) antigen presentation in WT animals.

FIG. 6H depicts percent of overall cell population identified as F4/80$^+$ macrophages, CD11c$^+$ dendritic cells, CD3$^+$ T cells, CD19$^+$ B cells, or CD34$^+$ vascular progenitor cells.

FIGS. 7A-7D FoxP3$^+$ T$_{reg}$ populations at 1 and 3 weeks post-operation.

FIG. 7A depicts a bar graph showing the proportion of FoxP3$^+$CD4$^+$ T cells in the defect at 1, 3, and 6 weeks post-operation.

FIG. 7B depicts ANOVA of FoxP3$^+$ cell infiltration results over time. Data are means±SEM n=4.

FIG. 7C shows expression of IL4ra and CCR5 on CD4$^+$ and CD8$^+$ T cells at 1, 3, and 6 weeks post-operation.

FIG. 7D shows ANOVA data of CCR5 and IL4ra expression over time in CD4 and CD8 T cells. Data are means±SEM n=4.

FIG. 9: M2/M(IL4) Gene expression in scaffold-treated muscle wounds. Biomaterial scaffolds induced the expression of two M2/M(IL4) myeloid genes, Retnla (left) encoding Fizz1 and Arg1 encoding Arginase 1 (right). ANOVA ***=P<0.001, *=P<0.05. Data are means±SEM n=4.

FIGS. 10A-10G: Myeloid polarization in WT, Rag$^{-/-}$ and Cd4$^{-/-}$ mice.

FIG. 10A is a bar graph showing confirmation of participation of CD4$^+$ T cells in M2-myeloid polarization as determined in Rag$^{-/-}$ studies. CD206 mean fluorescence intensity in F4/80$^+$ macrophages from Cd4$^{-/-}$ mice compared to WT and Rag$^{-/-}$ mice at 3 wks post-injury.

FIG. 10B depicts statistical analysis of overall effect of genotype and scaffold on expression of CD86 and CD206 at 1 and 3 weeks post-surgery.

FIG. 10C depicts two-Way ANOVA data comparing CD86 and CD206 expression in scaffold treatment to Saline control wounds at 1 and 3 weeks post-surgery.

FIG. 10D depicts bar graphs showing mean CD86 fluorescence intensity data at 1 and 3 weeks post-surgery in CD11c$^+$F4/80$^-$ and CD11c$^+$F4/80$^+$ dendritic cells.

FIG. 10E depicts bar graphs showing CD206 fluorescence intensity at 1 and 3 weeks post-surgery in CD11c$^+$F4/80$^-$ and CD11c$^+$F4/80$^+$ dendritic cells.

FIG. 10F depicts two-way ANOVA data of CD86 and CD206 expression at 1 and 3 weeks post-surgery for CD11c$^+$F4/80$^-$ and CD11c$^+$F4/80$^+$ dendritic cells.

FIG. 10G depicts a bar graph showing CD19$^+$ B cell recruitment, characteristic of Th2 phenotype, dependent on CD4$^+$ T cells. Data are means±SEM n=4.

FIGS. 11A-11C Adoptive Transfer of CD4$^+$ T cells into Rag$^{-/-}$ mice.

FIG. 11A depicts a timeline of adoptive transfer studies.

FIG. 11B depicts graphs showing purity confirmation of CD4$^+$ T cells after isolation from WT and Rictor$^{F/F}$Cd4-Cre mice.

FIG. 11C depicts a graph showing confirmation of adoptive transfer at 11 days post-injection.

FIG. 12A depicts data of dCt of WT F4/80$^+$ cells. FIG. 12B depicts data of dCt of Rag$^{-/-}$ F4/80$^+$ cells. Saline=black dots, Bone=blue, Cardiac=red, Collagen=green.

FIGS. 13A-13C: Gene ontology analysis of adaptive immune dependent gene expression changes in SIM F4/80$^+$ macrophages associated with wound healing and tissue regeneration. Data displayed for genes significant in FIG. 11C (F4/80$^+$ Macrophages), input into STRING interaction database (Szklarczyk et. al 2015).

FIG. 13A depicts a gene interaction network.

FIG. 13B depicts GO processes that are significantly enriched (FDR P-value<0.05) from genes that alter expression in Rag$^{-/-}$ mice related to development and tissue regeneration.

FIG. 13C depicts a word map showing common terms in GO processes related to development and tissue regeneration.

FIG. 13E shows GO processes that were significantly enriched (Bonferroni p-value<0.05) from genes that altered expression in Rag$^{-/-}$ mice related to development and tissue regeneration.

FIG. 13F shows a Word map showing common terms in GO processes related to development and tissue regeneration.

FIG. 14C depicts ANOVA data of WT versus Rag$^{-/-}$ effect on gene expression. Data are means±SEM. (n=4, Saline, B-ECM, C-ECM; n=3, collagen).

FIG. 16A depicts hematoxylin and eosin-stained histological sections of unaffected and affected quadriceps muscle immediately after volumetric muscle loss surgery.

FIG. 16B depicts images showing increased fibrosis and decreased cellularity in collagen treated scaffolds in absence of adaptive immune cells (Rag$^{-/-}$) at 3 weeks post-injury.

FIG. 16C depicts mosaic images of quadriceps muscle at 3 weeks post-operation stained with Masson's trichrome (top) and Hematoxylin and Eosin (bottom). Scale bars=50 microns in (FIG. 16B) and 500 microns in (FIG. 16C).

FIG. 17A depicts bar graphs showing Col1a1 gene expression at 1 and 3 weeks post injury.

FIG. 17B depicts a bar graph showing adipogenesis gene expression shown as a fold change over WT in corresponding scaffold treatment at 3 weeks post-injury FIGS. 17C-17E show bar graphs of adipogenesis gene expression displayed as a fold change over saline control in (FIG. 17C) collagen, (FIG. 17D) B-ECM and (FIG. 17E) C-ECM treated injuries at 3 weeks post-injury. Data are means±SEM n=4. ANOVA *=P<0.001, =P<0.01, *=P<0.05.

FIGS. 17F-17J show that alterations in local and systemic immune phenotype correlated with differences in regenerative outcome of extracellular matrix.

FIG. 17F shows Hematoxylin and Eosin cross-sectional images of wounds at 3 weeks post-operation, specifically showing full cross sections of dissected muscle of saline- and cardiac-treated wounds.

FIG. 17G shows centrally nucleated fibers are larger in WT animals (left; white arrows) compared to Rag$^{-/-}$ animals (right; black arrows) with the same scaffold treatment.

FIG. 17H shows increased adiposity in Rag$^{-/-}$ animals compared to WT animals.

FIG. 17I shows RT-PCR of Col1a1 (Collagen I) at 3 weeks post-operation reveals decrease in WT animals that is negated in Rag$^{-/-}$ animals.

FIG. 17J shows AdipoQ (adiponectin) gene expression is increased in Rag$^{-/-}$ animals, WT=blue bars, Rag$^{-/-}$=red bars. FIG. 13F shows T cell activation and polarization induce a local Th2/M2 polarization of the SIM, promoting regenerative phenotypes such as wound healing and myotube fusion, and inhibit intramuscular adipose formation and collagen deposition. Data are means±SEM, n=4; ANOVA **=p<0.0001, =p<0.01, *=p<0.05*between scaffold types and Ψ between genotypes.

FIGS. 18A and 18B depict data showing Wilcoxon Rank Sum Test Results on sorted CD3$^+$ T cells (FIG. 18A) CD3$^+$ Genes analyzed in scaffold treated vs. saline control. (FIG. 18B) CD3$^+$ gene group analysis.

FIGS. 19A-19B: Wilcoxon Rank Sum and Linear Regression Test Results on sorted F4/80$^+$ macrophages in WT and Rag$^{-/-}$ mice.

FIG. 19A depicts Wilcoxon Rank Sum test on F4/80$^+$ Genes analyzed in scaffold treated vs. saline control.

FIG. 19B depicts Linear Regression model on material by genotype interaction. WT vs. Rag$^{-/-}$ comparison in effect of scaffold on gene expression changes versus saline treated control, p-values displayed for significant comparisons (P<0.05 in at least one scaffold treatments).

FIG. 19C shows a Wilcoxon Rank Sum test on F4/80$^+$ Genes analyzed in scaffold treated vs saline control.

FIG. 19D shows a Linear Regression model on material by genotype interaction. WT vs Rag$^{-/-}$ comparison in effect of scaffold on gene expression changes versus saline treated control, p-values displayed for significant comparisons (p<0.05 in one or both ECM scaffold treatments).

FIG. 20A shows cellular recruitment to volumetric muscle wounds. FIG. 20B shows MHCII expression on macrophages (F4/80+CD11b$^+$) and Dendritic Cells (CD11c$^+$ F4/80$^-$). FIG. 20C shows gating on Ly6c/Ly6g to identify immature monocytes (CD11b$^+$Ly6c$^+$) and polymorphonuclear cells (CD11b$^+$Ly6g$^+$) at 1 week post-surgery. FIG. 20D shows F4/80$^{hi}$ (F4/80$^+$) macrophage polarization in WT and Rag$^{-/-}$ mice. FIG. 20E shows T cell CD4:CD8 ratio.

DETAILED DESCRIPTION OF THE DISCLOSURE

Figure 1D:
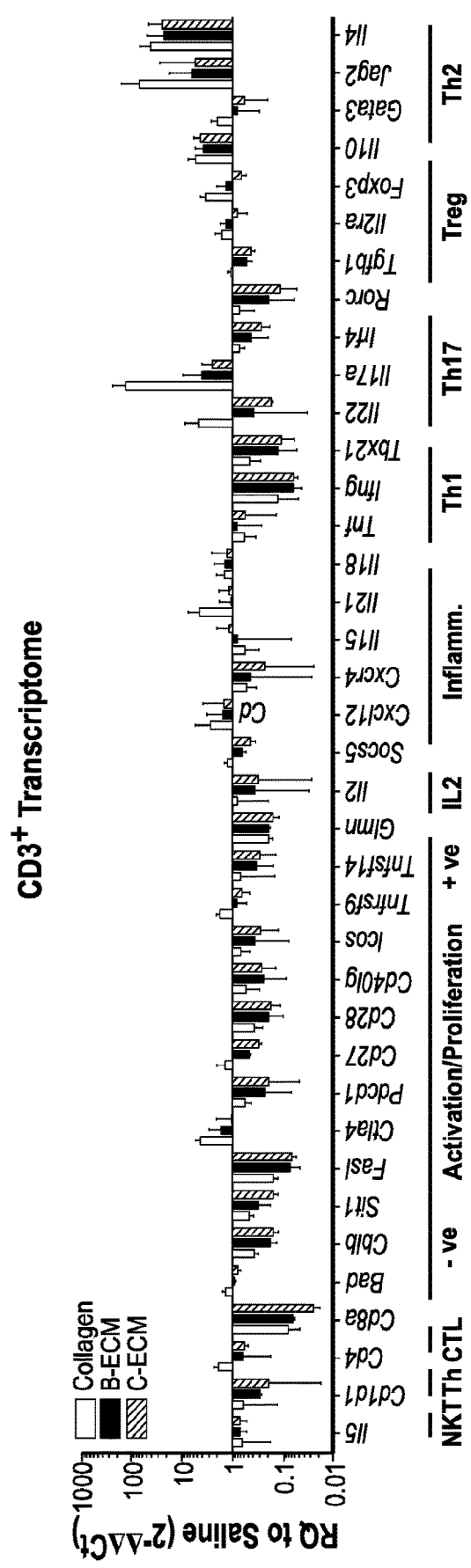

The present disclosure relates to compositions and methods for modulating wound healing and regeneration. More particularly, the present disclosure relates to biomaterial scaffolds that may promote and expedite wound healing and regeneration. The disclosure is based, at least in part, on the unexpected discovery that biomaterial scaffolds, tissue-derived and collagen-based, increase the number of immune cells in a site of a volumetric muscle defect. In particular, biomaterial scaffolds trigger a local and systemic type-2 immune response in which an M2 macrophage phenotype was dependent on a Thelper2 adaptive response to create a pro-regenerative environment characterized by high Interleukin 4 (Il4) levels.

Regenerative medicine therapies that primarily target stem cells have achieved limited success. An alternative strategy is to focus on immune cells, the first responders to traumatic wounds, which can interact directly with biomaterial scaffolds. Here, how biomaterial scaffolds shape the immune microenvironment in traumatic muscle wounds and ultimately impact tissue regeneration is investigated. A diverse population of immune cells is recruited into scaffolds and the surrounding area, including macrophages, T lymphocytes and B lymphocytes. The scaffolds induced a pro-regenerative type-2 response, characterized by an mTOR/Rictor-dependent Th2 pathway and IL-4-dependent macrophage polarization, which is critical for functional muscle regeneration. Targeting the adaptive components of the immune system during the process of biomaterials design may support the development of future therapies that efficiently control immune balance in tissues, ultimately stimulating tissue repair.

Wound Healing/Regeneration

Wound healing may be carried out by a variety of growth factors and cytokines that regulate cell growth, cell migration, cell differentiation, and cell proliferation (see e.g., Werner, S. and Grose, R., (2003) *Physiol Rev* 83:835-870). Wound healing may be divided into three general phases: inflammation, proliferation, and maturation (see e.g., Baum, C. L. and Arpey, C. J., (2005) *Dermatol Surg* 31:674-686). These three phases do not correspond to precisely defined time periods, and may overlap to some extent.

1. Inflammation Stage

The inflammation stage begins immediately following the creation of the wound, and may typically last up to about 6 days. The first stage within the inflammation stage immediately following wound creation is referred to as hemostasis, and typically involves fibrin and platelet mediated vasocontriction and clotting, mediated by fibrin and platelets, which function to control bleeding by forming clots. The clot may further serve as a temporary matrix for incoming fibroblasts and inflammatory cells, and also as a reservoir for cytokines and growth factors.

Following hemostasis, inflammatory cells may enter the wound and perpetuate the inflammatory stage. For example, inflammatory cells may include polymorphonuclear cells (PMNs), which are attracted by growth factors and cytokines such as platelet derived growth factor (PDGF) and interleukin 8 (IL-8). PMNs begin to clean the wound by removing cellular debris, foreign particles and bacteria that are present in the wound. In turn, PMNs are a major source of cytokines such as IL-1α, IL-10, IL-6, and TNF-α. Approximately three days after wound creation, PMNs are replaced by monocytes, which transform into macrophages that also act as wound cleaners and a further source of IL-1α, IL-1β, IL-6 and TNF-α. IL-10, IL-6, and TNF-α expression is strongly upregulated during the inflammatory phase (see e.g., Grellner, W. et al., (2000) *Forensic Sci Int* 113:251-264.; Grose, R., et al., (2002) EMBO Reports 3:575-582; and Hibner, G et al., (1996) Cytokine 8:548-556). IL-10 and TNF-α regulated fibrocytes play an important role in the inflammatory process and are specifically involved in collagen and cytokine production.

2. Proliferation Stage

The proliferation stage may begin as early as about three days after wound creation, and last up to several weeks. Granulation acts as a bridge between the inflammation and proliferation stages. For example, granulation tissue formation usually begins about 3-6 days after injury, and primarily contains fibroblasts and macrophages Migrating fibroblasts that produce a permanent collagen-based extra-cellular matrix (ECM) and macrophages that produce a variety of growth factors and cytokines such as IL-1 and TNF-α, which in turn stimulate the production of growth factors.

The fibroblast phenotype may have a significant influence on both wound healing responses and clinical outcomes (see e.g., Stephens, P et al. (1996) *J Dent Res;* 75: 1358-1364; Stephens, P et al. (2001) *Br J Dermatol;* 144: 229-237; and Stephens, P et al. (2004), *J Cell Sci;* 117: 3389-3403). For example, fibroblasts from tissues that exhibit preferential wound healing in vivo (e.g., oral mucosal tissue) exhibit distinct phenotype responses in vitro (al-Khateeb, T et al. (1997) *J Periodontol;* 68: 1063-1069). Furthermore, matrix metalloproteinases and serine proteinases may also play an important role in the regulation of cellular migration and ECM remodelling following injury. For example, decreased ECM reorganization and wound healing (e.g., chronic wounds) is associated with decreased fibroblast MMP production and activation (see e.g., Cook H et al. (2000) *J Invest Dermatol;* 115: 225-33). Chronic wound fibroblasts are often associated with decreased type I collagen lattice reorganization and contraction, as well as with delayed or impaired cellular ECM migration and wound repopulation capabilities in vitro, as compared to normal skin fibroblasts (see e.g., Cook et al, 2000).

Re-epithelialization is the next key event in wound healing and is initiated primarily by migrating keratinocytes, which are stimulated by various growth factors and cytokines. Keratinocytes undergo a number of phenotypic changes during migration, expressing proteins associated with the differentiating cellular phenotype. As migration proceeds, keratinocytes acquire a proteolytic phenotype by producing serine proteinases and MMPs. The keratinocytes continue to migrate into the wound space until the mitotically active keratinocytes undergo further phenotypic alteration, such that differentiation and stratification of the epithelium and re-formation of the basement membrane occurs, which completes re-epithelialization.

Cellular ECM attachment, ECM degradation by proteinases, and the overall regulation of these processes by cytokines and growth factors, are key features of wound remodelling and healing that co-ordinate cellular function (e.g., cell migration and wound contraction) via interactions with the ECM. Such interactions regulate cytoskeleton reorganization and new integrin-ECM interactions via, for example, Rho family and actin binding proteins, while proteinases remove existing integrin interactions, thereby allowing rear de-adhesion and cell migration (Martin, P., (1997) *Science;* 276:75-81; Stephens P and Thomas D W (2002) *J Wound Care;* 11:253-261; and Kirfel, G et al. (2004) *Eur J Cell Biol;* 83:717-724). Cellular contractility in the absence of rear de-adhesion results in dermal reorganization, as quantified experimentally by collagen lattice reorganization/contraction.

3. Maturation Stage

The maturation stage may begin anywhere from 4 days to several weeks after wound creation, and may last for weeks, months, or even years. Wound maturation (also known as remodelling) may take as little as days or weeks but the complete process can last up to several years. During this phase contraction, decreased redness, decreased thickness, decreased induration and increased strength of the wound is observed. The wound contracts under the influence of myofibroblasts, collagen production in the granulation tissue decreases and blood vessels diminish. Wound healing is then completed by further re-epithelialization.

Immune Cells in Wound Healing and Tissue Regeneration

Immune cells are direct participants in wound healing and tissue regeneration and their modulation using biomaterials is a promising approach for regenerative medicine. According to the techniques described herein, biomaterial scaffolds, tissue-derived and collagen-based, increase the number of immune cells in a site of a volumetric muscle defect. Biomaterial scaffolds trigger a local and systemic type-2 immune response in which an M2 macrophage phenotype was dependent on a Thelper2 adaptive response to create a pro-regenerative environment characterized by high Interleukin 4 (Il4) levels. This scaffold-associated immune microenvironment (SIM) included macrophages expressing Cebpb, Arg1 and Retnla (Fizz1) and T cells expressing increased Il4 and decreased Tbx21 and Ifng. When implanted in $Rag^{-/-}$ mice, deficient of adaptive immune cells, scaffold-associated macrophage (SAM) polarization was skewed towards an M1 phenotype and expression of pro-regenerative signals Il4, Fizz1 and Arg1, was lost. $Rag^{-/-}$ mice displayed altered regeneration including intramuscular adipogenesis and decreased muscle fiber size. The highly flexible immune system, first responder to trauma and biomaterials, is an attractive target for pro-regenerative therapies aimed at both the innate and adaptive immune systems. Immune homeostasis is indispensable to tissue development, wound healing, and regeneration (see e.g., Wynn, T. A., et al. *Nature,* 2013, 496(7446): p. 445-55; Stefater, J. A., 3rd, et al., *Trends Mol Med,* 2011, 17(12): p. 743-52). For example, in primitive organisms, such as the axolotl, macrophages play a critical role in regenerating entire limbs. In this regard, the cooperation between macrophages and T cells may be important for regenerative medicine. However, traditional tissue engineering and regenerative medicine approaches, employing tools including biomaterials, biological signals such as growth factors, and cells, have demonstrated only limited clinical successes to date.

Trauma initiates a cascade of local and systemic immune events that trigger the mobilization of cells into the damaged site to initiate host defense and tissue repair. The limited success achieved to date in rebuilding human tissues may be due in part to the tendency for therapeutic strategies to target later processes in wound healing and regeneration, such as stem cell proliferation and differentiation. Conversely, the immune system is a highly flexible network that serves as a guardian of tissue integrity, and its early response is adapted to the nature of the local tissue microenvironment (P. Matzinger and T. Kamala *Nature reviews. Immunology* 11, 221-230 (2011)). The immune system participates in tissue repair by scavenging debris and dead cells (Y. F. Peng et al. *Journal of autoimmunity* 29, 303-309 (2007)), recruiting and supporting proliferation of tissue progenitor cells (J. S. Otis et al. *PloS one* 9, e92363 (2014)), and inducing vascularization (S. Frantz, et al. *Circulation research* 96, 15-26 (2005)). Historically, immune interactions with implantable biomaterials were investigated with respect to biocompatibility (J. M. Anderson Annual Review of Materials Research 31, 81-110 (2001), J. M. Anderson and K. M.

Biomaterials 5, 5-10 (1984), and J. M. Anderson *ASAIO Journal* 34, 101-107 (1988)). However, immune responses initiated with biomaterials may provide an avenue for manipulation of immune-mediated tissue regeneration. Remodeling of tissue-derived biomaterials by cells from the innate immune system in animals and humans now correlates cell phenotypes with successful regenerative outcomes, although the mechanism and dynamics of forming the scaffold immune microenvironment remain unknown (B. M. Sicari et al. *Science translational medicine* 6, 234ra258 (2014), V. J. Mase, Jr. et al. *Orthopedics* 33, 511 (2010), and B. N. Brown et al. *Acta biomaterialia* 8, 978-987 (2012)). Furthermore, the role of the adaptive immune system in response to biomaterials and functional tissue regeneration outcomes is unknown and largely unexplored.

The role of tissue derived biomaterial scaffolds in shaping the regenerative immune microenvironment in a murine model of volumetric muscle loss (VML) and the resulting impact on functional tissue restoration was therefore investigated herein. A critical role for T cells in this process was thereby elucidated.

Biomaterial Scaffolds

Biomaterial scaffolds provide three-dimensional microenvironments that are designed to support cell proliferation, differentiation and new tissue production via specific physical (e.g., mechanical, morphological, and the like) and chemical (e.g., peptide, protein, small molecules, and the like) properties. Both synthetic and biologic materials may serve as scaffolds to engineer tissues in vitro using bioreactors or through direct in vivo implantation. More recently, biomaterial scaffolds have been implanted directly into defects to guide and modulate the wound healing response and tissue repair (see e.g., Hubbell, J. A., *Biotechnology* (N Y), 1995, 13(6): p. 565-76).

According to the techniques described herein, the immune system may work in concert with biomaterials in regenerative medicine. Without being bound by theory, it is believed that the limited success of prior art methods of rebuilding human tissues may be due, in part, to the lack of proper targeting of immune system components of the wound healing and regeneration process, such as stem cell proliferation and differentiation. The immune system is highly flexible, and its early response may be adapted to the nature of the local tissue microenvironment (Matzinger, P., *Nat Immunol*, 2007. 8(1): p. 11-3; Matzinger, P. and T. Kamala, *Nat Rev Immunol*, 2011. 11(3): p. 221-30). For example, the immune system may repair tissue by scavenging debris and dead cells (Peng, Y. F., et al., *J Autoimmun*, 2007, 29(4): p. 303-9); recruiting and supporting proliferation of tissue progenitor cells (Otis, J. S., et al., *PLoS One*, 2014. 9(3): p. e92363), and inducing vascularization (Frantz, S., et al., *Circ Res*, 2005, 96(1): p. 15-26). Thus, immune responses initiated by biomaterials according to the techniques herein may provide an avenue for manipulation of immune-mediated tissue regeneration.

Macrophages Activate T Cells and Thereby Recruit Cytokines, (e.g., Cytokine Il4)

As discussed above trauma initiates a cascade of local and systemic immune events, which trigger the mobilization of cells into the damaged site to initiate host defense and tissue repair. After trauma, the first cells to respond to the wound are polymorphonuclear cells, including neutrophils, eosinophils and basophils. Neutrophils are phagocytic cells of the innate immune system that scavenge debris and recognize cues from the environment and in turn produce paracrine factors that modulate the recruitment of other immune cells. One of these recruited cell types, the macrophage, also scavenges debris in the early stages of wound healing and later supports tissue development depending on phenotype.

Historical classification of macrophages defines the M1 phenotype (e.g., $CD86^+$ and Nos2, Tnfa expression) and M2 phenotype (e.g., $CD206^+$ and Arg1, Fizz1 expression) as opposite poles governing pro-inflammatory and anti-inflammatory or wound-healing responses, respectively. Recent evidence highlights the heterogeneity of macrophage phenotype and the role of multiple macrophage subtypes in cardiac wound healing (Epelman, S., et al. *Nat Rev Immunol*, 2015, 15(2): p. 117-29), scar formation, and outcomes of certain cancers (Lewis, C. E. and J. W. Pollard, *Cancer Res*, 2006. 66(2): p. 605-12). Macrophage polarization occurs along a spectrum, and a coordinated timing of the differing phenotypes enables clearance of infection followed by healing of damaged tissue. This polarization is mediated by both environmental factors and further, can be modified by signals from cells of the adaptive immune system, particularly T cells. Macrophages and dendritic cells present antigens and activate T cells, which in turn modulate other immune cells through secretion of cytokines. One such cytokine important for wound healing is interleukin 4 (Il4) (Tidball, J. G. and S. A. Villalta, *Am J Physiol Regul Integr Comp Physiol*, 2010. 298(5): p. R1173-87; Salmon-Ehr, V., et al., *Lab Invest*, 2000. 80(8): p. 1337-43). For example, production of Il4 by innate immune cells is necessary in muscle regeneration (Heredia, J. E., et al., *Cell*, 2013. 153(2): p. 376-88; Badylak, S. F., et al., *Tissue Eng Part A*, 2008. 14(11): p. 1835-42).

According to the techniques herein, biomaterials may induce influx of macrophages with a particularly strong M2 phenotype and that this phenotype may be dependent on the adaptive immune system, which is characterized by a Thelper2 phenotype. The enhanced Th2/M2 response may be associated with a pro-regenerative cytokine environment and enhanced regeneration of damaged muscle. Accordingly, T cells may be implemented as a new cellular target to promote tissue regeneration.

Test Compounds and Extracts

In general, immunomodulators that enhance wound healing/tissue regeneration (e.g., agents that specifically increase the ability of a biomaterial scaffold to recruit immune system molecules that enhance wound healing). Other agents that enhance the efficacy of an agent or molecule described herein are identified from large libraries of natural product or synthetic (or semi-synthetic) extracts, chemical libraries, or from polypeptide or nucleic acid libraries, according to methods known in the art. Those skilled in the field of drug discovery and development will understand that the precise source of test extracts or compounds is not critical to the screening procedure(s) of the disclosure. Agents used in screens may include known those known as therapeutics for the treatment of a neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound may be readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, Biotechniques 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have immunomodulatory activity that enhances wound healing/tissue regeneration, further fractionation of the positive lead extract may be necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

Pharmaceutical Therapeutics

In other embodiments, agents discovered to have immunomodulatory activity that enhances wound healing/tissue regeneration using the methods described herein are useful as a drug or as information for structural modification of existing compounds, e.g., by rational drug design. Such methods are useful for screening agents having an effect on a neoplasia.

For therapeutic uses, the compositions or agents identified using the methods disclosed herein may be administered systemically or locally to a subject to facilitate wound healing/tissue regeneration. Such agents may also be incorporated directly into a biomaterial scaffold of the disclosure to facilitate wound healing upon implantation of the scaffold. Preferable systemic routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic wound healing agent identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with wound healing/tissue regeneration, although in certain instances lower amounts will be needed because of the increased specificity of the compound.

Formulation of Pharmaceutical Compositions

The administration of an agent or compound or a combination of agents/compounds for the treatment of a wound may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/kg body weight to about 5000 mg compound/kg body weight; or from about 5 mg/kg body weight to about 4000 mg/kg body weight or from about 10 mg/kg body weight to about 3000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/kg body weight. In other embodiments, it is envisaged that doses may be in the range of about 5 mg compound/kg body to about 20 mg compound/kg body. In other embodiments the doses may be about 8, 10, 12, 14, 16 or 18 mg/kg body weight. Of course, this dosage amount may be adjusted upward or downward, as is routinely done in such treatment protocols, depending on the results of the initial clinical trials and the needs of a particular patient.

Pharmaceutical compositions according to the disclosure may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Methods of Treatment

In one embodiment, the present disclosure provides a method of using immunomodulatory activity to enhance wound healing/tissue regeneration in a subject. The methods involve administering to a subject having a wound an effective amount of a therapeutic combination of the disclosure. For example, a composition comprising an effective amount of an immunomodulatory agent that enhances wound healing. Preferably, such agents are administered as part of a composition additionally comprising a pharmaceutically acceptable carrier. In a further preferable method, such agents may be applied to, or incorporated into, a biomaterial scaffold. Preferably this method is employed to treat a subject suffering from a wound, in particular a large wound. Other embodiments include any of the methods herein wherein the subject is identified as in need of the indicated treatment.

Kits or Pharmaceutical Systems

The present compositions may be assembled into kits or pharmaceutical systems for use in ameliorating a wound. Kits or pharmaceutical systems according to this aspect of the disclosure comprise a carrier means, such as a box, carton, tube or the like, having in close confinement therein one or more container means, such as vials, tubes, ampoules, bottles and the like. The kits or pharmaceutical systems of the disclosure may also comprise associated instructions for using the agents of the disclosure. Kits of the disclosure include at least one or more immunomodulators that enhance wound healing/tissue regeneration. If desired, the kit also includes a reagent to be used as a biomaterial scaffold. The kit may include instructions for administering the immunomodulatory agent in combination with one or more agents that further enhance wound healing.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the disclosure, and, as such, may be considered in making and practicing the disclosure. Particularly useful techniques for particular embodiments will be discussed in the sections that follow.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

Example 1: Biomaterial Scaffolds Alter Immune Cell Recruitment in Volumetric Muscle Defects To model a traumatic wound and create a tissue gap for scaffold implantation, a portion of the quadriceps muscle group in C57BL/6 mice was surgically excised, provoking an irreversible volumetric muscle loss (VML) injury. The VML model was used to determine the role of biomaterial scaffolds on immune cell recruitment, shaping the immune microenvironment, and the Scaffold-associated Immune Microenvironment (SIM). Biological scaffolds have been used to repair muscle defects both in preclinical models and clinical testing (B. M. Sicari, et al. *Sci Transl Med,* 6(234): 234ra58. (2014)).

Figure 5A:
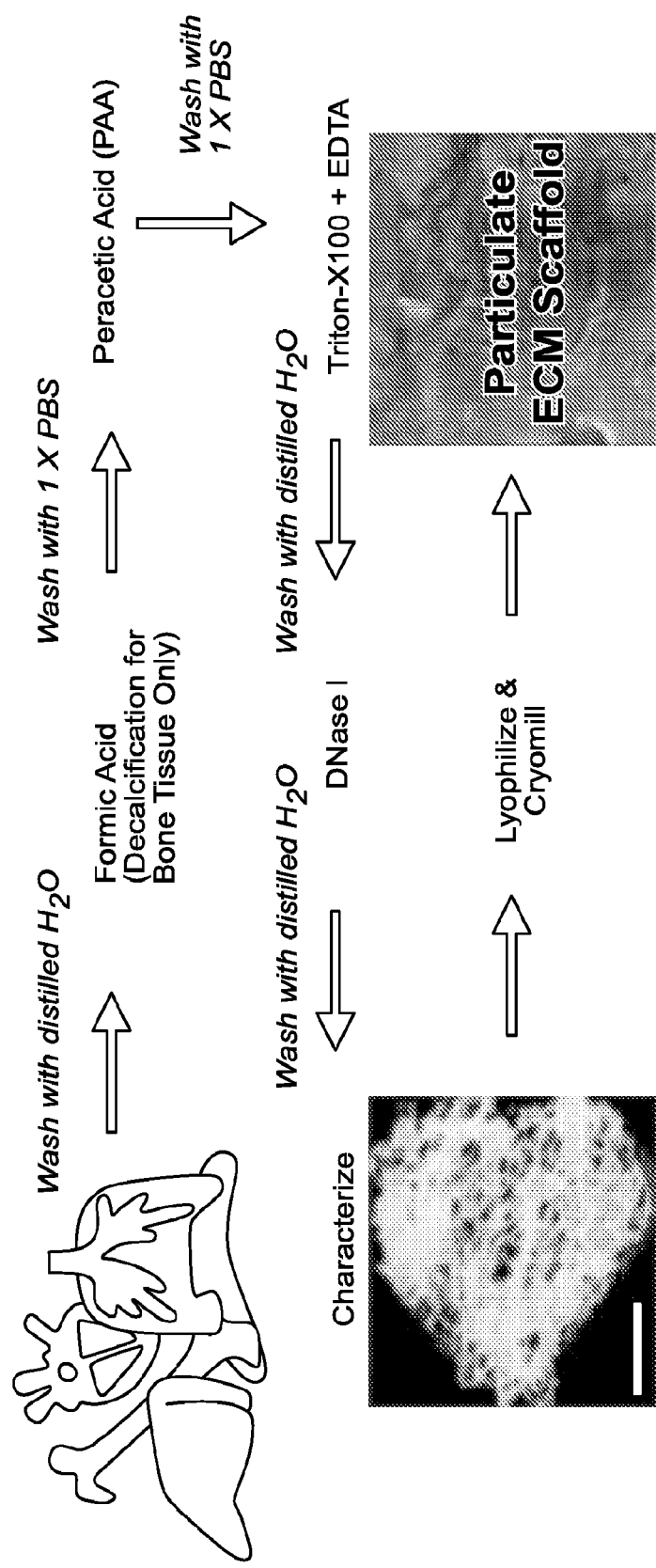
FIGS. 5A-E: Materials characterization and selection.
Figure 5B:
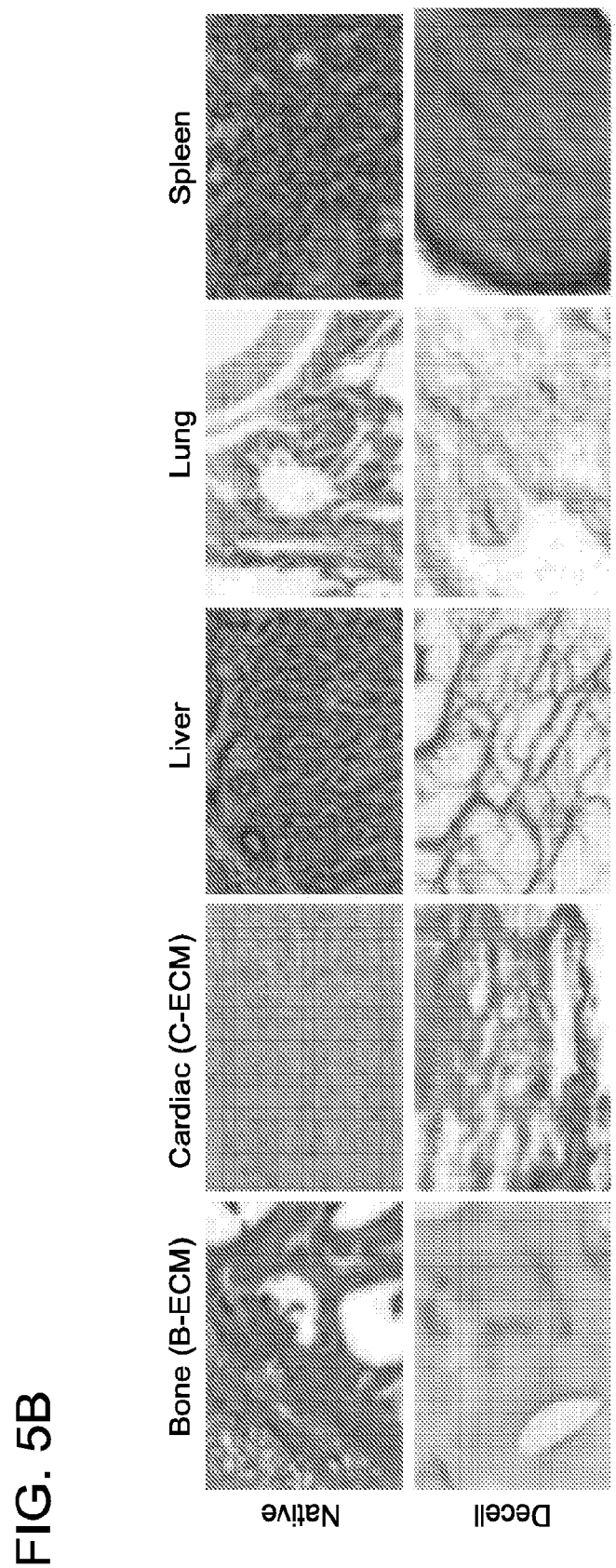
Figure 5C:
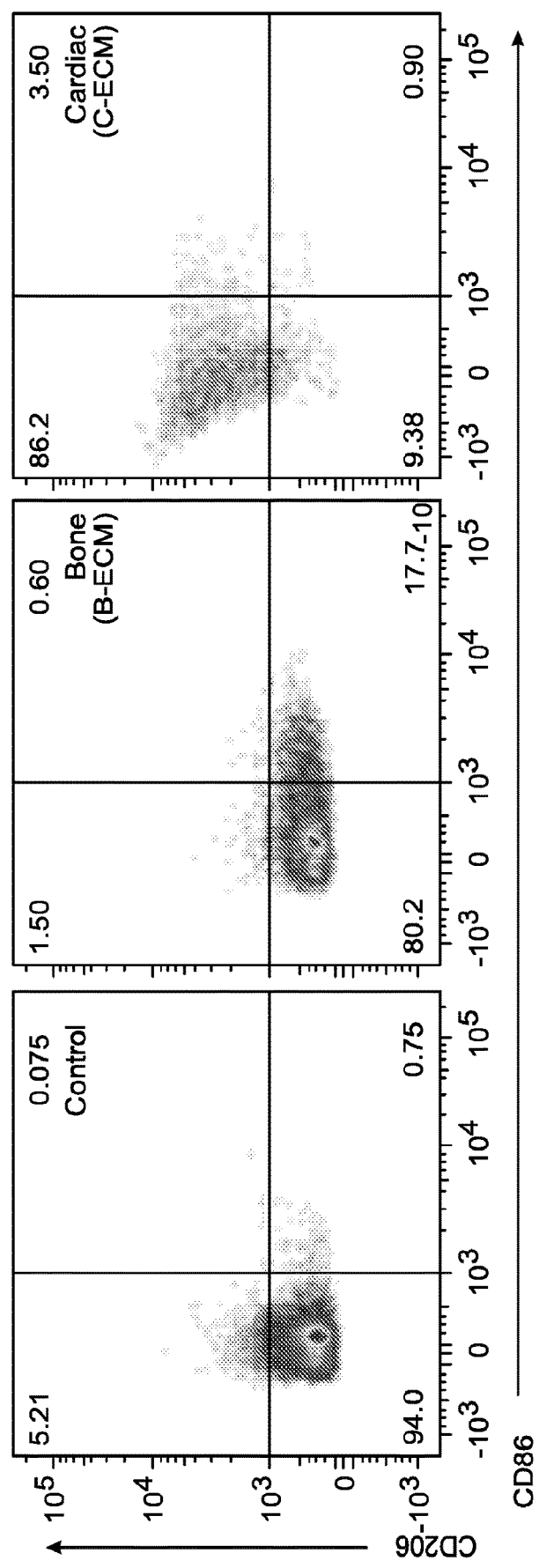
Figure 5D:
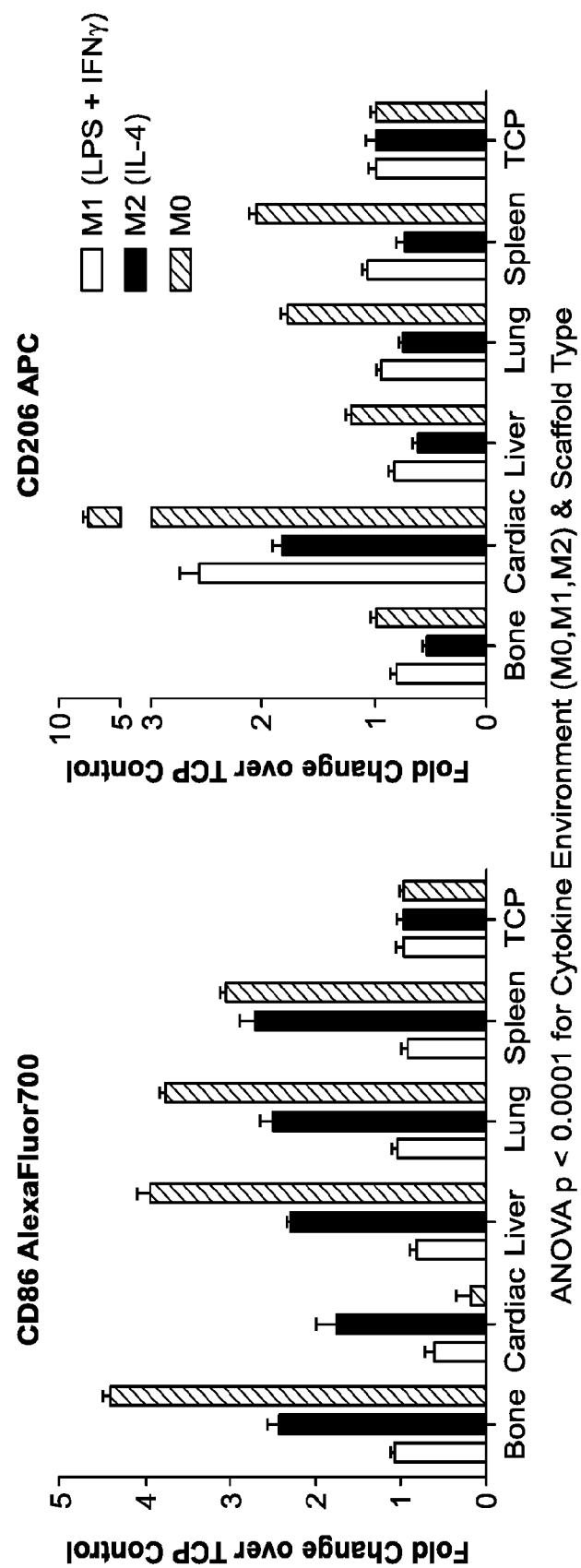
Figure 5E:
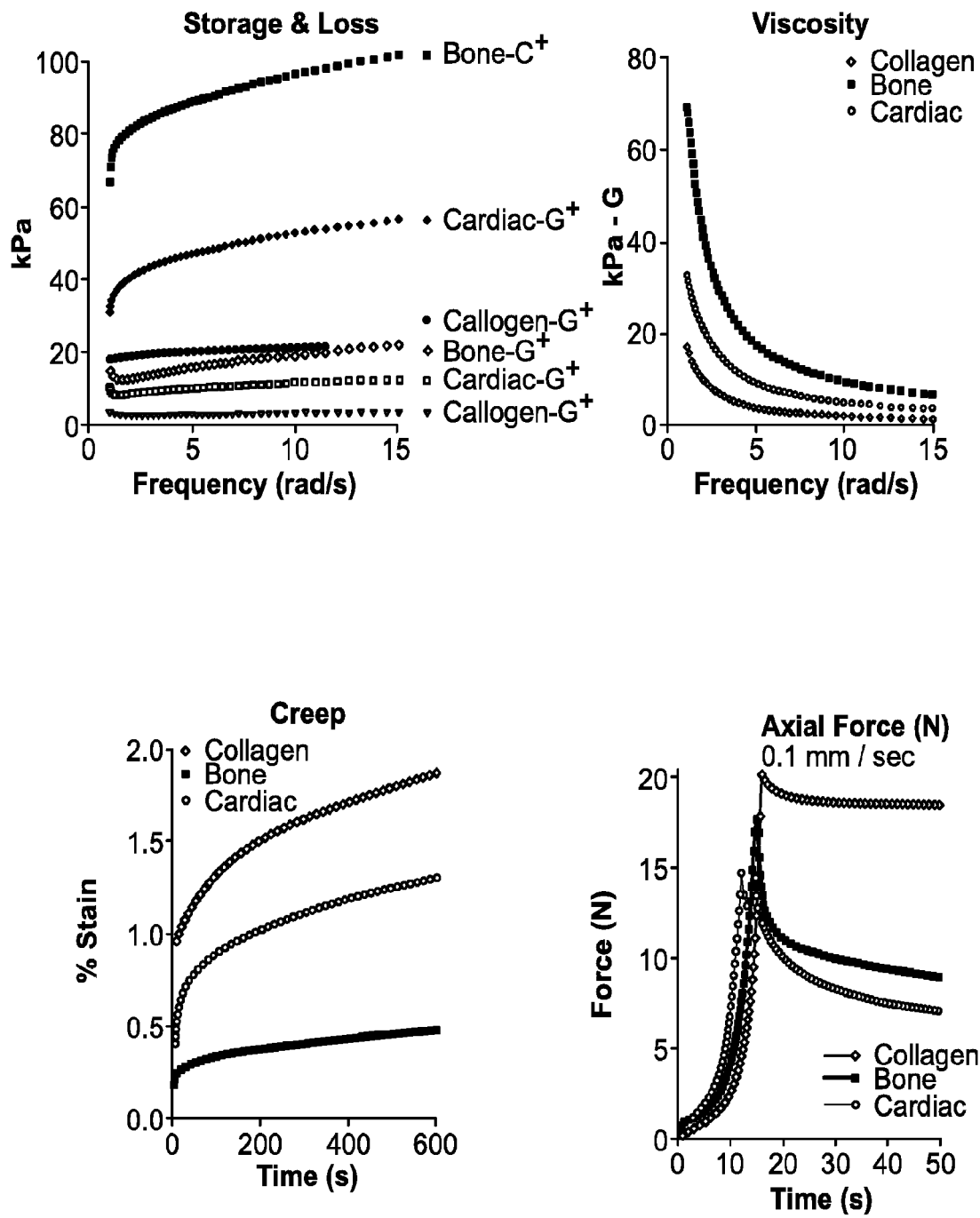

Accordingly, both tissue-derived and collagen biomaterial scaffolds were applied to the VML tissue defects. Tissue ECM scaffolds were generated by mechanical and chemical processing to produce particulates containing the tissue specific extracellular matrix with no intact cells (see e.g., FIGS. 5A, 5B and 5E). Based upon the clinical performance of biological and tissue-based scaffolds, a tissue ECM array was screened in vitro; bone- and cardiac muscle-derived tissue ECMs (B-ECM and C-ECM, respectively) were selected for their immunomodulatory properties (FIGS. 5A-5D and (V. Z. Beachley et al. *Nat Meth* advance online publication, (2015))). The tissue ECM scaffolds and a single-component biomaterial control (Type-1 collagen) were injected into muscle wounds, and the resulting immune cell infiltrates into the scaffold and adjacent muscle were characterized at several time points post-injury (FIGS. 1A-1D; FIGS. 6A-6E).

Using flow cytometry and histology, the SIM compared to saline-treated control wounds were analyzed with respect to the magnitude of immune cell recruitment (see e.g., FIG. 6B), types of cells present in the wound environment (see e.g., FIG. 1A and FIGS. 6A-6I), and the modulation of SIM polarization as determined by surface protein and gene expression analyses.

The presence of biomaterial scaffolds in the damaged tissue significantly increased the number of myeloid cells (F4/80$^+$ macrophages, CD11c$^+$ dendritic cells, CD11c$^+$F4/80$^+$ dendritic cells) and lymphocytes (CD3$^+$ T cells and CD19$^+$ B cells) at the injury site compared to saline control, as shown in FIGS. 6B and 1A and FIGS. 6A-6I), after 1 and 3 weeks (FIG. 1A, FIGS. 6A-6C). At 1 week, collagen treated wounds recruited the highest number of immune cells into the defect region (36.0%, 13.6 million cells) followed by bone (B-ECM) and cardiac (C-ECM) treated wounds (39.3%, 5.32 million and 45.4%, 5.44 million), with saline treated wounds containing the fewest number of cells (36.4%, 0.97 million).

Figure 6A:
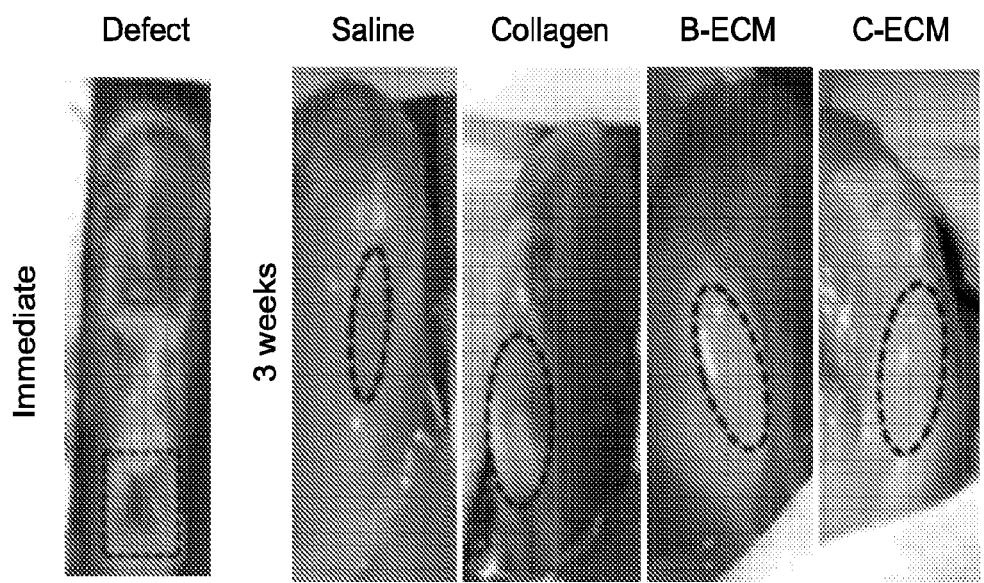
Figure 6B:
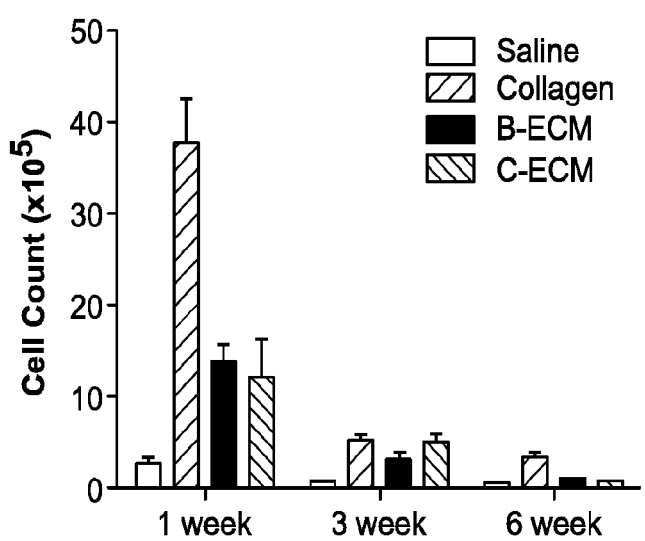
Figure 6C:
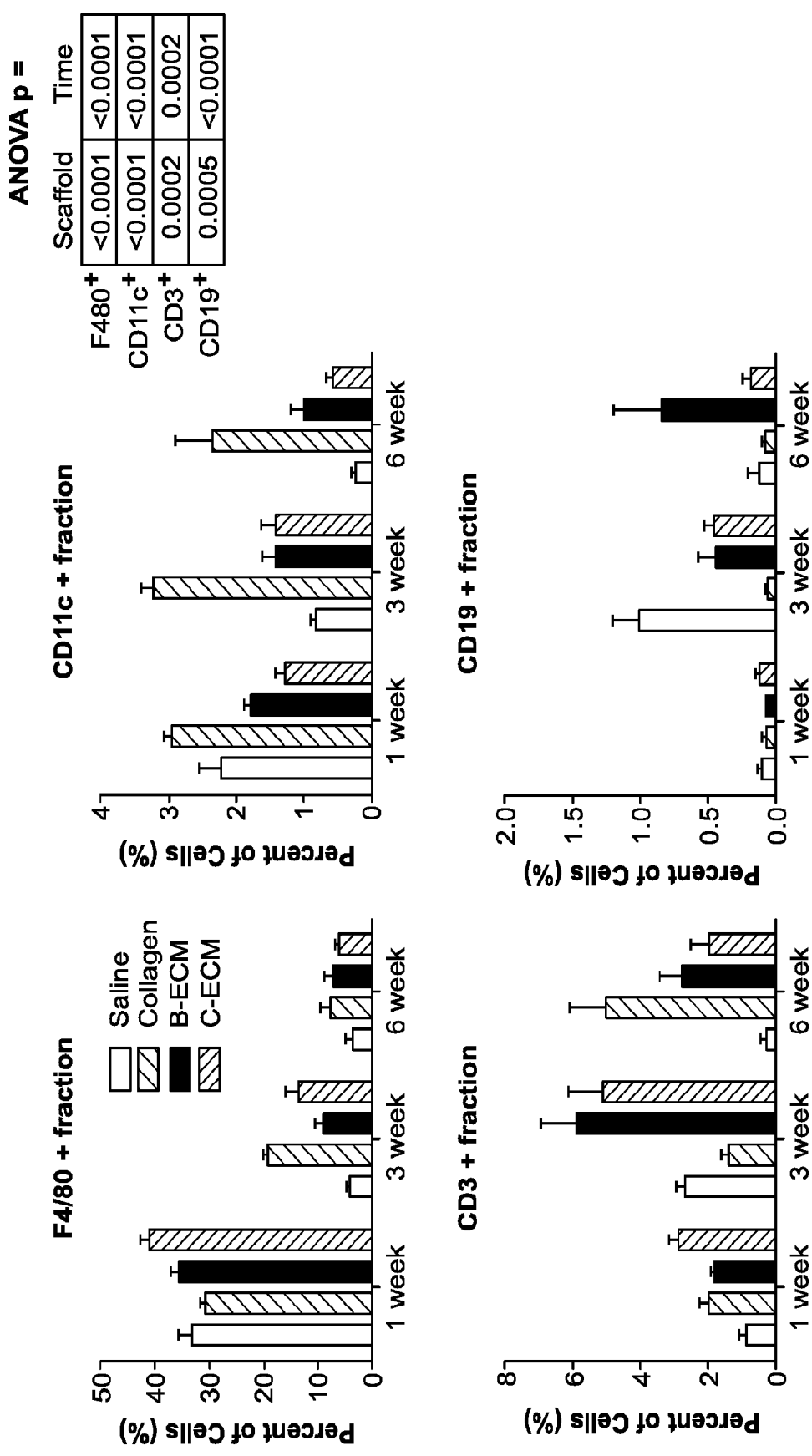
Figure 6I:
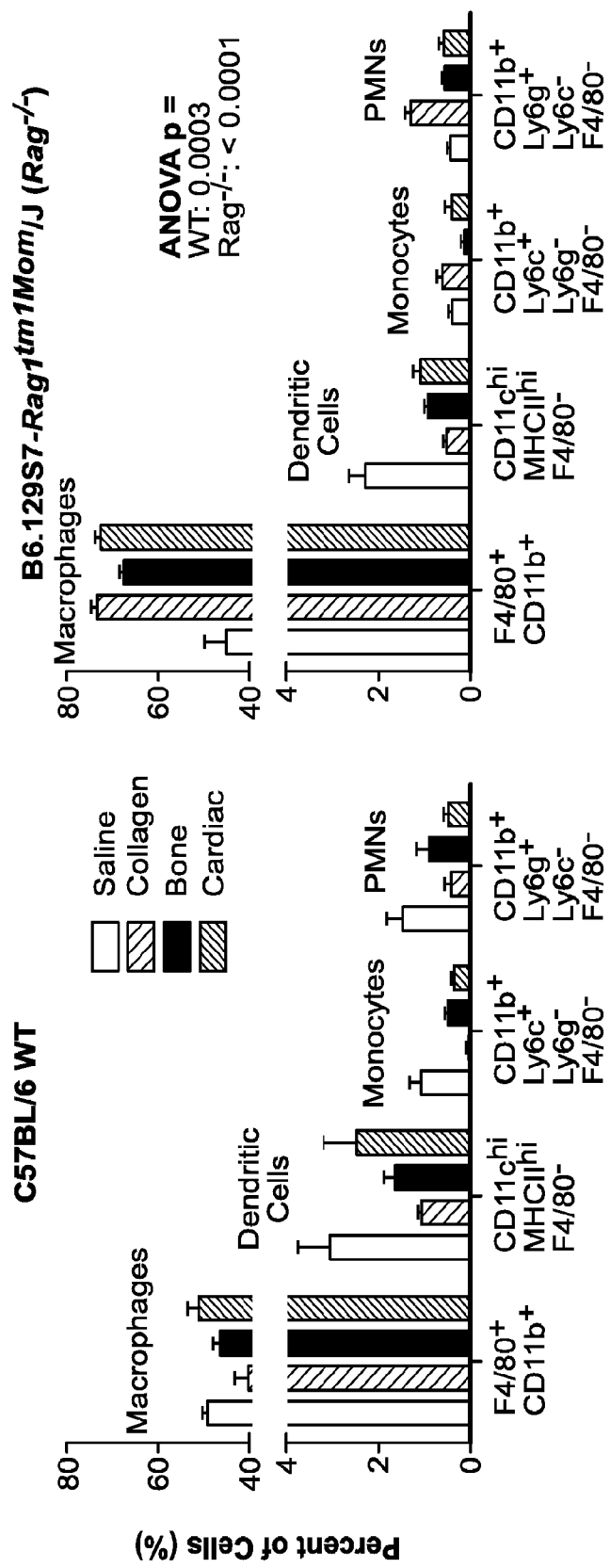
FIG. 6I shows myeloid infiltration at 1 and 3 weeks post-operation in WT and Rag$^{-/-}$ mice showing an increased fraction of myeloid cells in Rag$^{-/-}$ mice. Data are means±SEM n=4.
Figure 8:
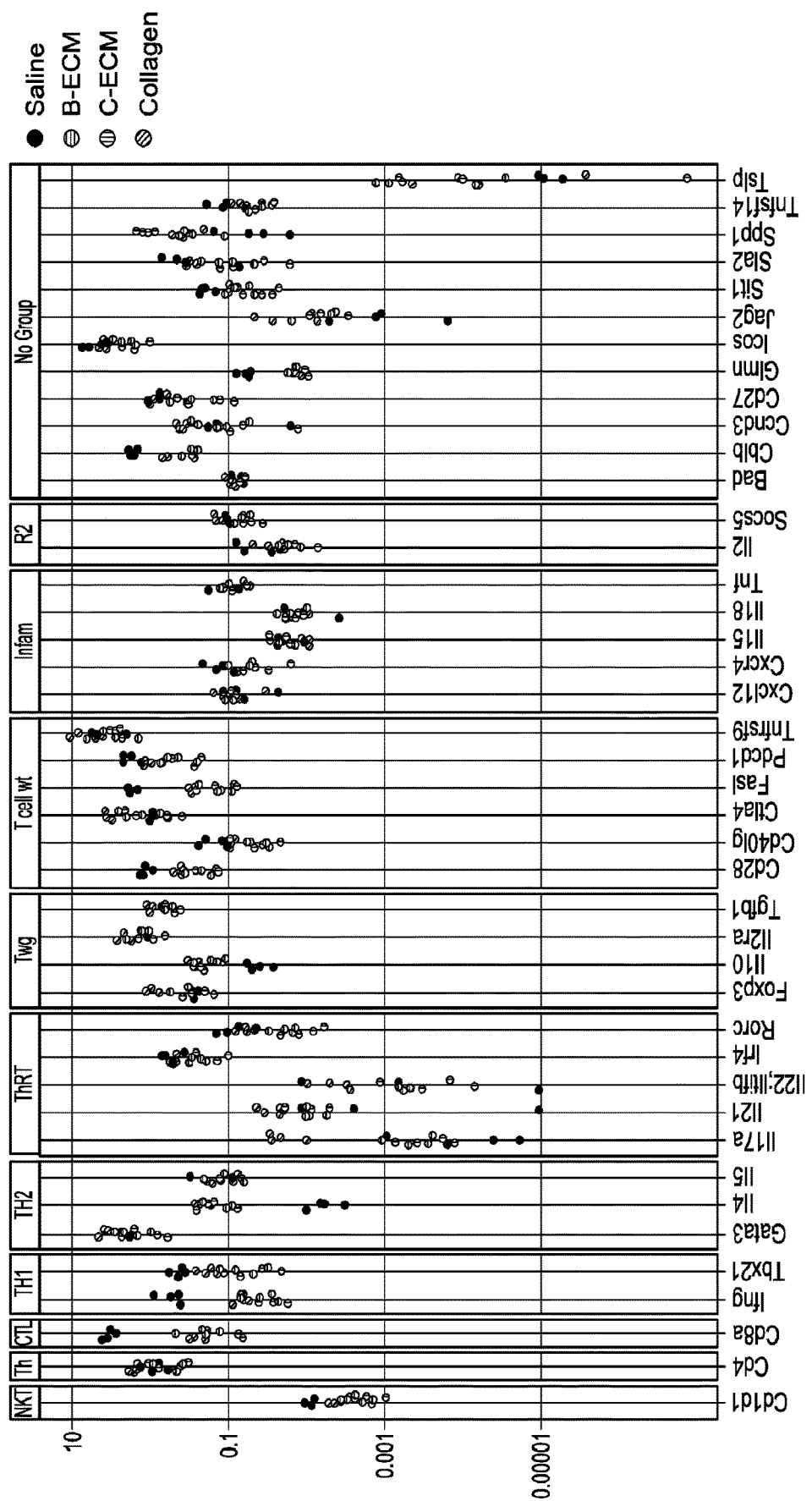
FIG. 8 depicts a graph showing data spread of gene expression profiling of CD3$^+$ cells sorted from 1 week post-surgery muscle defects. dCt of WT CD3$^+$ cells. Saline=Black dots. B-ECM=blue dots, C-ECM=red dots, Collagen=green dots.

As shown in FIG. 6I, at one-week post-surgery, a diverse myeloid component to the SIM was detected at the site of muscle injury and represented the peak infiltration of cells into the wound microenvironment. The proportion of myeloid cells peaked at 1 week post operation (F4/80$^+$ Saline 33.2%, Collagen 30.9%, Bone 35.6%, Cardiac 41.2%). The proportion of myeloid cells in the damaged muscle peaked at 1 week post injury, and the myeloid compartment represented the majority of immune cells at all times. The proportion of myeloid cells in the damaged muscle peaked at 1 week post injury, and the myeloid compartment represented the majority of immune cells at all times. The T cell fraction, consisting of both CD4$^+$ and CD8$^+$ cells, peaked in all treatment groups at 3 weeks post-injury (CD3$^+$ Saline 2.7%, Collagen 1.5%, Bone 5.9%, Cardiac 5.1%), but was present from the earliest times analyzed. The myeloid compartment (F4/80$^+$, CD11c$^+$) represented the majority of cells present at 1, 3 and 6 weeks post-operation. CD34$^+$ vascular progenitor cells were also detected in the wound microenvironment at low levels (<2%; FIGS. 6C and 6H). In the muscle wound, biomaterial scaffolds generally skewed the ratio of CD4:CD8 T cells towards a higher fraction of CD4+ helper T cells (~70% in scaffold treated, versus ~50% in saline treated wounds) at 1 week post injury (FIG. 1B). CD4+FoxP3+ regulatory T cells were also present in low levels and increased over time (FIGS. 7A and 7B).

Example 2: Scaffold Application and Adaptive Immunity Shape the Wound-Associated Immune Microenvironment Macrophages and dendritic cells, which serve as antigen presenting cells (APCs), can interact with CD4$^+$ helper T cells and CD8$^+$ cytotoxic T cells through presentation of peptide antigens associated with the MHCII and MHCI isoforms of the major histocompatibility complex, respectively. Bidirectional interactions of APCs with CD4$^+$ T cells can alter immune polarization of the environment by inducing secretion of cytokines such as IL-4, a major cytokine associated with both Thelper2 (Th2) and M2 pathways of T cell and macrophage differentiation, respectively.

Expression of MHCII (I-A/I-E) was detected at high levels on both F4/80$^+$CD11b$^+$ macrophages and CD11c$^+$F4/80$^-$ dendritic cells, though the significant number of MHC$^{-/low}$ CD11c cells signifies a large proportion of immature dendritic cells (see e.g., FIG. 6G). As shown in FIGS. 6D-6F, the expression levels of immune-related genes that support regeneration were also dependent on the presence and type of scaffold.

All scaffolds increased expression of Il4 (Il4; a canonical type 2 cytokine important in muscle healing (V. Horsley, et al. *Cell* 113, 483-494 (2003), V. Salmon-Ehr et al. *Laboratory investigation; a journal of technical methods and pathology* 80, 1337-1343 (2000), W. C. Gause, et al. *Nature reviews. Immunology* 13, 607-614 (2013), and J. E. Heredia et al. *Cell* 153, 376-388 (2013))) in the overall wound microenvironment (FIG. 1C), with IL-4 a known modulator of macrophage polarization and muscle regeneration—Il4 expression was elevated over saline control, with cardiac tissue ECM producing significantly greater levels (see e.g., FIG. 6D; WT blue bars). Biomaterial scaffolds also induced expression of the type-2/M2 macrophage markers Fizz1 (FIG. 6E) and Arg1 (FIG. 6F).

Figure 11A:
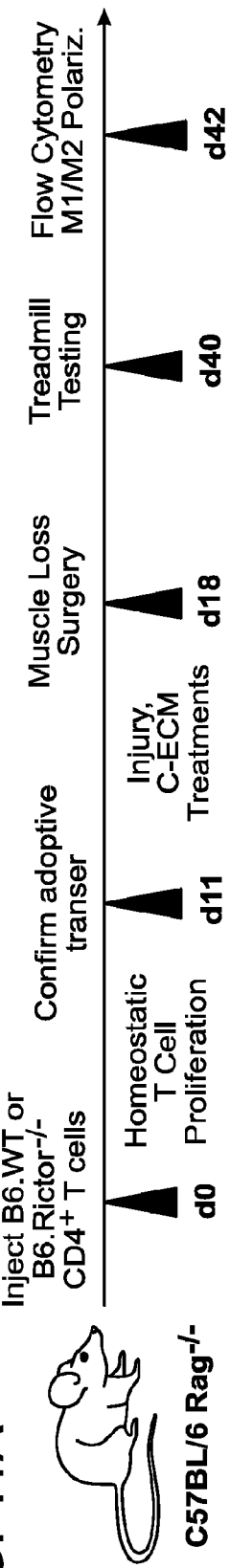
Figure 11A:
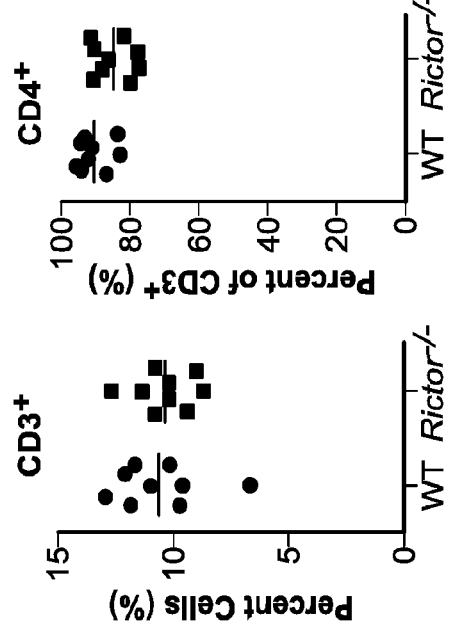
Figure 11A:
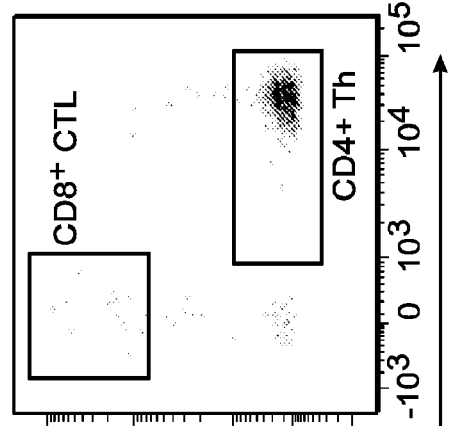
Figure 11A:
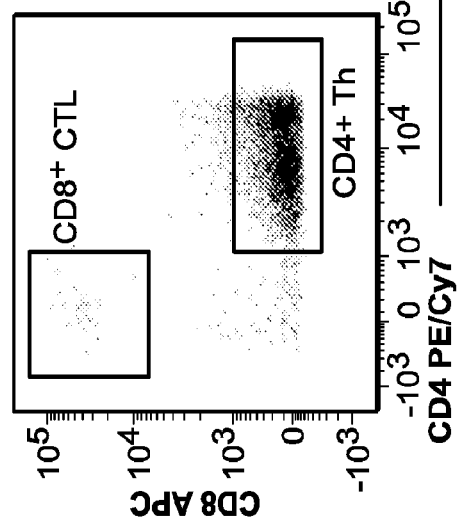

As previous studies have focused on the innate component of the immune microenvironment, the participation of adaptive immune cells was evaluated. The detection of CD3$^+$ T cells along with M2-type macrophages in the wound microenvironment 1 week post-trauma specifically prompted performance of experiments designed to understand the role of adaptive immunity on the polarization of the wound environment towards a pro-regenerative type-2 immune response. For example, in addition to WT animals, scaffolds were also implanted into B6.129S7-Rag$^{tm1Mom}$/J (Rag$^{-/-}$) mice, which lacked mature T and B cells. In Rag$^{-/-}$ mice, scaffold-mediated Il4 up-regulation was lost, suggesting a Th2-driven scaffold immune microenvironment. To further characterize the scaffold-associated T cell population in wild type mice, CD3$^+$ cells were sorted out of muscle injuries at 1 week post-operation for detailed gene expression analysis (FIG. 1D; FIGS. 11A-11C; FIGS. 18A and 18B). Expression levels of Il4, Fizz1 and Arg1, respectively markers of Th2 (Il4) and M2 (Fizz1 and Arg1) phenotypes, were severely decreased when implants were made in Rag$^{-/-}$ mice (FIG. 6D-6F; red bars), which indicated an important role of lymphocytes in type-2 polarization by ECM scaffolds.

Example 3: Adaptive Immune System Enables Local Biomaterial-Mediated Enhancement of Type-2 Polarization Macrophages and dendritic cells carry self and foreign antigens to local draining lymph nodes, where they interact with and activate resident T cells. Activated T cells migrate to the site of injury where they may participate in SIM polarization. The strong influx of macrophages and T cells (FIG. 1A) corresponds with the detection of Arg1 and Fizz1 only in the wound environment of mice displaying a Th2 immune response (FIG. 6D), suggesting that a dominant Th2 response to the wound in presence of scaffolds is responsible for the recruitment of M2-type macrophages, which are in return beneficial for wound healing and tissue regeneration.

Figure 2A:
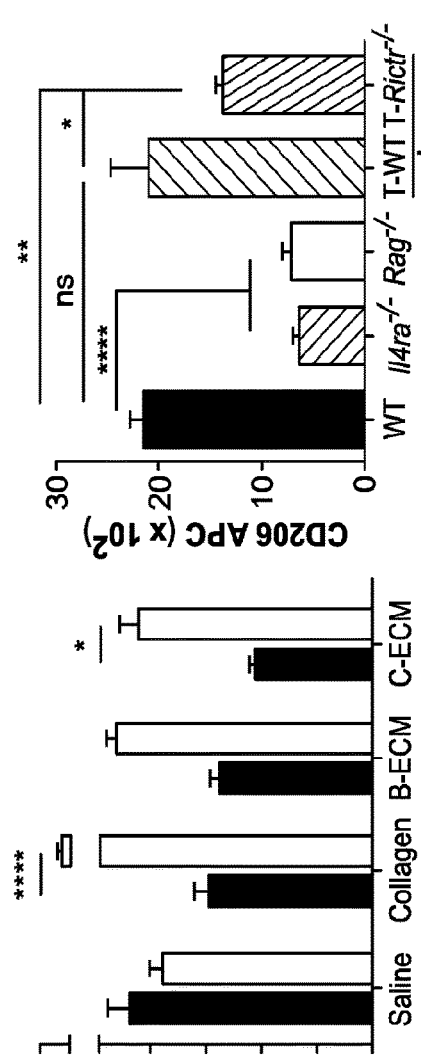
FIGS. 2A-2F: M(IL-4) pro-regenerative myeloid polarization induced by scaffolds is Th2-dependent. Scaffold microenvironment and adaptive immunity shape the wound-associated myeloid compartment. Myeloid cell recruitment and polarization were measured via flow cytometry at 1 and 3 weeks post-operation and analyzed as a function of extracellular matrix (ECM) scaffold application and adaptive immune presence.

The macrophages recruited into the scaffold microenvironment, in the presence and absence of T and B cells, were characterized by comparing the expression of CD86 (a co-stimulatory molecule expressed at high levels by inflammatory type-1/M1 macrophages) and CD206 (a mannose receptor and type-2/M2 marker) in both wild type and $Rag^{-/-}$ mice, respectively (FIGS. 2A-2F; FIGS. 10A-10G). In the presence of adaptive immune cells, biomaterial scaffolds inhibited CD86 up-regulation at 3 weeks post surgery, as shown in (WT; blue bars) (FIGS. 2A-2G). In $Rag^{-/-}$ mice (red bars), however, this mitigation of CD86 expression was lost, and ECM scaffold treated wounds returned to a macrophage polarization profile resembling that of saline treated control animals (FIG. 2A). The dampening of CD86 expression, which indicates inhibition of type-1 polarization, displayed the unique nature of scaffold-associated macrophages (SAMs) that differentiates them from other wound-associated myeloid cells.

While all scaffolds produced comparable CD86 expression in wounds of normal mice 3 weeks (see e.g., FIG. 2A), collagen treatment in $Rag^{-/-}$ mice significantly upregulated CD86 expression to a greater extent (10× WT levels versus ~2× for scaffold-treated wounds). These results indicated that adaptive immune cells are necessary for reducing M1 polarization in wounds treated with biomaterial scaffolds.

Figure 2B:
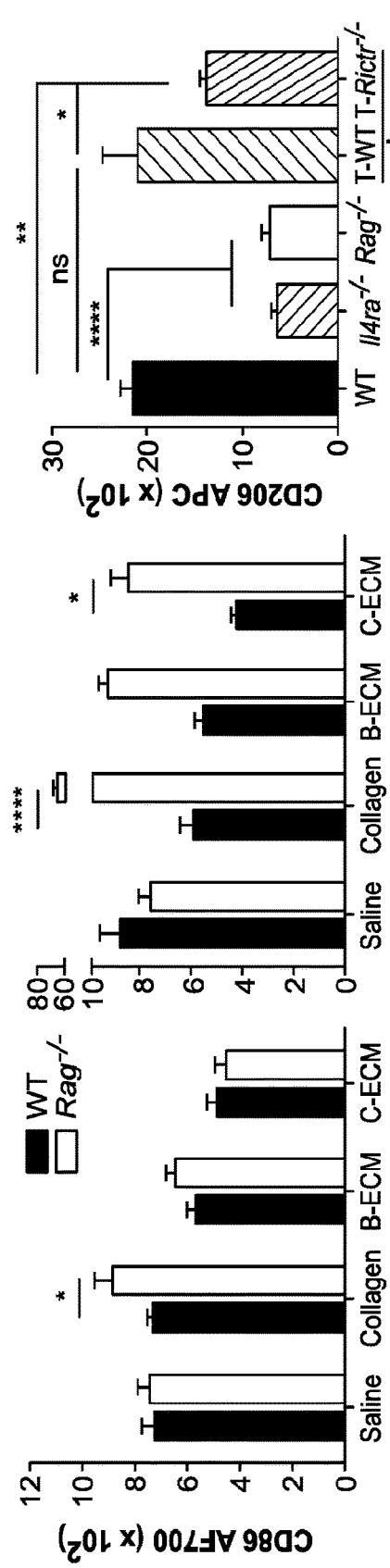
Figure 2C:
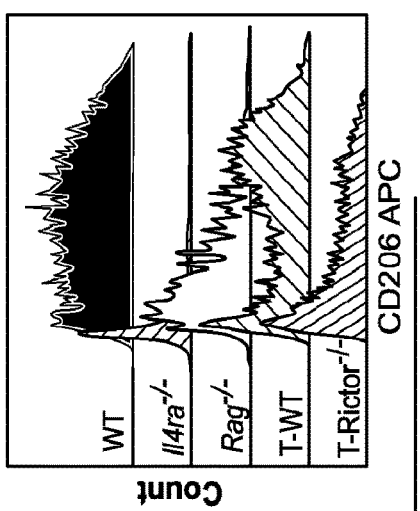
Figure 2D:
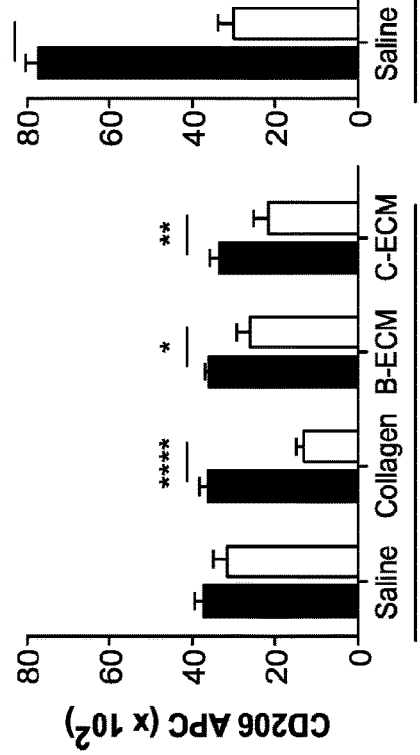
Figures 10C, 10D:
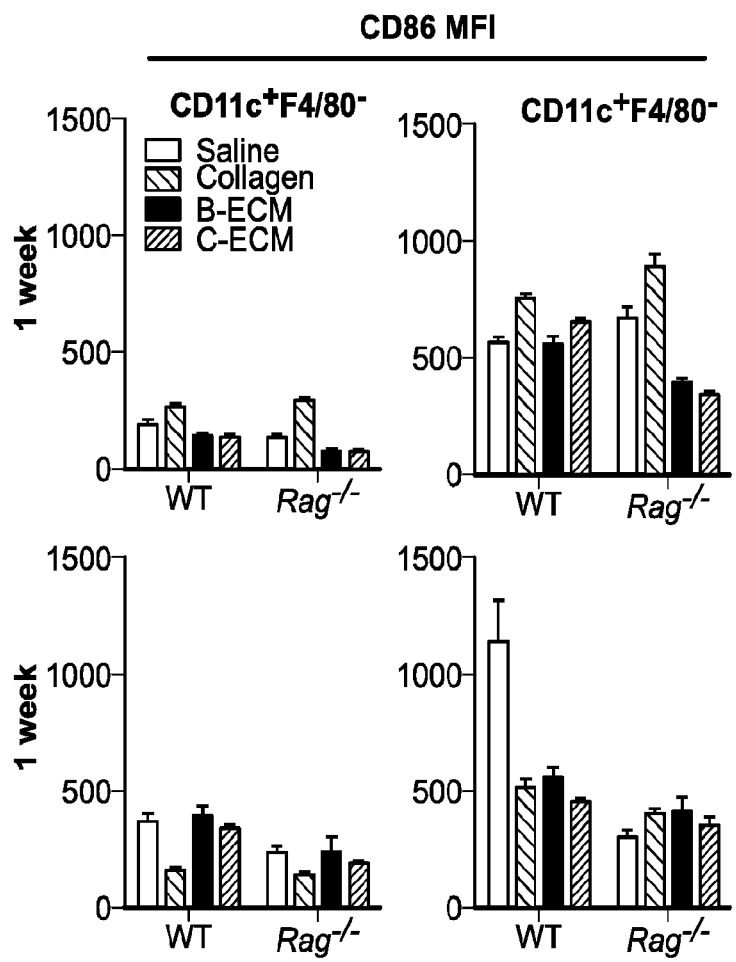
Figure 10F:
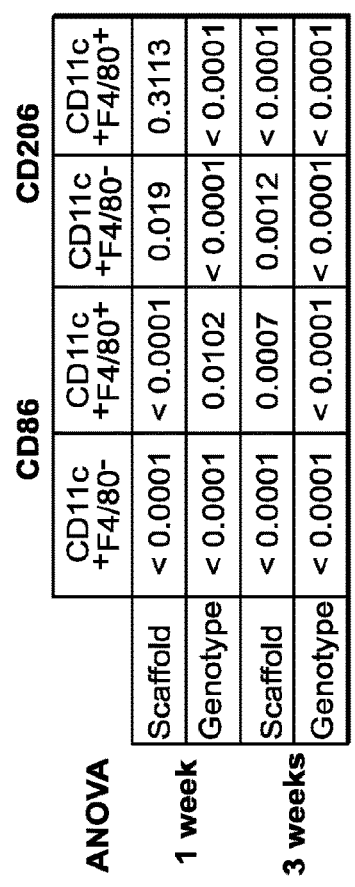
Figure 10G:
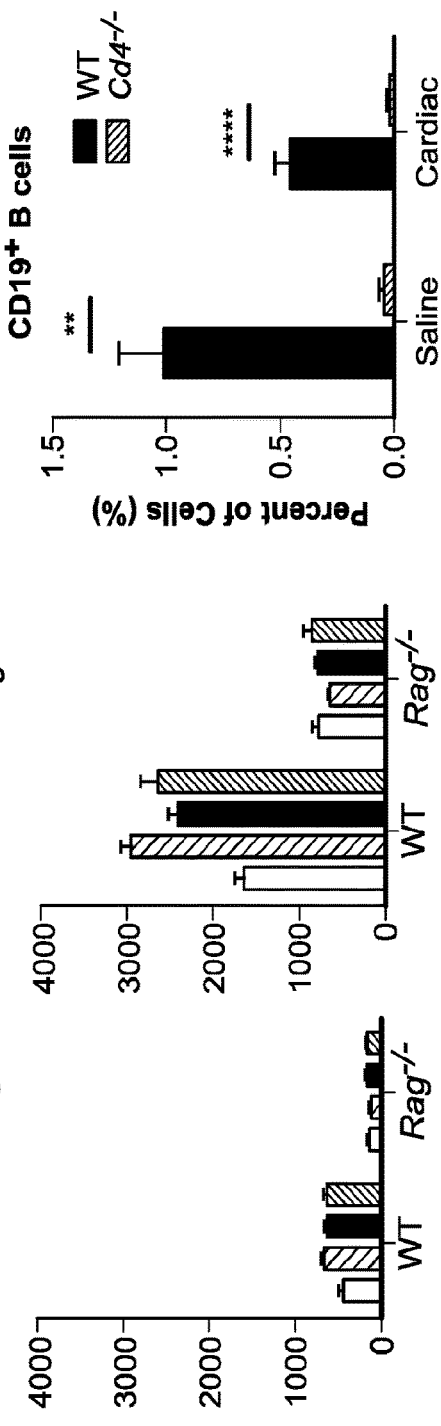
Figure 10E:
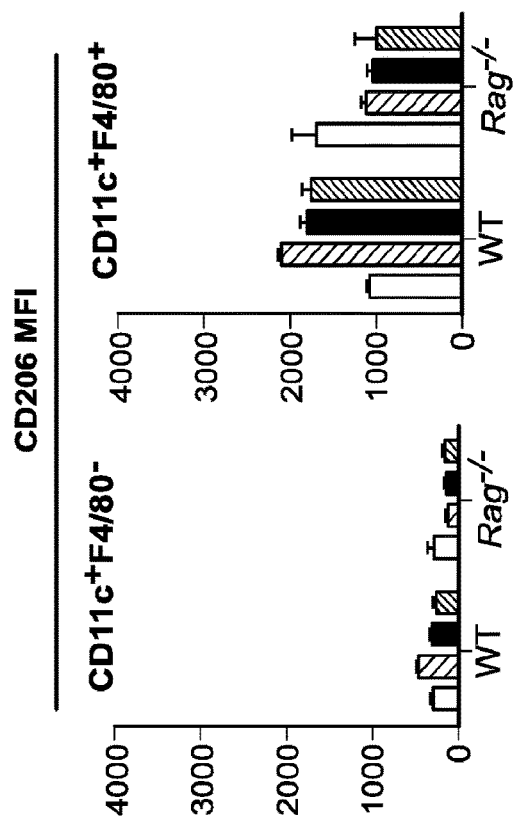

On the other hand, CD206 expression was similar between ECM scaffold-treated and saline-treated mice post-implantation, with increased expression at 3 weeks (FIG. 2B). However, this observed increase in CD206 expression by myeloid cells at 3 weeks was ablated in $Rag^{-/-}$ mice in both scaffold and saline treated wounds, suggesting that the adaptive immune system has an additional scaffold-independent role in shaping the wound healing response (see e.g., FIGS. 2B and 2H). Moreover, this CD206 up-regulation was also impaired in B6.129S2-Cd4$^{tm1Mak}$/J mice (Cd4$^{-/-}$) mice, which maintain B cells and CD8+ T cells but lack CD4+ helper T cells (FIG. 10A). Additionally, in Cd4$^{-/-}$ mice, the recruitment of B cells (a Th2-dependent adaptive effector cell) was diminished (FIG. 10G). Collagen treatment severely decreased CD206 expression in $Rag^{-/-}$ mice, which confirmed that collagen treatment is a potent natural stimulus for M1 myeloid cell differentiation in the absence of signals from the adaptive immune system, as shown in FIG. 2B. Alterations in CD86 and CD206 expression were also observed on CD11c$^+$ dendritic cells, as shown in FIGS. 10A-10F.

Since the expression levels of CD86 and CD206 are not mutually exclusive on macrophages (M1 versus M2), the polarization of the SIM was assessed via cell sorting of F4/80$^+$ macrophages and CD3$^+$ T cells at 1 week post-injury to compare their gene expression profiles between WT and $Rag^{-/-}$ mice. As shown in FIG. 1D, several differences were noted in both T cells and macrophages, as shown in FIGS. 2E and 2F and FIGS. 8, 12A and 12B, 18A and 18B, and 19A and 19B. When comparing bone and cardiac-derived ECM-treated defects to saline-treated defects, both tissue ECMs induced similar patterns of gene expression alteration relative to saline control. Notably, however, cardiac tissue ECM induced a greater magnitude of change.

As shown in FIG. 1D, SIM T cells were highly skewed toward the Th2 phenotype (as demonstrated via increased Il4 expression), with concomitant decreases in Th1 gene expression (Ifng and Tbx21). Scaffolds induced a Th2-type gene expression profile as characterized by increased Il4 expression and decreased expression of Ifng and Tbx21 (Th1 canonical genes). In addition, Jag2, which encodes the Notch ligand Jagged 2, was elevated. Jagged 2 helps direct Th differentiation away from Th1 and toward Th2 (D. Amsen, et al., *Immunity*, 27(1):89-99. (2007); T. C. Fang, et al., *Immunity*, 27(1):100-10. (2007)). 110, which encodes a general anti-inflammatory cytokine that is not Th-specific, was also up-regulated. Spp1 encodes osteopontin, a secreted phosphoprotein involved in bone remodeling and immune cell signaling. Interestingly, Spp1 was more highly induced in T cells infiltrating cardiac SIM than bone SIM. Other genes that are more selectively expressed by Th1 cells, such as Fas1 and Cd28 (the co-stimulatory receptor for CD86), were likewise down-regulated. Cd8a is also down-regulated in SIM, concomitant with the decreased proportion of CD8 T cells observed during flow cytometry (see below, FIG. 1B, 3A, 3B and FIG. 22B). Notably, treatment with collagen, but not B-ECM or C-ECM, which was shown to be associated with higher cellularity, (see e.g., FIGS. 6B and 1A) induced the expression of cytokines associated with a Th17 immune signature with elevated expression of Il17a and Il22 (elevated expression of Il21, Cd4, and T cell activation markers such as Ctla4 and Tnfsfr9 (encoding 4-1BB) were also observed). This gene expression profile in the CD3 compartment was coincident with a higher expression of Il17ra by macrophages (see e.g., FIG. 2E).

Concomitant with Th2 polarization of sorted T cells, SIM macrophages upregulate genes encoding the canonical M2 molecules Arg1 and Retnla (encoding Fizz1) relative to saline, confirming the results of individual qRT-PCR analyses for these genes as shown in FIGS. 6A-6G, and FIG. 1A. Additionally, Cebpb, a bZIP transcription factor critical to M2 development and associated with increased muscle strength in mice and humans (J. Blackwell et al. *The journal of physiological sciences*: JPS 65, 145-150 (2015), D. Ruffell et al. *PNAS* 106, 17475-17480 (2009)), was highly upregulated in the presence of the biomaterial scaffolds, (e.g., in SIM), particularly with the cardiac scaffold. M1 associated genes were variably altered—Nos2 was slightly increased, while Ifnγ was decreased. S100a8 was increased in SIM; while this molecule was originally reported as a DAMP (damage associated molecular pattern), it has more recently been shown to inhibit inflammatory responses induced by pathogen-associated molecular patterns (PAMPs) such as LPS (Y. Sun, et al. *Mol Immunol*, 53(4): 443-9. (2013)).

Interestingly, Timp1 was up-regulated, while Mmp16 and Mmp9 were down-regulated. Timp1 inhibits activation of both Mmp9 and Mmp16; thus, metalloproteinase activity is highly dampened in the scaffold associated immune microenvironment (e.g., SIM). While these MMPs are thought to promote angiogenesis via release of activated pro-angiogenic factors, they have also been reported to block muscle repair (M. E. Davis, et al. *J Appl Physiol* (1985), 115(6):884-91. (2013)). By this reasoning, the Timp1$^{hi}$Mmp9/16$^{lo}$ expression pattern of the scaffold-associated macrophages (e.g., SIM) would enhance muscle regeneration.

Figures 2E, 2F:
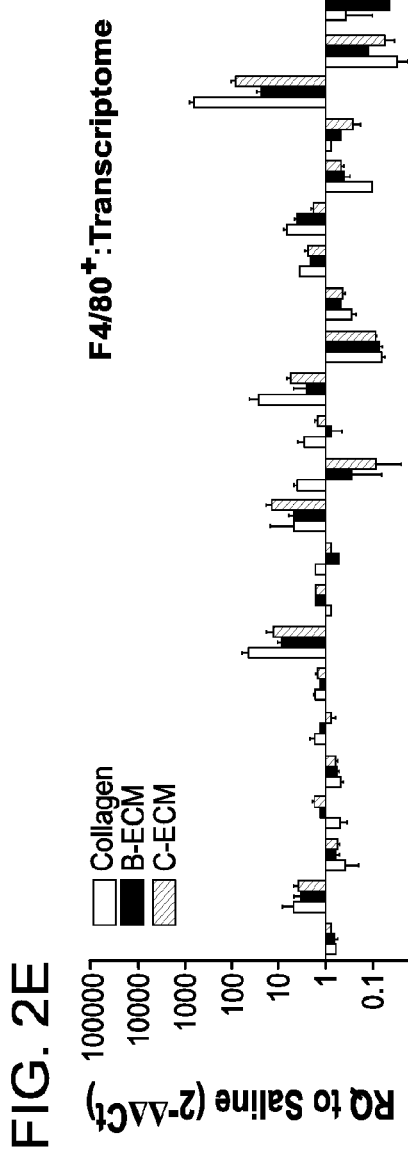
Figure 2G:
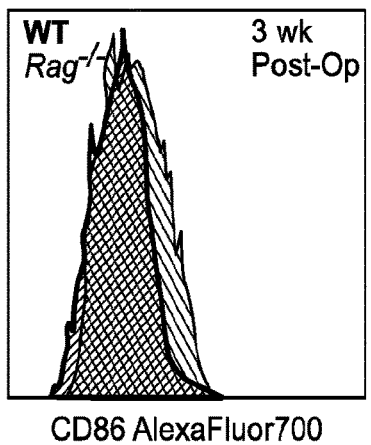
FIG. 2G shows representative FACS histogram showing Bone ECM-treated wounds with heightened CD86 expression in Rag$^{-/-}$ mice (red open) over WT mice (blue solid).
Figure 2H:
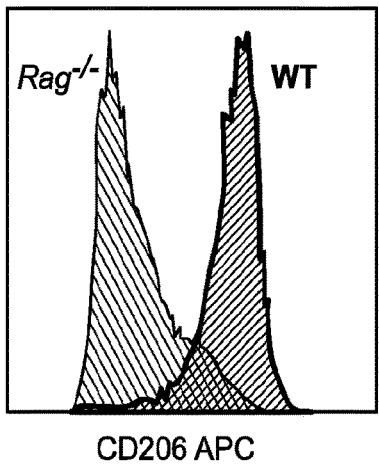
FIG. 2H shows a representative FACS histogram showing decreased CD206 expression in Bone ECM-treated wounds at 3 weeks post-operation.
Figure 2I:
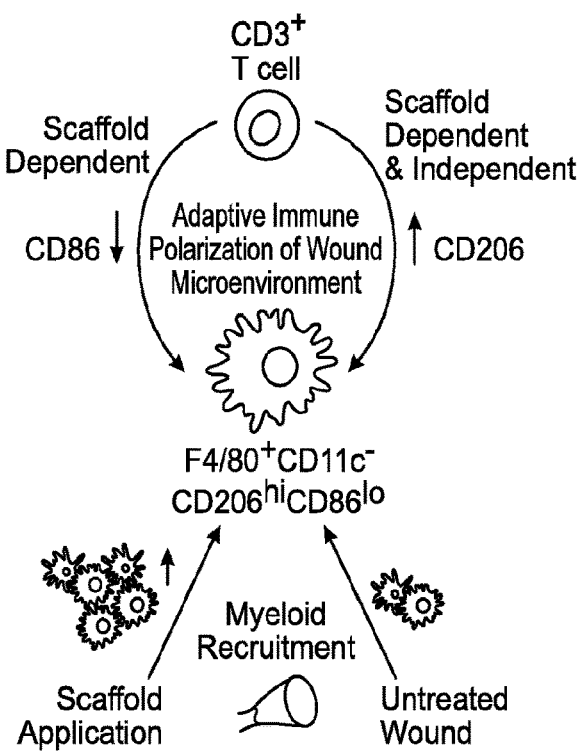
FIG. 2I shows a schematic depicting the role of environment and adaptive immunity in shaping the wound-associated myeloid compartment.
Figure 12A:
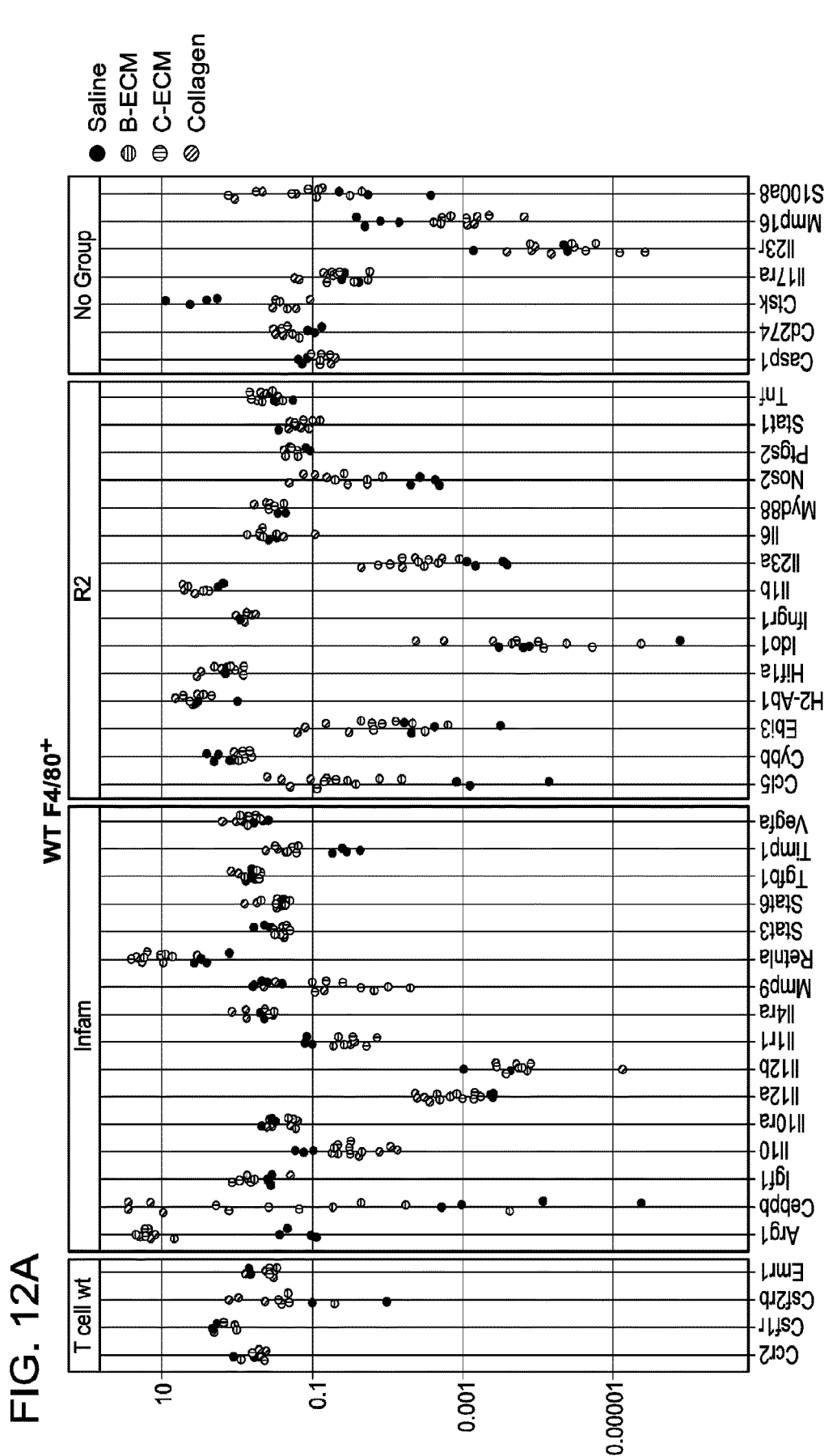
FIGS. 12A and 12B depict graphs showing data spread of gene expression profiling of cells sorted from 1 week post-surgery muscle defects.
Figure 12B:
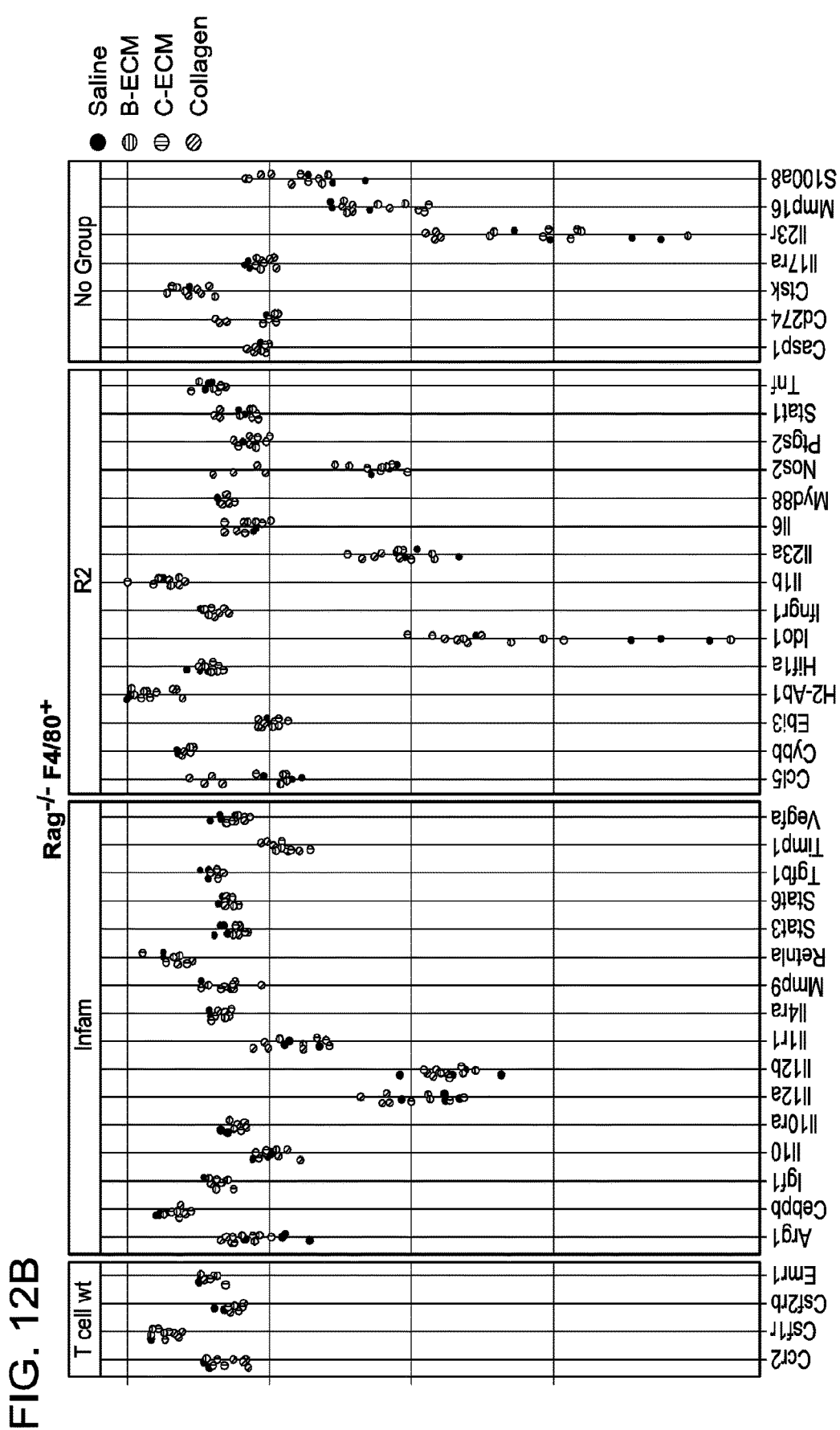
Figure 13A:
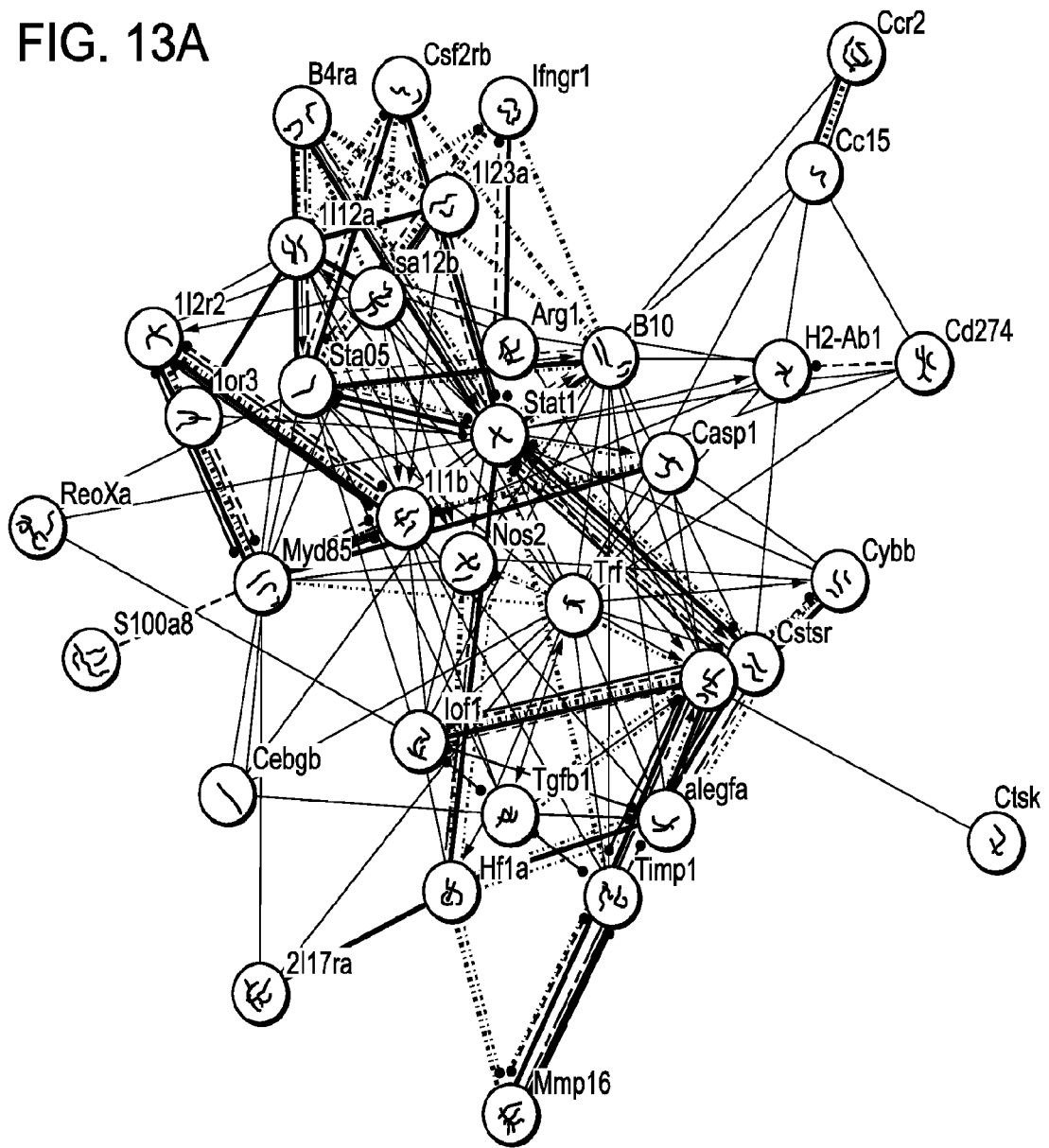
Figure 13C:
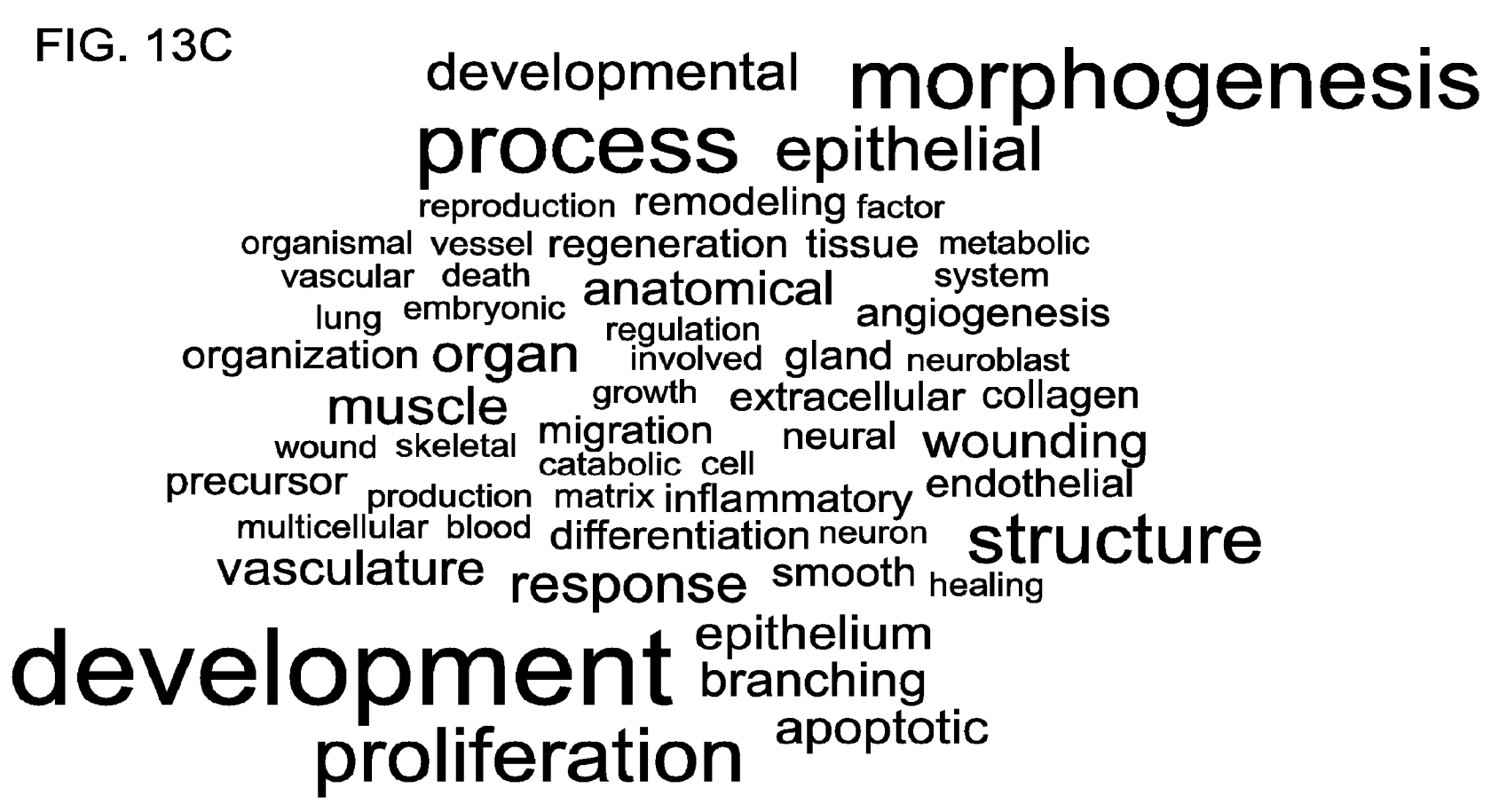
Figure 13D:
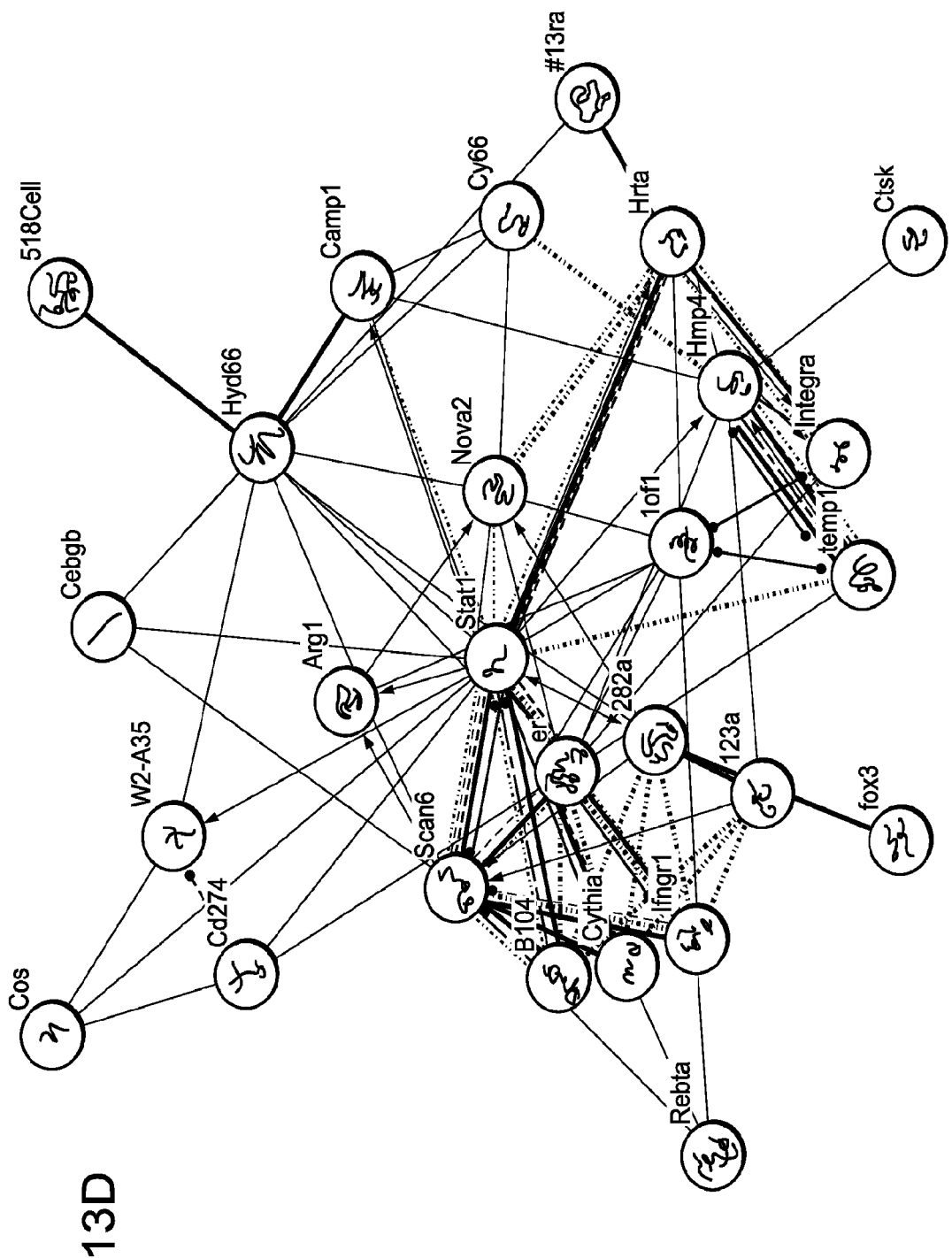
FIG. 13D shows a gene interaction network.

In $Rag^{-/-}$ mice, scaffold-associated macrophages lost their pro-regenerative transcriptome (FIG. 2F; FIGS. 12A and 12B; FIGS. 19A and 19B). As shown in FIG. 1D, virtually all of the observed variability of macrophage gene expression in SIM vs. saline is absent in Rag$^{-/-}$ mice (which cannot mount a Th2 immune response), dramatically demonstrating the critical importance of Th2 adaptive immunity in regulating SIM macrophage M2 polarization. Several genes directly implicated in muscle regeneration such as Igf1 (insulin-like growth factor-1) (F. Mourkioti and N. Rosenthal *Trends Immunol,* 26(10):535-42. (2005); A. Musaro, et al. *Nat Genet,* 27(2):195-200. (2001); and J. P. Liu, et al., *Cell,* 75(1):59-72. (1993)) and Vegfa (vascular endothelial growth factor) (N. Arsic, et al. *Mol Ther,* 10(5): 844-54. (2004)) were significantly decreased in Rag$^{-/-}$ mice (see e.g., FIG. 2F and FIG. 8 and FIGS. 12A and 12B and FIGS. 19A and 19B). Genes that were altered in Rag$^{-/-}$ mice were associated with several developmental and wound healing processes as shown in FIGS. 13A-13F. Additionally, gene ontology enrichment analysis of genes differentially expressed in Rag$^{-/-}$ versus WT macrophages selectively enriches terms associated with morphogenesis and differentiation, suggesting a reliance on the adaptive immune system for up-regulation of developmentally active immune genes (FIGS. 13A-13C).

Example 4: Biomaterial Scaffolds Impact Systemic Immune Homeostasis

Figure 14A:
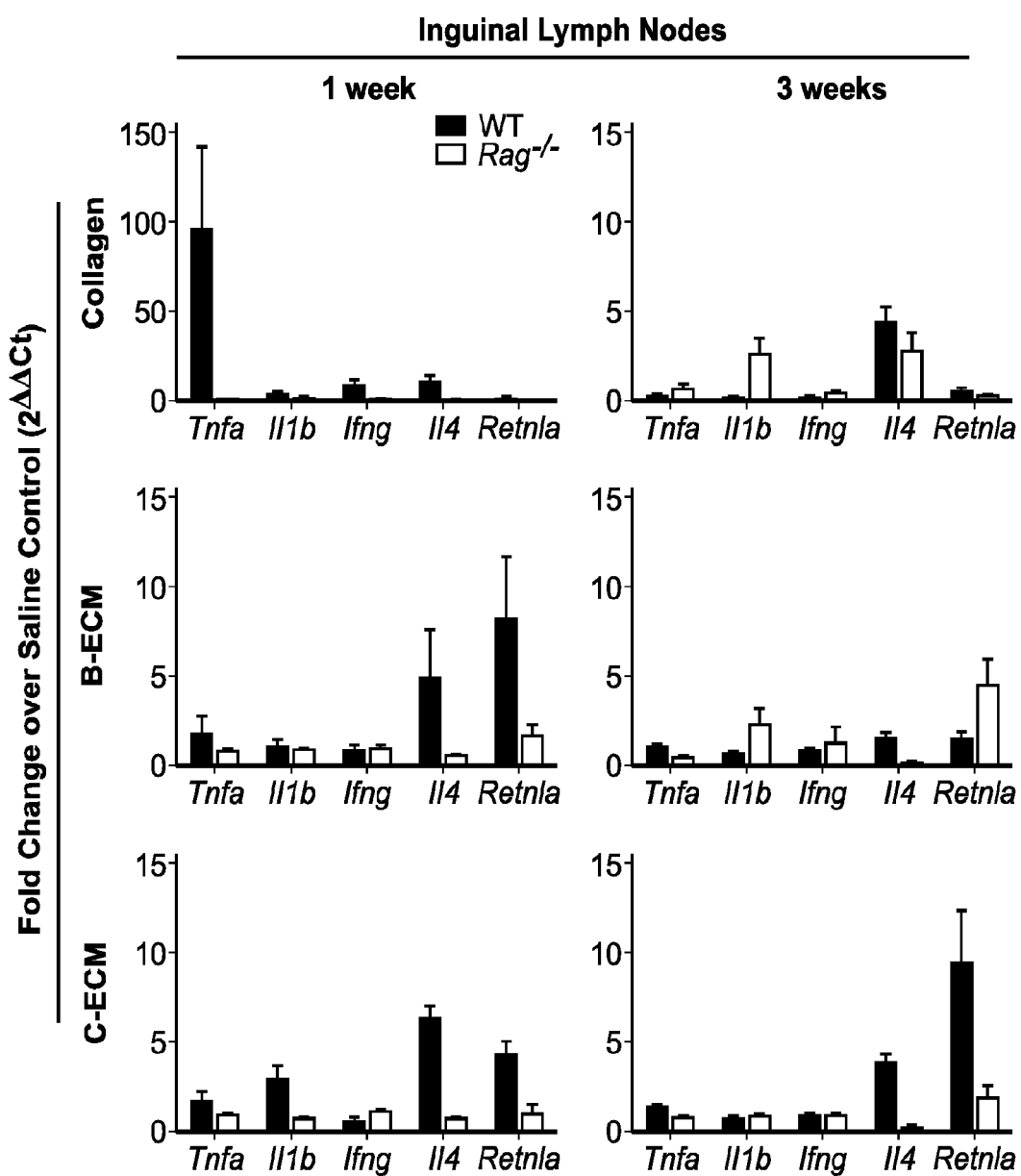
FIGS. 14A-14C: Gene expression in draining lymph nodes at 1 and 3 weeks post-operation. Gene expression was measured in local (FIG. 14A, inguinal) and distal (FIG. 14B, axillary/brachial) lymph nodes at 1 and 3 weeks post-operation to measure type-1 (Tnfa, Il1b, Ifng) and type-2 (Il4, Retnla) gene changes dependent upon scaffold application.
Figures 14B, 14C:
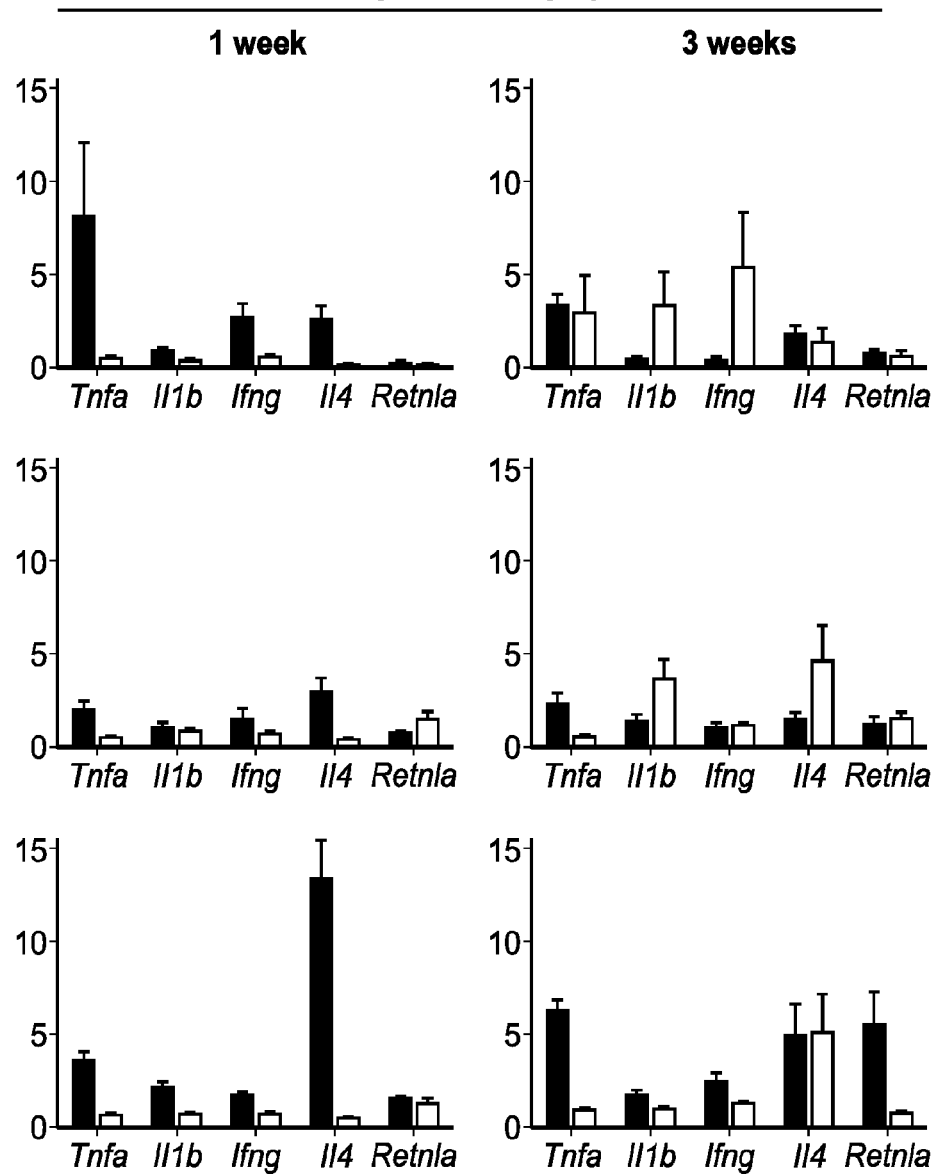

T cell activation and polarization can result in local and systemic alterations of the immune response of an organism. This can lead to immediate effects locally at the injury and implantation site, such as the observed scaffold-mediated CD86 decrease in SAMs (see e.g., FIGS. 2A and 2C). The detection of a local Th2 polarization of the adaptive immune response associated with the presence of M2-type macrophages (see e.g., FIGS. 2A-2I M(IL-4)-type macrophages (FIGS. 2A-2F)) prompted investigation of systemic T cell response in the presence and absence of biomaterial scaffolds (A. J. Allman et al. *Transplantation* 71, 1631-1640 (2001)). As shown in FIGS. 10B-10F, ECM scaffolds skewed the ratio of CD4:CD8 T cells towards a higher fraction of CD4$^+$ cells (~70% in scaffold treated, versus ~50% in saline treated wounds) at 1 week post-operation (see e.g., FIG. 10B). As shown in FIGS. 7A-7D, CD4$^+$ FoxP3$^+$ regulatory T cells were present in low levels at 1 week post surgery and increased over time. To probe the systemic impact of locally implanted biomaterial scaffolds in the traumatic defects, local (inguinal) and distal (axillary/brachial) lymph nodes were characterized (FIGS. 3A and 3B; FIGS. 14A-14C). Scaffold treatment induced hypertrophy of local draining lymph nodes (FIG. 3A) FIG. 3A). This size increase accompanied changes in gene expression, most notably a robust increase in Il4 expression (see e.g., FIG. 3B and FIGS. 14A-14C).

Figure 3A:
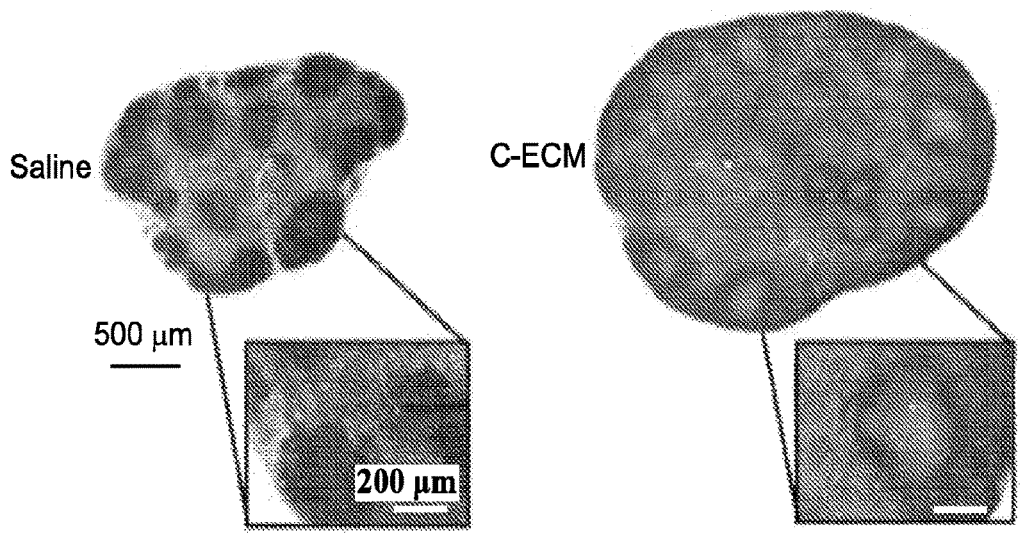
FIGS. 3A and 3B: Systemic immune homeostasis is modified by application of biomaterial scaffolds.
Figure 3B:
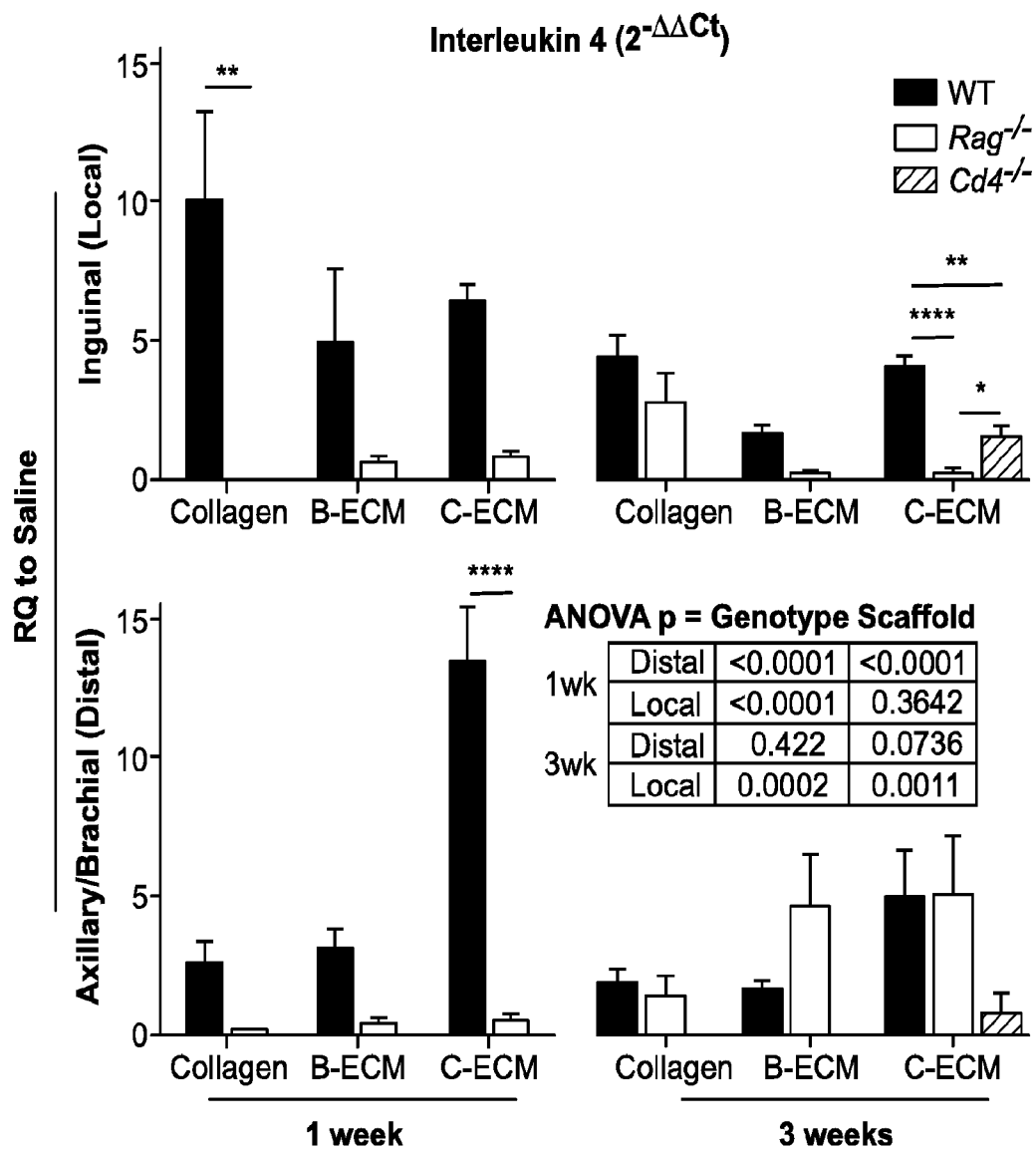

This Il4 induction was absent at 1 week post-operation in Rag$^{-/-}$ mice but present after 3 weeks, suggesting an early adaptive immune-dependent Il4 up-regulation followed by an innate immune driven Il4 up-regulation later in the wound healing and regeneration process. Additionally, Cd4-/- mice displayed a significant decrease in scaffold-mediated Il4 up-regulation in inguinal lymph nodes at 3 weeks post-injury in C-ECM treated animals (FIG. 3B). This Il4 expression level was higher than that of Rag-/- mice, demonstrating an important role of CD4+ helper T cells in scaffold-induced systemic type 2 immunity, but with potential further contributions by B cells or possibly even CD8$^+$ T cells.

The pleiotropic nature of immune responses typically results in complex expression profiles beyond stereotypical M1 versus M2 "poles" often defined by one or two canonical markers in the myeloid population (P. J. Murray et al. *Immunity* 41, 14-20 (2014)). Indeed, the expression levels of CD86 and CD206 on macrophages (M1 versus M2) were not mutually exclusive. Concomitant with Th2 polarization of sorted T cells, scaffold-associated macrophages up-regulated the expression of genes encoding the canonical M2 molecules Arg1 and Retnla (encoding Fizz1), similar to the results from qRT-PCR analyses of the whole wound (including both the biomaterial and surrounding tissue) (FIG. 2E; FIGS. 11A and 11B).

Example 5: Adaptive Immune Cells Mediate the Impact of Scaffold Environment on the Expression of Genes Associated with Increased Muscle Regeneration Il4 is regarded as an integral player in wound healing, recruitment of muscle progenitor cells, and development of mature muscle fibers. It was demonstrated that scaffolds have a direct effect in up-regulating T cell mediated production of Il4 in the wound microenvironment. Cebpb, which is up-regulated in macrophages that infiltrate scaffold-treated wounds (see e.g., FIG. 2F; blue bars), has been associated with macrophage-mediated muscle repair, and its expression is associated with an increase in muscle strength (J. Blackwell, et al. *J Physiol Sci,* 65(1):145-50. (2015)).

Figure 4A:
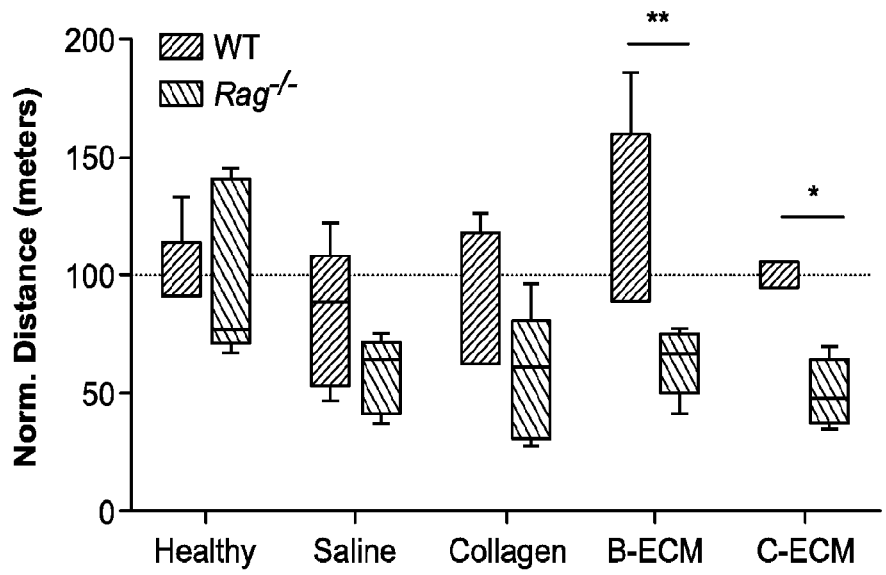
FIGS. 4A-4F: Th2/M(IL-4) responses to biomaterial-treated muscle wound promote functional tissue regeneration.
Figure 4B:
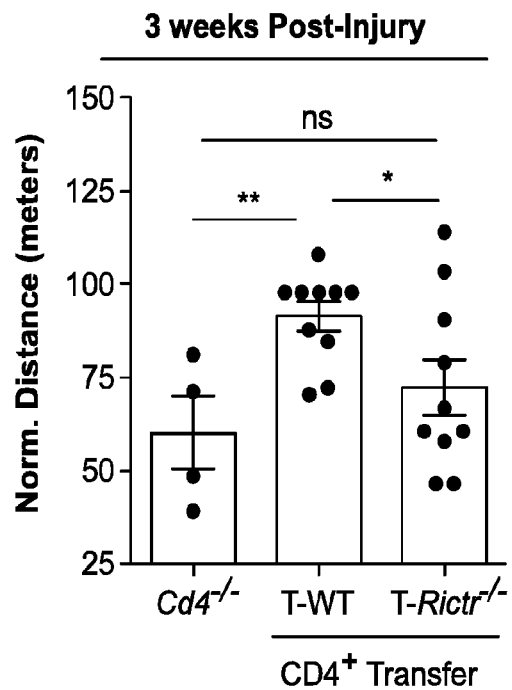
Figure 4C:
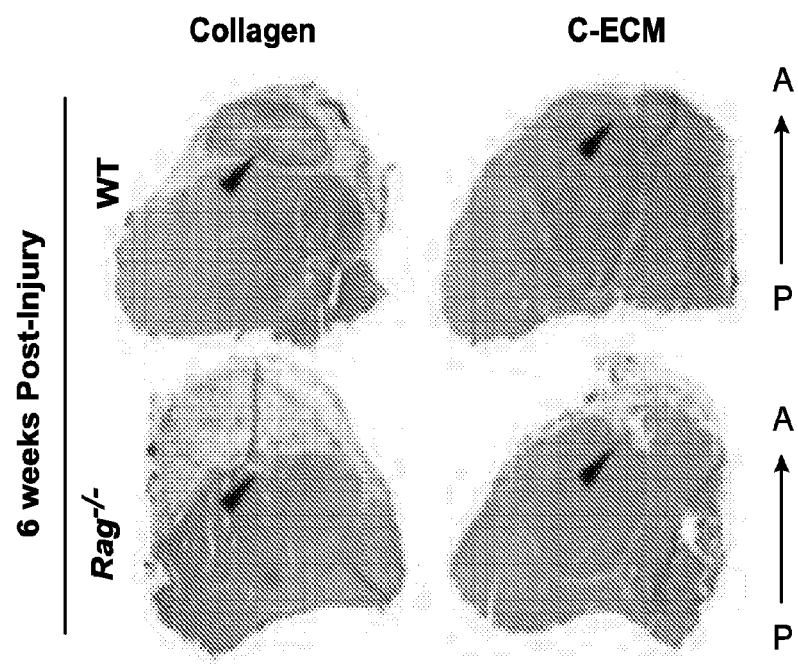
Figure 4D:
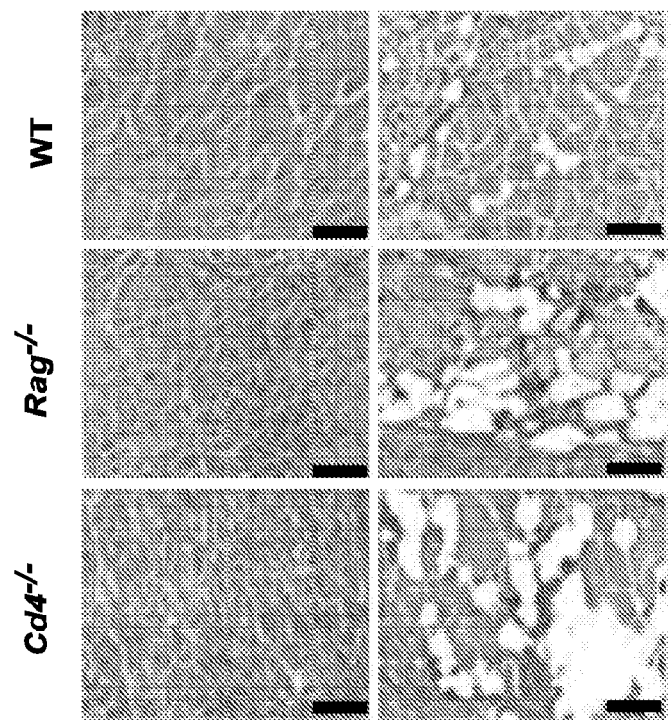
Figure 4E:
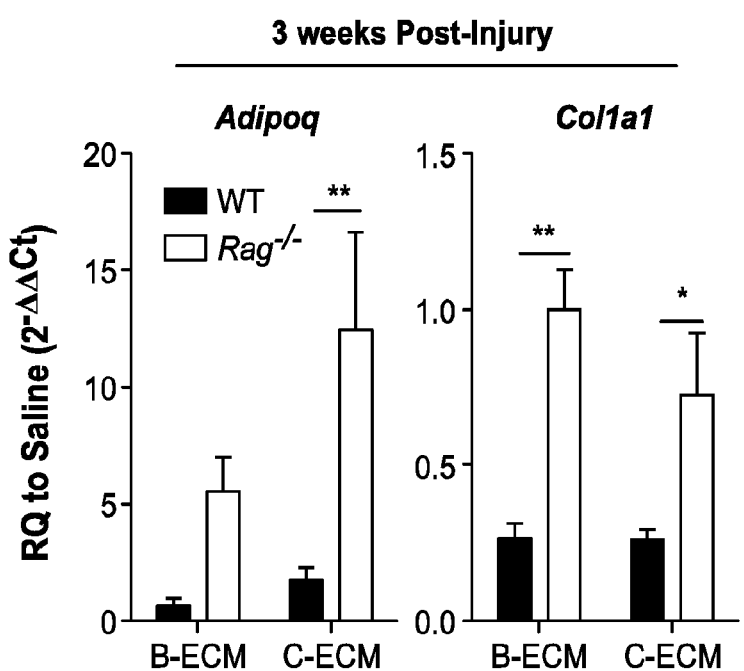

Histologically, it was observed that cellular infiltration occurred around scaffolds and injured regions. Centrally nucleated muscle fibers, which are indicative of active regeneration or recovery from injury, were present within the biomaterial scaffold and around the defect site as shown in FIG. 4D. Notably, the size and morphology of these fibers differed between genotypes—wild type mice presented with larger, more rounded fibers, whereas Rag$^{-/-}$ mice presented with smaller, irregularly shaped fibers, indicating a defect in muscle regeneration. Rag$^{-/-}$ mice also produced increased amounts of adipose tissue within the scaffolds and regenerated muscle, which was observed histologically (see e.g., FIG. 4D) and confirmed by RT-PCR analysis of the whole muscle for AdipoQ (adiponectin), a gene exclusively present in adipose tissue that is associated with fatty acid and glucose metabolism (see e.g., FIG. 4E and FIG. 2B and FIGS. 17A-17E).

Figure 16A:
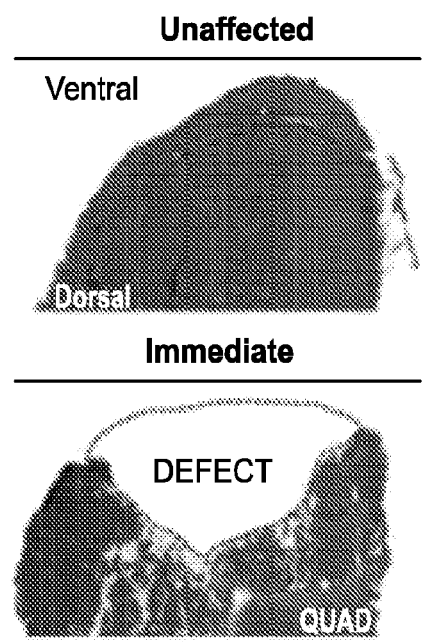
FIGS. 16A-16C: Quadriceps muscle at 3 weeks post-operation in WT and Rag$^{-/-}$ mice.
Figure 16B:
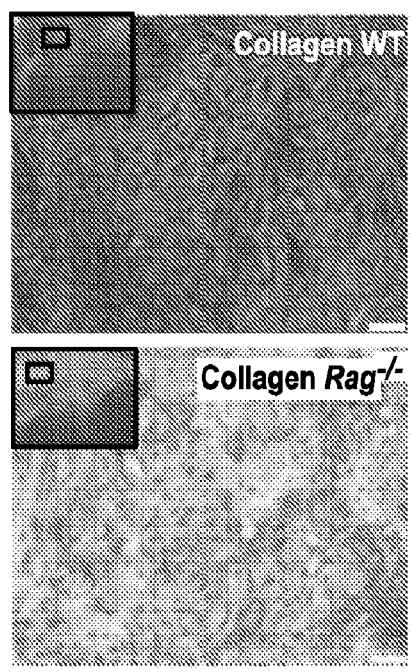
Figure 16C:
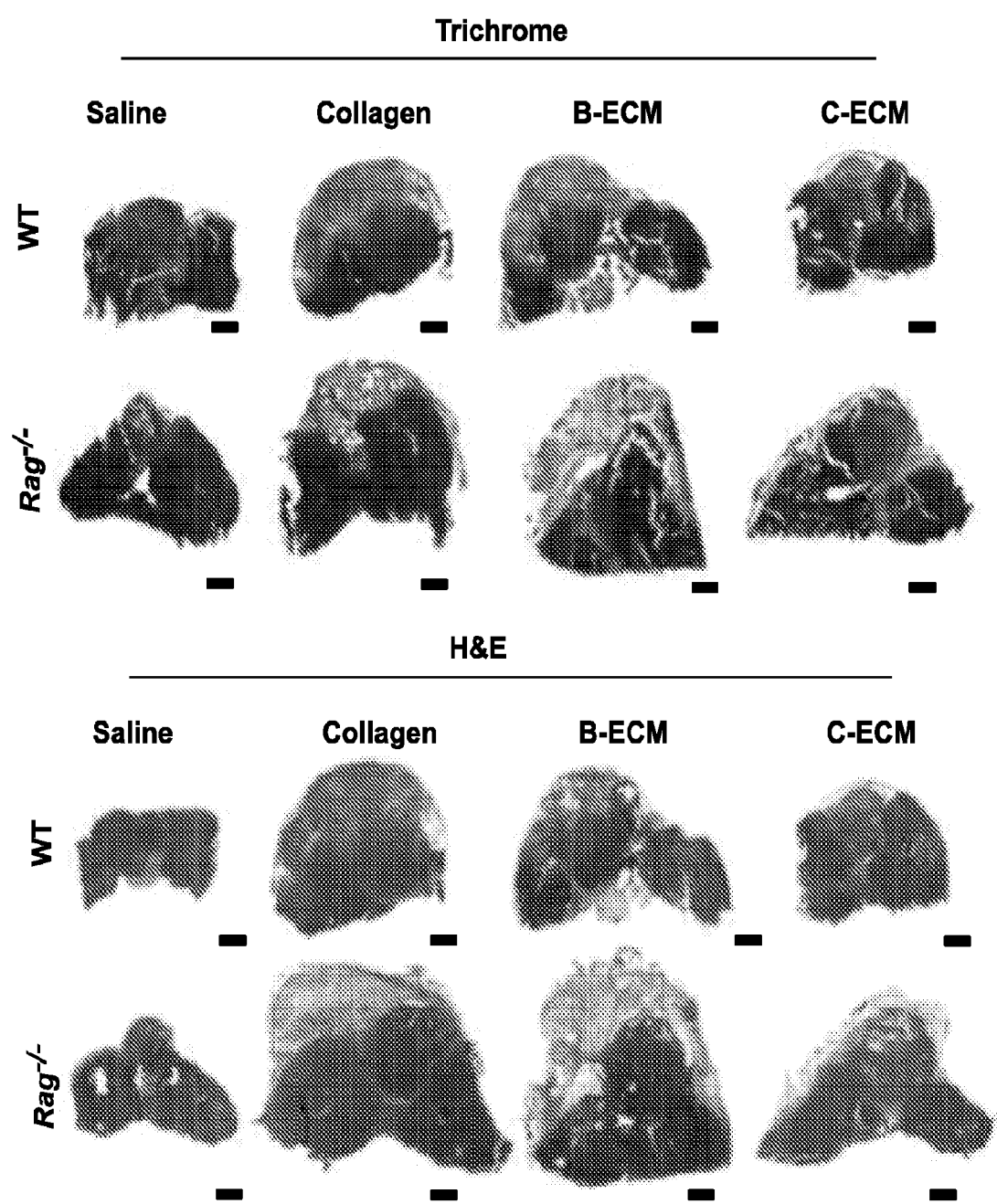
Figure 17A:
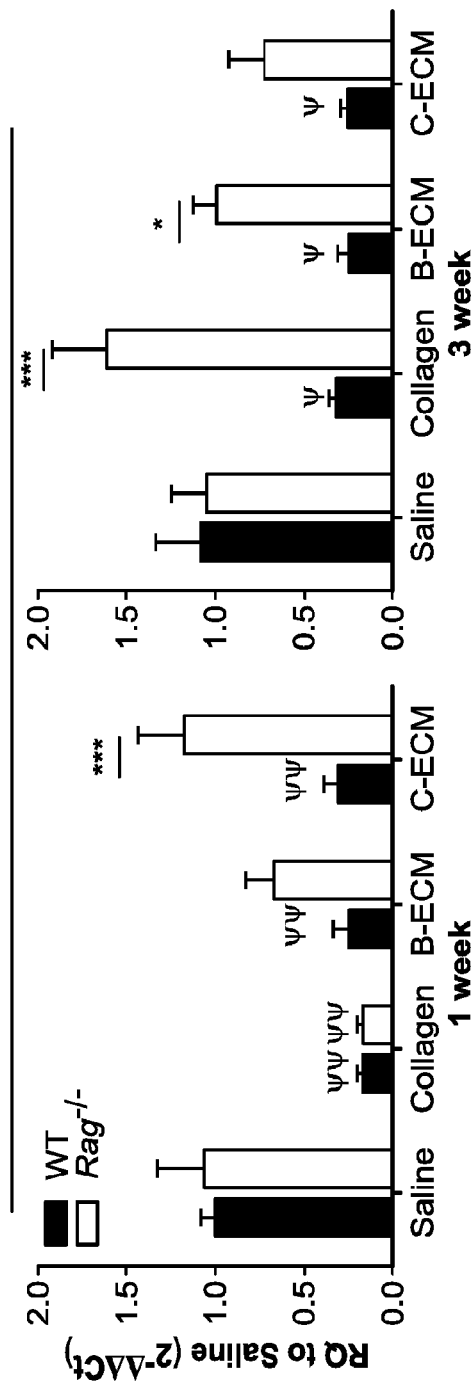
FIGS. 17A-17J: Collagen and adipose-related gene expression increases in Rag$^{-/-}$ mice.
Figure 17B:
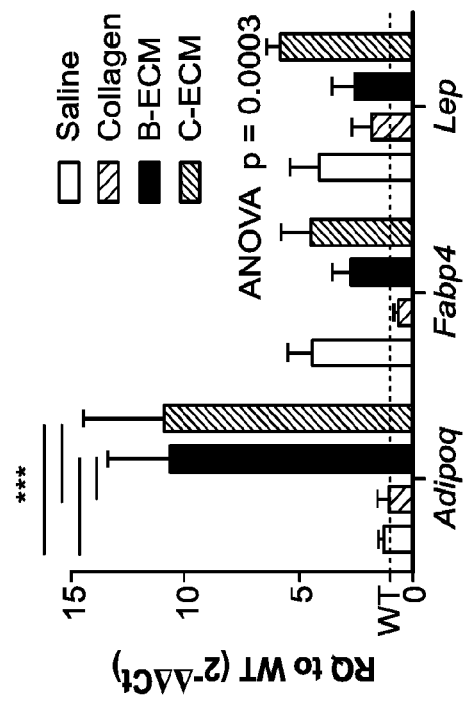
Figure 17C:
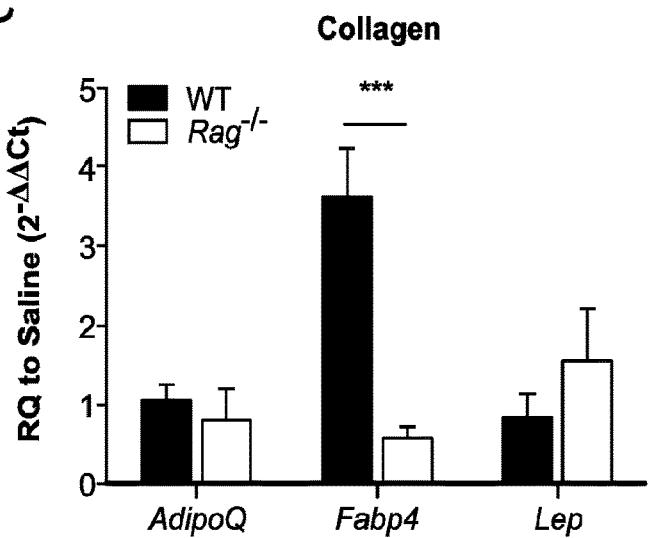
Figure 17D:
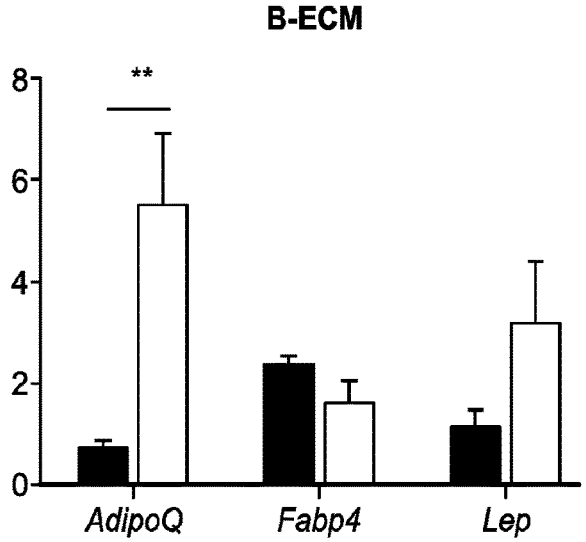
Figure 17E:
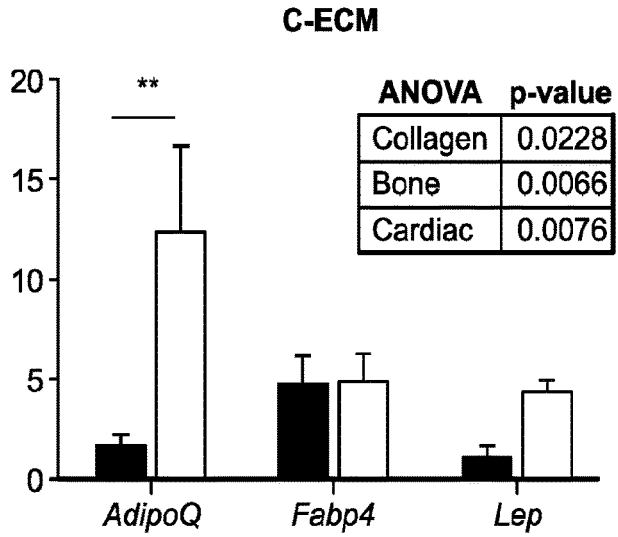
Figure 17F:
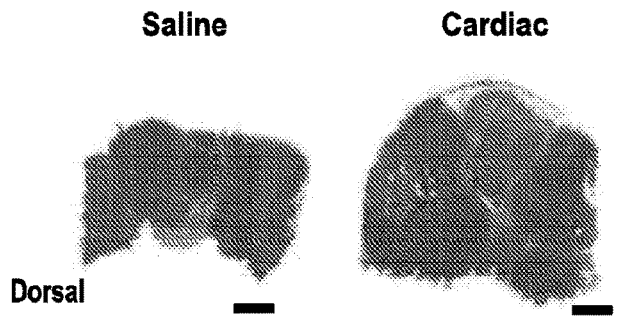
Figure 17G:
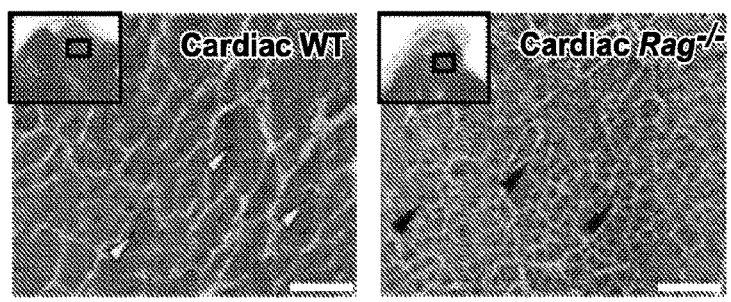
Figure 17H:
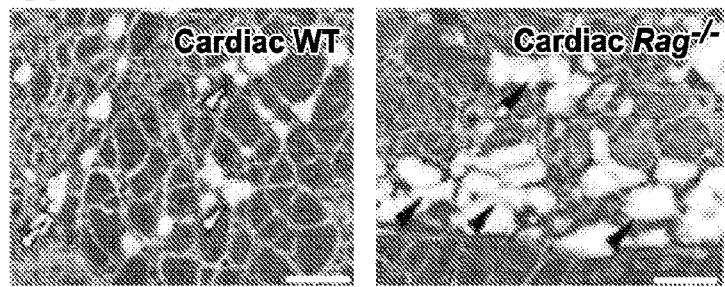
Figure 17I:
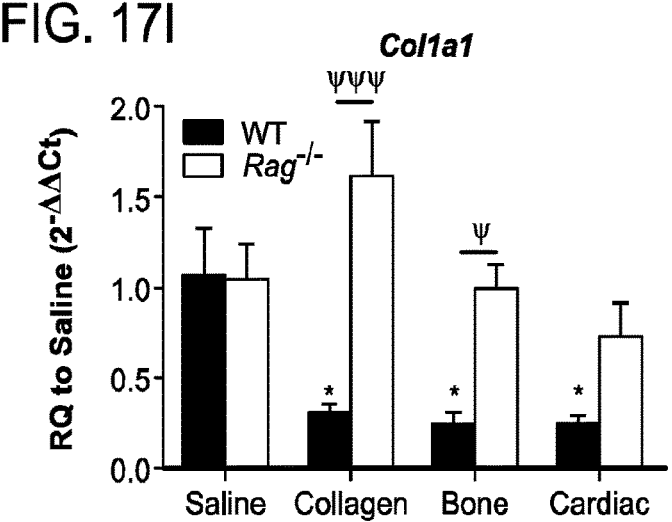
Figure 17J:
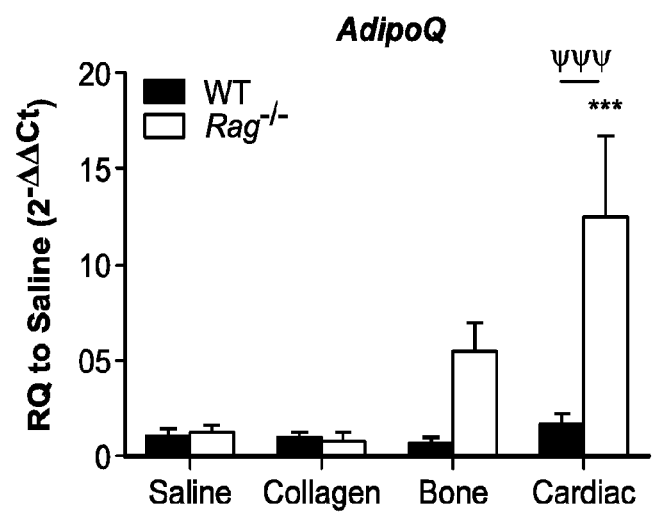
Figure 20A:
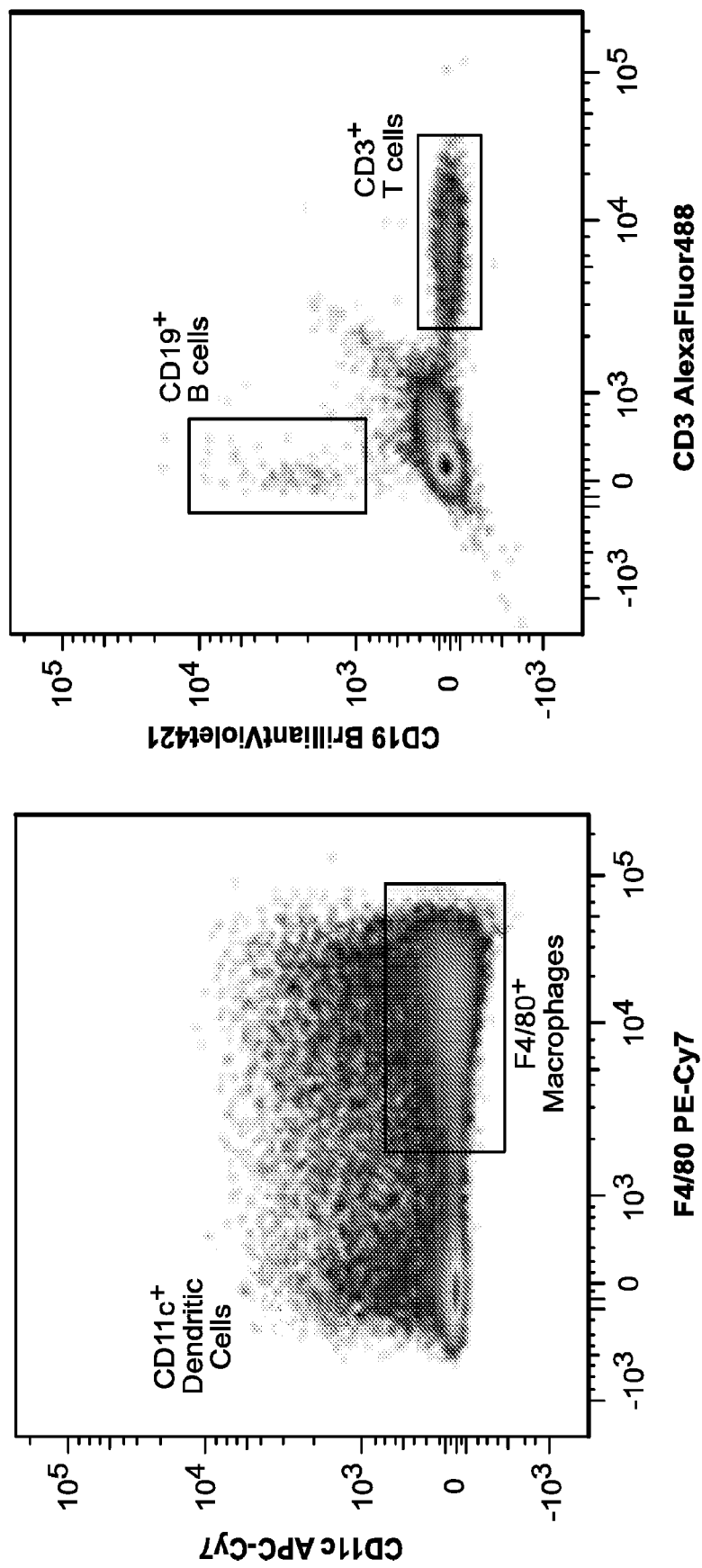
FIGS. 20A-20E: Gating strategies for flow cytometric analyses.
Figure 20B:
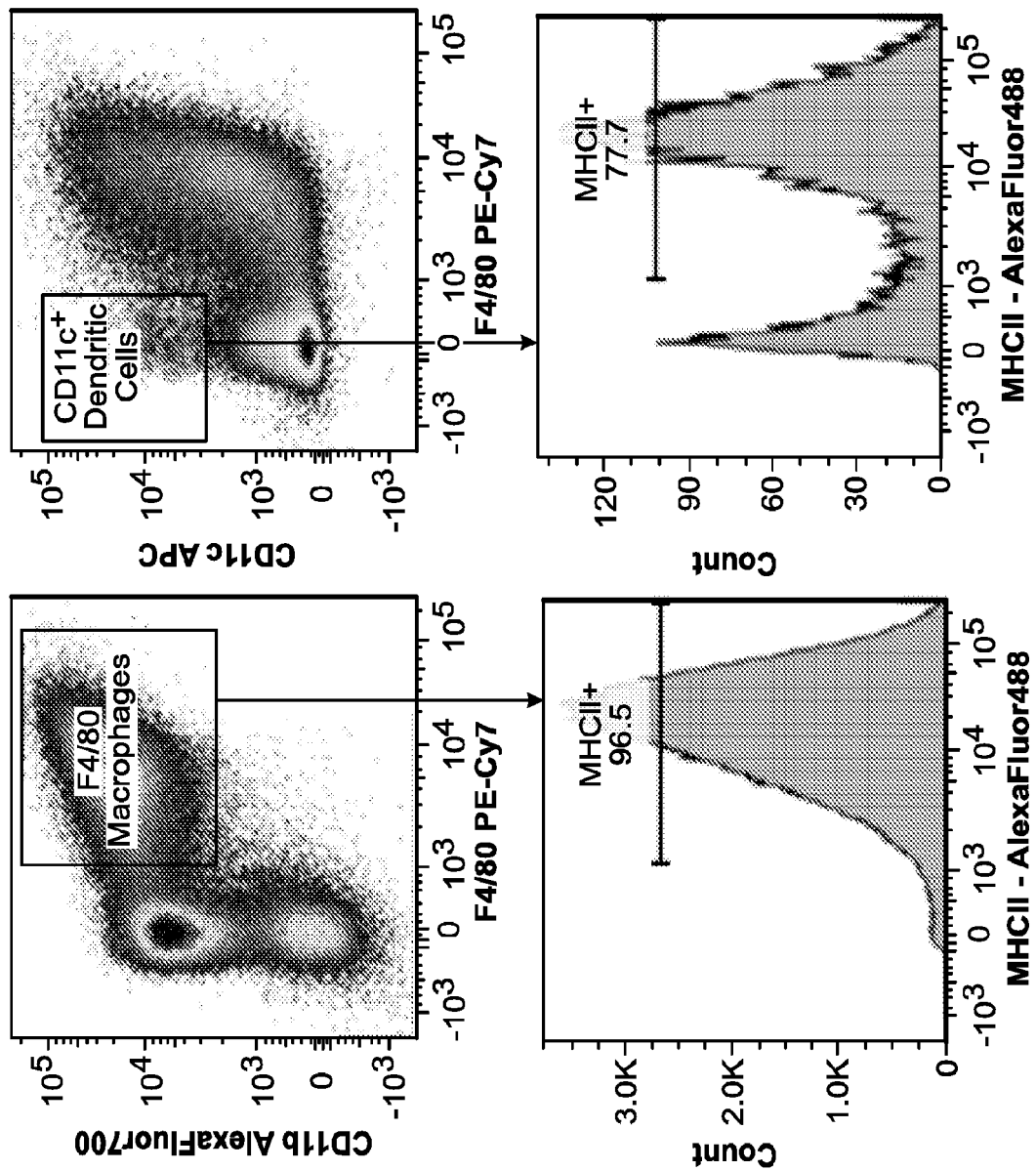
Figure 20C:
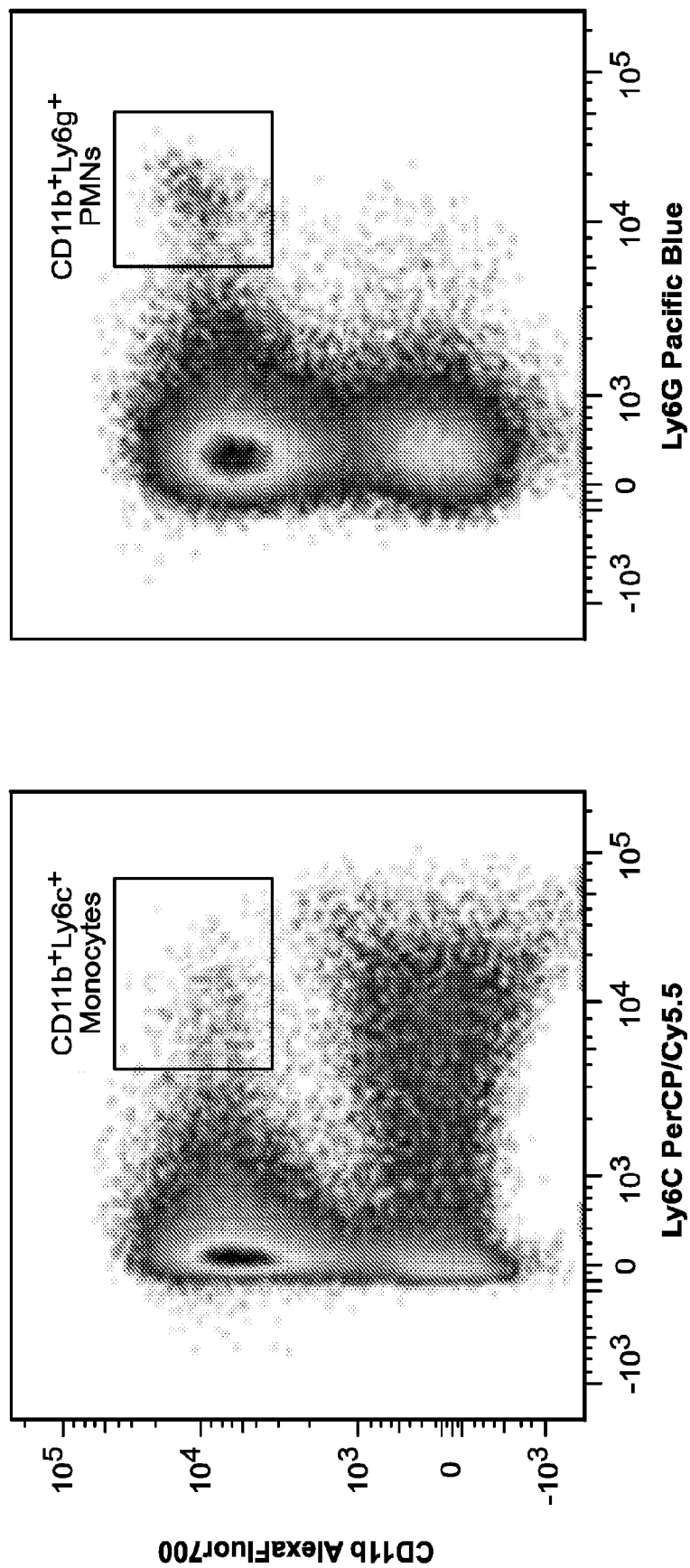
Figure 20D:
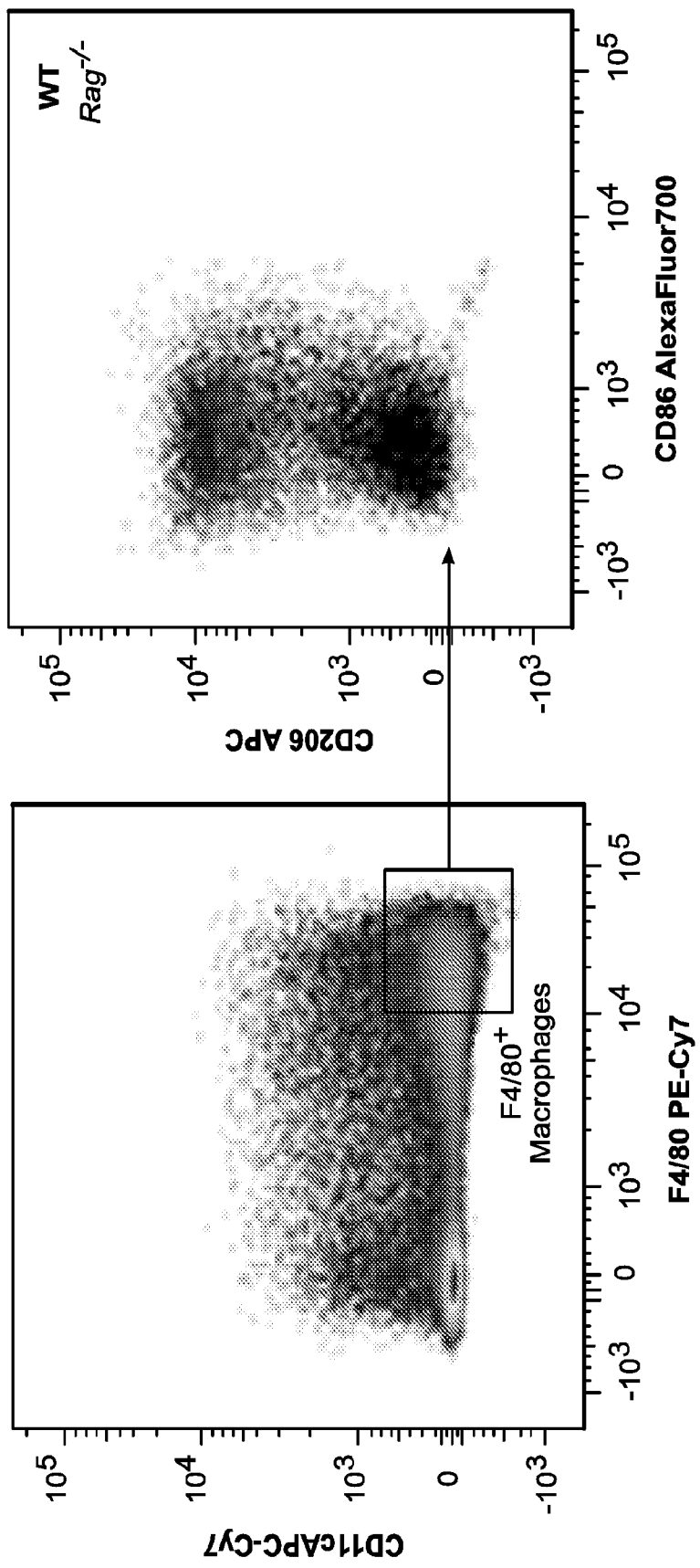
Figure 20E:
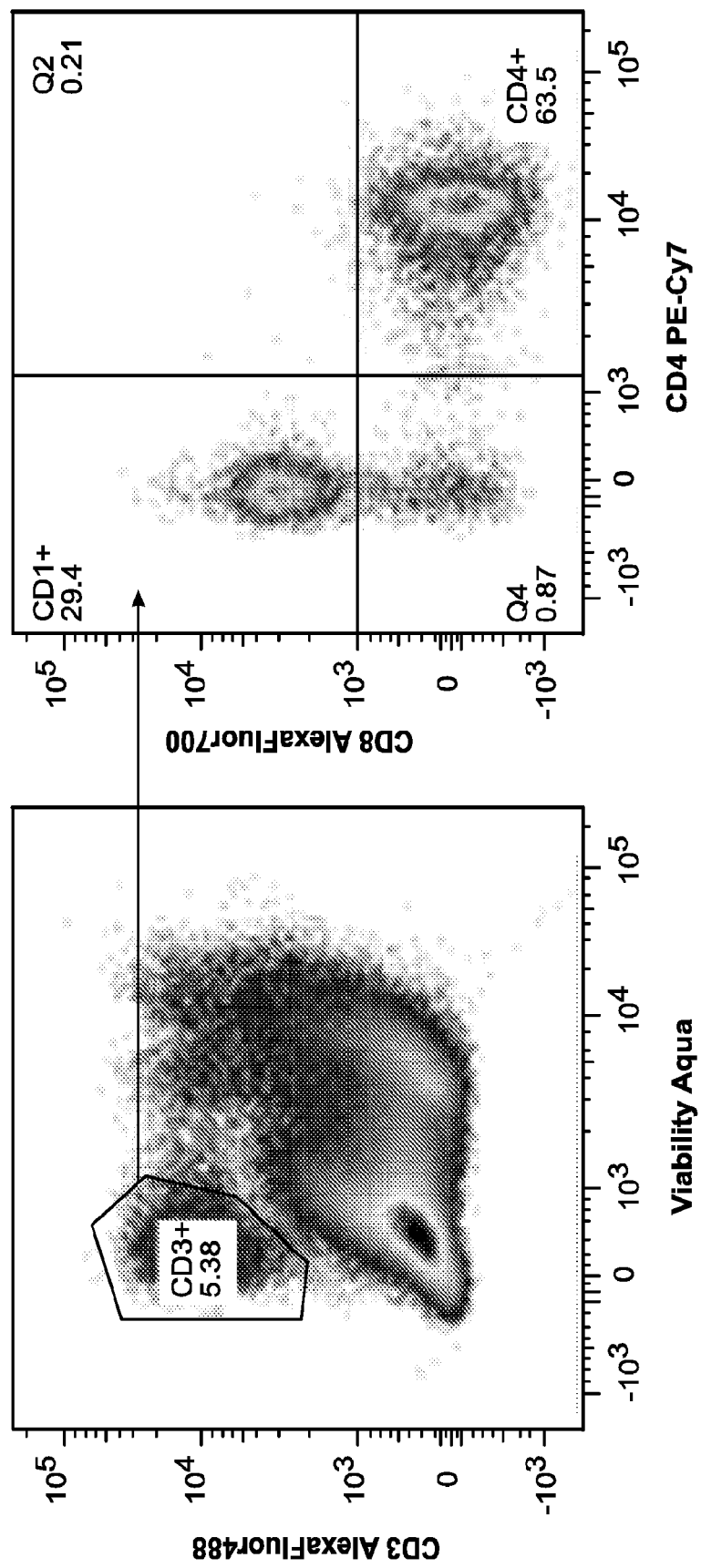

To further characterize the balance of adiposity and fibrosis within the wound region, Type I Collagen gene expression was also measured. Extracellular matrix treatment decreased the expression of Col1a1 (Collagen I) in the wound environment at 1 and 3 weeks post surgery (see e.g., FIG. 4E and FIG. 17A) and this effect was lost in Rag$^{-/-}$ mice, again demonstrating the importance of adaptive immunity. Type I Collagen is a major component of scars; despite reports that type-2 immune polarization can enhance scar formation, the effects of tissue ECM treatment decreased scar formation. Early in the repair process at 1 week post surgery, the collagen scaffold prevents Col1a1 up-regulation even in absence of adaptive immune cells. However, by 3 weeks gene expression increases similarly to the tissue ECM scaffolds. Histologically, a denser fibrous tissue with reduced cellular infiltration developed in Rag$^{-/-}$ mice treated with collagen scaffold compared to the WT collagen animals as shown in FIG. 16B. This displays a direct effect of both scaffold treatment and adaptive immune cells on wound healing and regeneration.

Example 6: T Cells Enable Robust M2-Macrophage Polarization in Scaffold-Treated Muscle Wounds As discussed above, immune cells are the first responders to tissue damage and biomaterial implantation. The various cells of the immune system interact with the scaffold and surrounding environment to create a regenerative immune microenvironment that can dictate polarization and differentiation of stem cells, ultimately determining the regenerative success of a scaffold that is used.

According to the techniques herein, wild type (WT) C57BL/6 and B6.129S7-Rag1$^{tm1Mom}$/J (Rag$^{-/-}$; lack mature T and B cells) mice received bilateral volumetric muscle wounds in their quadriceps femoris muscle. The resulting wounds were treated with saline, particulate extracellular matrix (ECM) scaffolds (bone and cardiac muscle-derived), or particulate bovine collagen. After 1 and 3 weeks, the injuries were analyzed via multicolor flow cytometry to quantify immune cell infiltration and polarization. Proximal (inguinal) and distal (axillary/brachial) lymph nodes were harvested for gene expression analysis.

Figure 21:
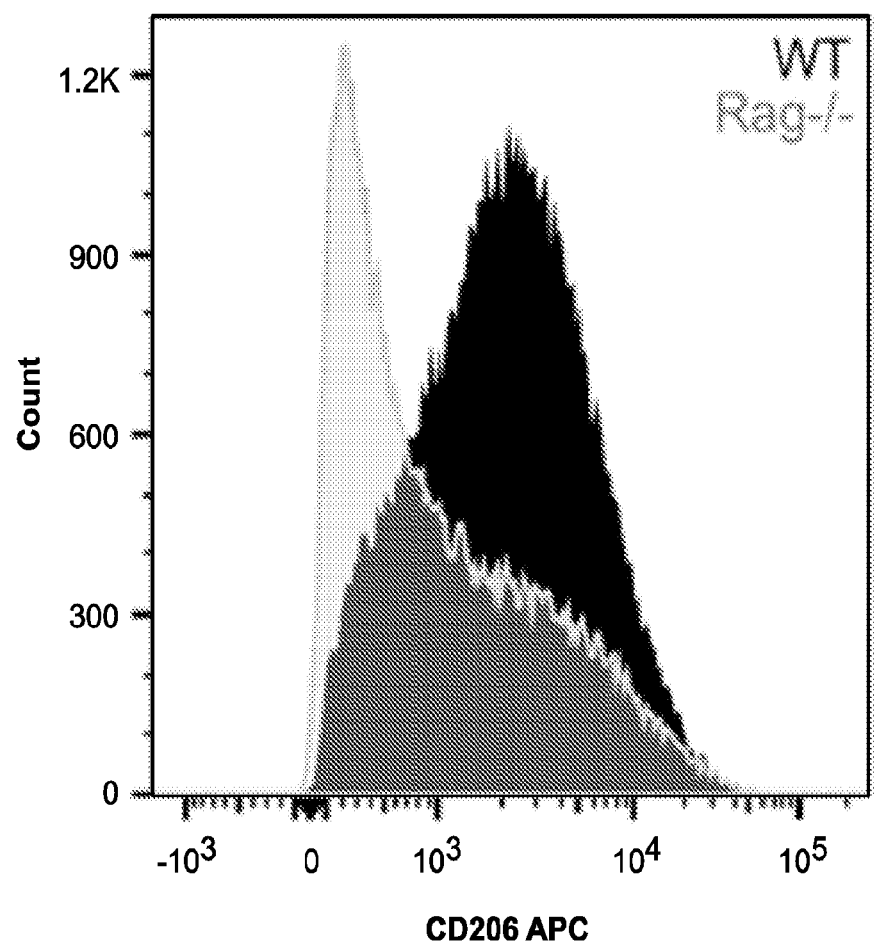
FIG. 21 is an image of a FACS histogram that shows that macrophage polarization is diminished in absence of T cells. FACS histogram of F4/80$^+$ macrophages shows Rag$^{-/-}$ mice with collagen-treated muscle wounds have decreased CD206 expression (M2-polarization).
Figure 22A:
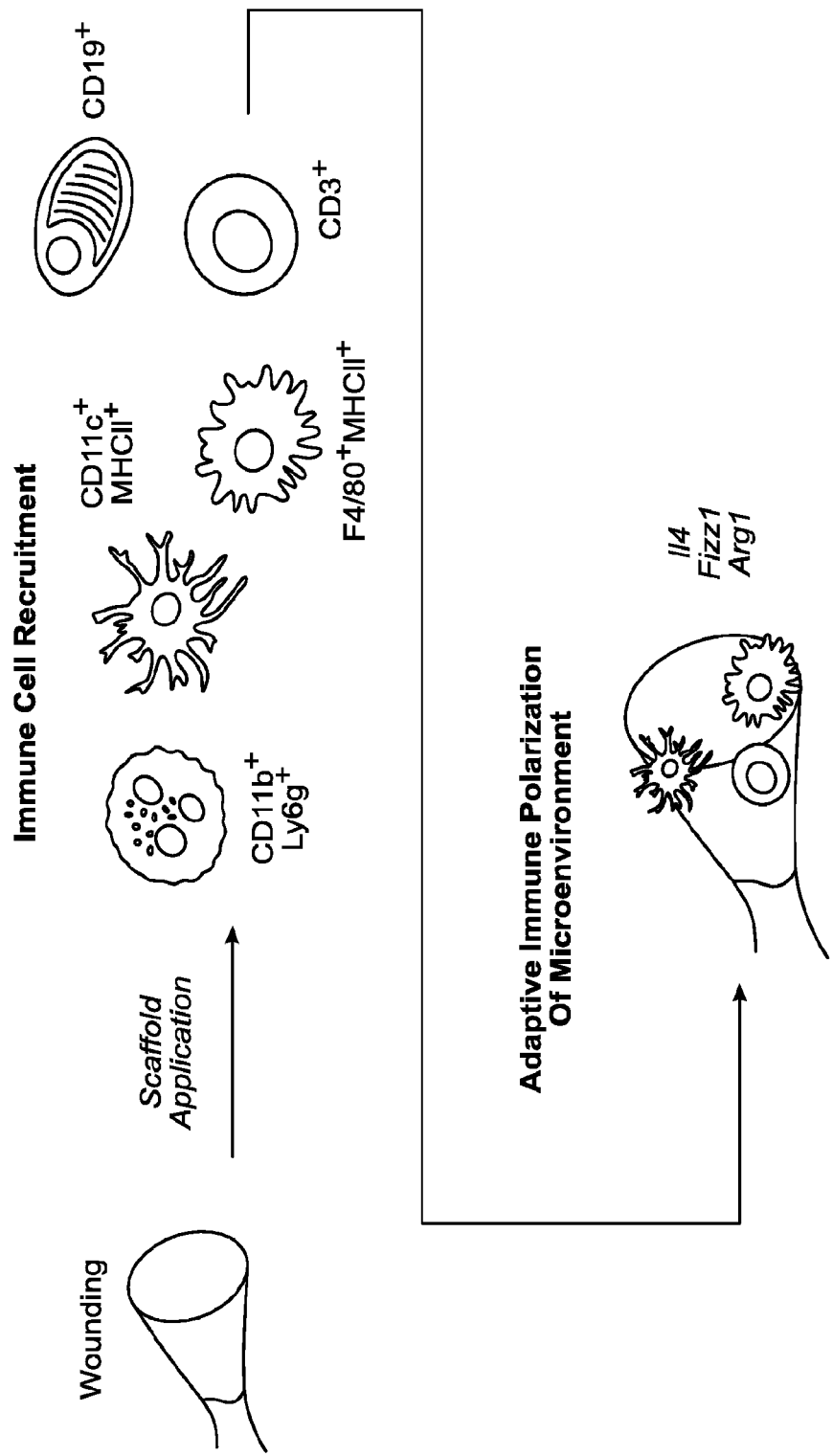
FIG. 22A shows schematic depicting immune cell recruitment and polarization in scaffold-treated muscle wounds.
Figure 22B:
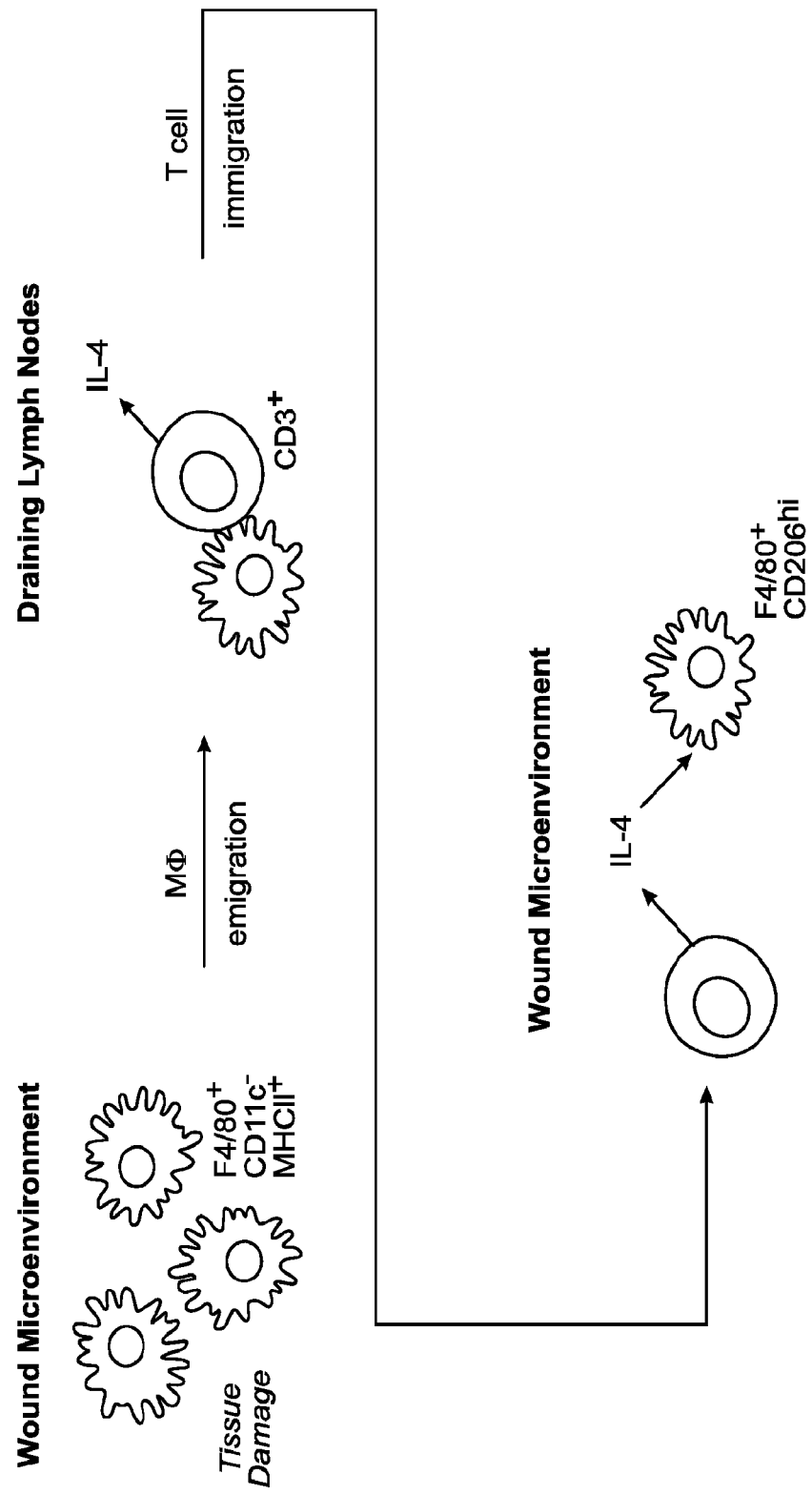
FIG. 22B shows myeloid emigration from local tissue microenvironment accompanies T cell activation in draining lymph nodes leading to increase in type-2 immune phenotype including Il4 gene expression both locally (wound) and systemically (lymph nodes).

The largest population of immune cells in muscle wounds was detected at 1 week post-operation, with scaffold-treated wounds recruiting more cells than the control saline treated muscles. In wild type mice, it was observed that infiltration of myeloid (F4/80$^+$, CD11c$^+$, CD11c$^+$F4/80$^+$) and lymphoid (CD3$^+$CD4$^+$, CD3$^+$CD8$^+$, CD19$^+$) immune cells. As shown in FIG. 21, scaffold treated wounds displayed slightly increased CD206 (M2) expression than saline treated animals, and at 3 weeks showed significantly lower CD86 (M1) expression. In Rag$^{-/-}$ mice a decrease in CD206 was observed at 1 and 3 weeks post-operation in all wounds, and an increase in CD86 at 3 weeks post operation in scaffold-treated wounds leading to ablation of the CD86 decrease seen in wild type mice. As shown in FIG. 21, there was also note robust up-regulation of 11-4 and Fizz1 in distal (axillary/brachial) local (inguinal) draining lymph nodes of scaffold-treated wounds that is ablated in Rag$^{-/-}$ mice.

Muscle wounds recruit various myeloid and lymphoid cells such as macrophages, dendritic cells, T cells and B cells. Overall cellular recruitment increases upon treatment with an ECM scaffold, which increases the presence of M2-macrophages. Presence of CD4$^+$ and CD8$^+$ T cells suggested interaction of these macrophages with the adaptive immune system. In absence of T cells (Rag$^{-/-}$) macrophages to not reach complete M2-polarization as measured by CD206 expression. Accordingly, formation of the local and systemic immune microenvironment of ECM scaffold-treated muscle wounds is mediated by integration of signals from the surrounding environment and cooperative signals from both the innate and adaptive immune responses.

Example 7: Immune Profiles of Particulate ECM Scaffolds in Volumetric Muscle Wounds As discussed above, the immune system plays a critical role in regeneration, and imbalances in immune polarization can lead to pathologies such as damaging inflammation and scarring. Secreted proteins such as cytokines can also interact with stem cells, altering their growth and differentiation. It was shown that bone-derived and cardiac muscle-derived extracellular matrix (ECM) scaffolds applied to traumatic wounds can alter both local and systemic immune profiles. Overall cellular recruitment to traumatic muscle wounds, which is 45-50% immune cells, increases if treated with particulate ECM as opposed to saline control. Furthermore, via multicolor flow cytometry, three distinct myeloid cell populations were observed within subcutaneous and traumatic wounds that vary in polarization along the M1-M2 axis. All treatment groups showed adaptive immune cell recruitment, specifically CD4+ and CD8+ T cells, suggesting communication with myeloid cells within the wound microenvironment. Systemically, it was noted that gene expression changes in both proximal and distal lymph nodes with upregulation of Il4 in scaffold treated wounds at both 1 and 3 weeks post-operation. These phenotypes, both local and systemic, depend upon scaffold tissue source and evolve over time.

The results described herein show that scaffolds recruit immune cells with a complex polarization profile in muscle wounds and a previously undescribed systemic response. These immune responses can be modulated with application of ECM scaffolds derived from different tissues.

According to the techniques herein, biomaterial scaffolds may be used in regenerative medicine to support the growth and differentiation of cells to create aesthetic and functional replacements for missing or damaged tissue. Upon implantation, biomaterials are generally designed to support the growth of stem and progenitor cells, and to provide biological signals that stimulate tissue growth. Similarly, implanted biomaterials interact with immune cells, and consequently scaffold design is expected to impact the immune environment (i.e. SIM) by providing proteins orchestrating tissue regeneration.

Resident immune cells in a tissue can quickly respond and are the key factors that create a Th2 regenerative environment (S. J. Jenkins, et al., Science, 332(6035): 1284-8. (2011)). Since biomaterial scaffolds essentially create an artificial local microenvironment, they can be readily applied as a tool to increase both the number of immune cells and promote a specific desired functionality in tissues. This SIM can therefore be influenced by the trauma, disease or tissue type in which the material is implanted, and can be manipulated through the biophysical composition and properties of the biomaterial itself. In one of the few examples of biomaterial implant-mediated immune modulation, Mooney et al. leveraged both sponges and hydrogels to educate dendritic cells for cancer treatment (J. Kim and D. J. Mooney, Nano Today, 6(5):466-77. (2011) and O. A. Ali, et al., Cancer Res, 74(6):1670-81. (2014)). The biomaterials used in this study provided inflammatory signals to mediate anti-tumor responses from the adaptive immune system (O. A. Ali, et al. Adv Funct Mater, 23(36):4621-8. (2013)). In addition to biological or chemical cues in the scaffold, biomechanics of the implanted material and even local tissue can influence cell response (D. E. Discher, et al. Science, 324(5935):1673-7. (2009) and A. J. Engler, et al. Cell, 126(4):677-89. (2006)).

Macrophage polarization along the M1-M2 (pro-inflammatory/anti-inflammatory) axis in response to biomaterials has been appreciated as a contributor to regenerative outcomes (B. N. Brown, et al. Biomaterials, 33(15):3792-802. (2012) and B. N. Brown, et al. Front Immunol, 5:510. (2014)), and has been studied in the case of extracellular matrix (ECM) scaffolds. ECM scaffolds induce a local type-2 (M2) macrophage polarization in muscle wounds and also diminish the strong type-1 (M1) response to synthetic materials (D. M. Faulk, et al. Biomaterials, 35(30):8585-95. (2014) and M. T. Wolf, et al. J Biomed Mater Res A, 102(1):234-46. (2014)). This M2 polarization of the immune response is also associated with poor prognosis in cancer progression and fibrotic disease, but positive outcomes in wound healing and regeneration (W. C. Gause, et al., Nat Rev Immunol, 13(8):607-14. (2013)). Thus, there is a delicate balance of immune polarization that mediates homeostasis and disease, which can potentially be manipulated with biomaterials.

Systemic immune responses may also influence the repair and regeneration process. For example, trauma associated with hip replacement surgery induces significant systemic immunological changes that can impact the recovery time from surgical intervention (B. Gaudilliere, et al. *Sci Transl Med*, 6(255):255ra131. (2014)). Immune signatures (Stat3, Creb and NF-Kb signaling) associated with a CD14+ monocyte subset predicted delayed functional impairment and pain. In another clinical example, non-healing bone fractures were associated with terminally differentiated memory CD8+ T Cells found in the peripheral blood. These memory cells were not related to the acute trauma of the bone fracture but to lifelong antigen exposure (S. Reinke, et al. *Sci Transl Med*, 5(177): 177ra36. (2013)). However in preclinical modeling of the clinical observations, a specific T cell subpopulation (CD8+ effector memory cell population) was found in early fracture hematomas where they secreted factors that negatively impacted bone healing. However, as described herein, CD8+ cytotoxic T lymphocyte recruitment was decreased upon scaffold implantation in volumetric muscle wounds with a pro-regenerative environment indicating that the presence and absence of certain immune cells are important positive and negative regulators of regenerative success. The results described herein indicate that the local and systemic immune environments cooperate to define the regenerative response to tissue damage.

Immune cells are directly implicated as necessary participants in wound healing and tissue regeneration. Removal of macrophages by clodronate liposome depletion in salamanders completely inhibited limb regrowth after amputation (J. W. Godwin, et al. *Proc Natl Acad Sci US A*, 110(23):9415-20. (2013)). In mouse models, depletion of Cebpb (an important transcription factor mediating M2-macrophage polarization) (D. Ruffell, et al., *Proc Natl Acad Sci USA*, 106(41):17475-80. (2009)) and Il4ra (alpha-chain receptor for IL-4; prevents IL-4/IL-13 signaling) resulted in significant impairment of myogenic recovery of cardiotoxin-injured murine hindlimb muscles. This Il4ra knockdown-mediated impairment also correlated with increased adipogenesis, demonstrating the importance of IL-4 in reducing fibro-adipocyte progenitor cells from excessive adipose deposition. The balance of adipogenesis, myogenesis and fibrosis in muscle repair is delicate as there is also evidence for the importance of adipose tissue in wound healing. Surgical transplantation of adipose grafts and lipoaspirate stimulates healing and reduces scarring in burn, skin, and even bone tissues (G. Rigotti, et al. *Plast Reconstr Surg*, 119(5):1409-22; discussion 1423-4. (2007); M. Nambu, et al., *Ann Plast Surg*, 62(3):317-21. (2009); M. Klinger, et al. *Aesthetic Plast Surg*, 32(3):465-9. (2008); and C. M. Cowan, et al. *Nat Biotechnol*, 22(5):560-7. (2004)). In addition to alterations in adipogenesis, IL-4 is directly related to muscle development. IL-4 is a signal for myotube fusion through an NFAT2c-dependent signaling mechanism in myoblasts (V. Horsley, et al. *Cell*, 113(4):483-94. (2003)). Rag$^{-/-}$ mice display smaller regenerating muscle fibers during injury, suggesting an inhibition of myotube fusion due to the decreased presence of IL-4.

According to the techniques herein, adaptive immune cells in local and systemic immune polarization in scaffold-treated muscle wounds may be combined with next generation biomaterial implant immunotherapies. Current cancer immunotherapies are focused on the modulation of T cell responses to direct immune polarization to promote cancer clearance (S. A. Rosenberg, et al. *Nat Med*, 10(9):909-15. (2004)). Just as cancer research has made great strides in T cell therapies, these concepts can be translated to biomaterials design. Currently, through use of nanoparticle therapies, immunologists have been able to control various T cell responses to promote anti-tumor immune responses (D. J. Irvine, et al. *Chem Rev*. (2015) and N. K. Mehta, et al. *Cancer Immunol Res*. (2015)). Combining the fields of cancer immunotherapy with biomaterial scaffolds according to the techniques herein may open a new avenue for promoting tissue repair through T cell manipulation and regenerative immunology.

Example 8: Role of CD4+ T Cells (Th2 T Cells) on Polarization of Myeloid Cells

To further elucidate the role of CD4+ T cells, and more specifically Th2 T cells on polarization of myeloid cells, myeloid CD206 expression in Rag$^{-/-}$ mice that were repopulated with either WT CD4+ T cells or Rictor$^{-/-}$ CD4+ T cells (FIGS. 2C-2D; FIGS. 11A-11C) were evaluated. Rictor is a critical component of the mTORC2 complex that integrates signals from the environment and drives the polarization of Th2 cells (G. M. Delgoffe et al. *Nature immunology* 12, 295-303 (2011)). Thus, Rictor deletion in T cells selectively prevents Th2 polarization, while preserving differentiation along Th1 and Th17 pathways. Myeloid cells in Rag$^{-/-}$ mice expressed lower levels of CD206 compared to WT mice; however, when repopulated with WT CD4+ T cells (T-WT), this phenotype was rescued. When mice received Th2-deficient T cells (T-Rictr$^{-/-}$), CD206 expression was not rescued, proving that Th2 T cells, dependent upon mTORC2 signaling, are necessary for pro-regenerative myeloid polarization in the scaffold associated immune microenvironment. To confirm the role of IL-4 in Th2-dependent myeloid polarization, the M1/M2 phenotype was evaluated in BALB/c-Il4ra$^{tm1Sz}$/J (Il4ra$^{-/-}$) mice that lack the common receptor chain for IL-4 and IL-13, and thus cannot receive signals from IL-4 (FIGS. 2C-2D). Compared to WT controls, myeloid cells in Il4ra$^{-/-}$ wounds expressed far lower levels of CD206, suggesting that the M2-polarization was indeed controlled by IL-4, and verifying that the pro-regenerative profile is associated with M(IL-4) cells.

Example 9: Gene Expression in Scaffold-Treated Muscle Wounds

The regenerative outcome of tissue-derived ECM scaffolds in animals and humans is correlated with an M2 macrophage phenotype during remodeling (B. M. Sicari et al. *Science translational medicine* 6, 234ra258 (2014), V. J. Mase, Jr. et al. *Orthopedics* 33, 511 (2010), and B. N. Brown et al. *Acta biomaterialia* 8, 978-987 (2012)). Biomaterials increased expression of key genes associated with a pro-regenerative type 2 immune response including hallmark genes of M2 myeloid cells, more specifically macrophages that are stimulated by IL-4, known as M(IL-4) macrophages (FIG. 9) (P. J. Murray et al. *Immunity* 41, 14-20 (2014)). Importantly, the expression levels of these genes were seemingly dependent on the presence and type of scaffold. As with Il4 expression, induction of these M(IL-4) markers was almost completely lost in Rag$^{-/-}$ mice, suggesting that adaptive immune cells play a critical role in shaping the pro-regenerative myeloid phenotype (FIG. 9; Rag$^{-/-}$ red bars).

Example 10: Alterations in the Immune Phenotype Correlated with Differential Levels of Tissue Regeneration Evaluated Using a Treadmill Exhaustion Assay To determine if alterations in the immune phenotype correlated with differential levels of tissue regeneration, the overall muscle function in a treadmill exhaustion assay was evaluated. Wildtype animals recovered to run distances similar to healthy uninjured counterparts after 6 weeks (FIG. 4A). However, this restoration in running capacity was ablated in the absence of T and B cells (Rag$^{-/-}$) in ECM scaffold treated wounds. At 3 weeks post-injury, repopulation of Rag$^{-/-}$ mice with WT T cells rescued their functional capacity and the animals could run greater distances compared to mice lacking the CD4 subset (FIG. 4B; 91.11±3.83 vs 60.06±9.69, P=0.0032). Furthermore, Rag$^{-/-}$ mice repopulated with wild type CD4 T cells performed better than those repopulated with Rictor$^{-/-}$ CD4$^+$ T cells (72.31±7.40, P=0.0368), confirming the role of Th2 CD4$^+$ T cells in functional muscle regeneration. Differences in endurance between the Cd4$^{-/-}$ mice and T-Rictor$^{-/-}$ mice were not significant (P=0.3752).

Figure 15:
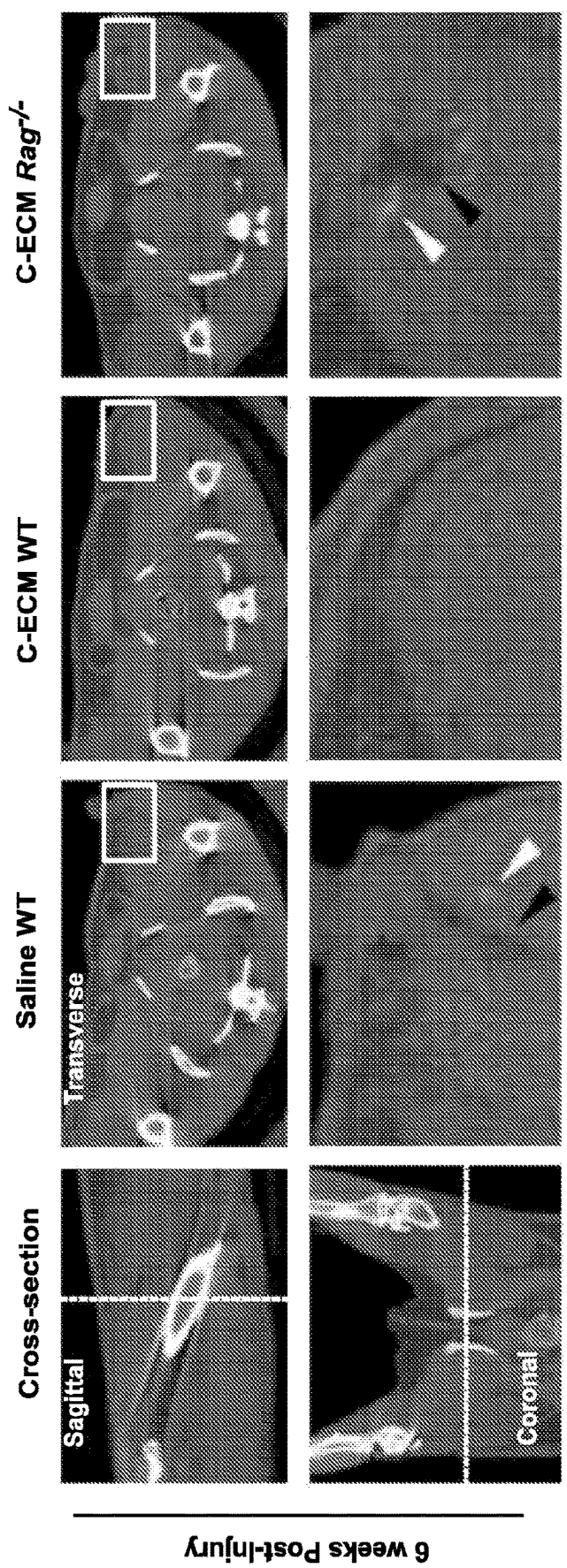
FIG. 15 depicts computed tomography images which reveal irregular muscle density in Rag$^{-/-}$ mice. CT imaging of mice at 6 week post-injury shows non-uniform muscle density in Saline treated and C-ECM treated Rag$^{-/-}$ mice, but uniform muscle in C-ECM treated WT mice.

Muscle structure correlated with the differences in functional capacity. Histologically at 6 weeks post-injury, the quadriceps muscle treated with cardiac-extra cellular matrix (C-ECM) scaffold appeared similar to that of healthy controls, with minimal scaffold visible and repair tissue fully integrated within the surrounding musculature. On the other hand, a large region of fibrous tissue with active inflammation was present in muscles treated with the collagen scaffold (FIG. 4C). In Rag$^{-/-}$ mice, there was a greater persistence of all scaffolds, most notably in the collagen-treated animals. Additionally, Rag$^{-/-}$ mice displayed increased adipose deposition compared to their wild type counterparts. The presence of scarring and inhomogeneous tissue in Rag$^{-/-}$ mice (and collagen-treated WT mice) was also visible with computed tomography (CT) imaging (FIG. 15).

In all cases, the Rag$^{-/-}$ mice had substantially greater levels of fibrosis and smaller diameter muscle fibers after 6 weeks (FIG. 4C). To further evaluate treatments during active remodeling and regeneration, the muscle was also characterized after 3 weeks post-injury. Centrally nucleated muscle fibers, which are indicative of active regeneration or recovery from injury, were present within the biomaterial scaffold and around the defect site (FIG. 4D, FIGS. 16A-16C). Notably, the size and morphology of these fibers depended on the presence of an adaptive immune system—wild type mice produced muscle with larger, more rounded fibers, whereas Rag$^{-/-}$ mice muscle contained smaller, irregularly shaped fibers, indicating a defect in muscle regeneration. The muscle in the Rag$^{-/-}$ mice also appeared to contain larger regions of fibrous and adipose tissue compared to WT mice in all groups, suggesting an imbalance in fibro-adipogenic tissue balance during muscle regeneration (FIG. 4D, FIGS. 16A-16C). In addition, the pathologic Rag$^{-/-}$ histo-morphology was recapitulated in Cd4$^{-/-}$ mice, confirming the role of CD4$^+$ T cells in fibro-adipogenic lineage commitment (FIG. 4D). Increased gene expression of Adipoq (adiponectin), a hormone exclusively produced by adipose tissue and involved in the regulation of fatty acid and glucose metabolism, confirmed ectopic adipogenesis in Rag$^{-/-}$ whole muscle. Similarly, the expression of Col1a1 (Type I Collagen) increased in Rag$^{-/-}$ mice muscle highlighting increased fibrosis (FIG. 4E; FIGS. 17A-17E). While scaffold treatment reduced fibro- and adipogenesis related markers in WT animals, this benefit was lost in Rag$^{-/-}$ mice, again demonstrating the importance of adaptive immunity in maintaining lineage fidelity in muscle regeneration.

Figure 4F:
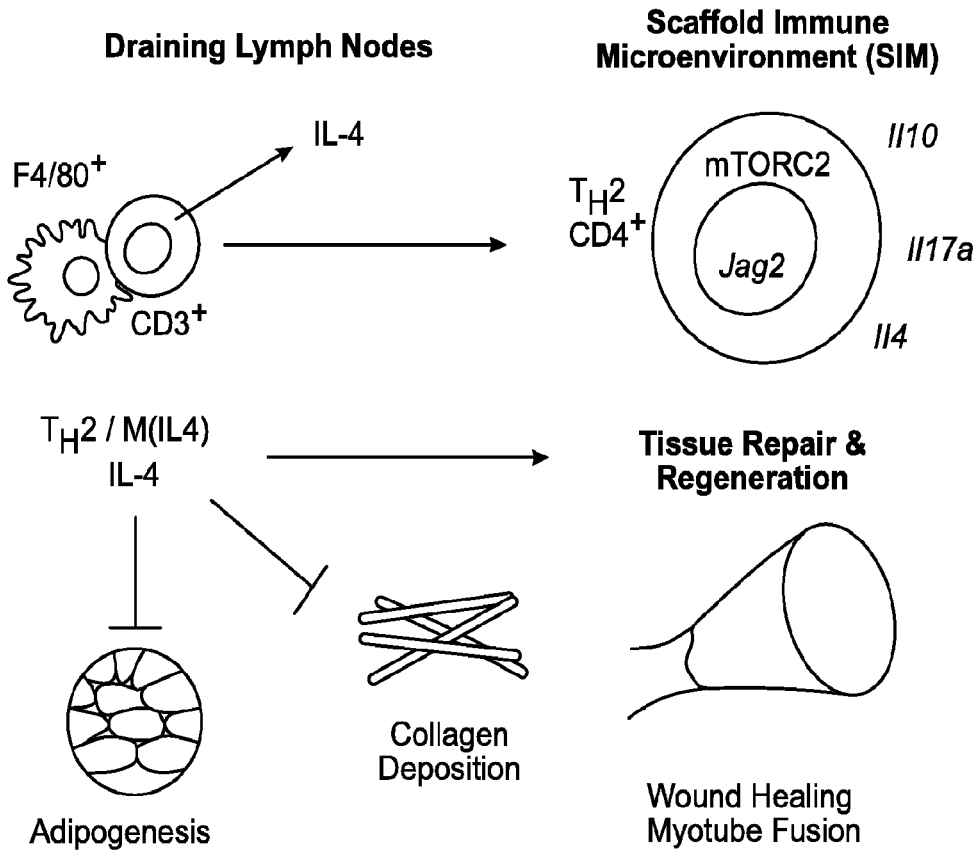

Thus, biomaterial scaffolds were discovered herein to have enhanced the development of a pro-regenerative immune environment and, for the first time, adaptive immune cells, specifically mTORC2-dependent CD4$^+$ Th2 T cells, have been implicated in the process of functional tissue restoration (FIG. 4F). The strong systemic Th2 polarization of the CD4 compartment was critical for M(IL-4) polarization of the myeloid compartment in the scaffolds, since their depletion dramatically reduced the M(IL-4) signature. Furthermore, the ectopic adipogenesis and enhanced fibrosis observed in regenerating muscle in Rag$^{-/-}$ mice emphasized the importance of adaptive immunity in maintaining lineage fidelity in the regenerating tissue.

Accordingly, the above studies have defined T cells and the mTORC2 pathway as new targets for immunomodulation with next-generation biomaterials to enhance their efficacy in controlling and balancing the immune microenvironment locally and systemically. Just as cancer research has made great strides in T cell therapies, these concepts can be translated to biomaterials design and strategies to improve tissue repair and regeneration (S. A. Rosenberg, et al. *Nature medicine* 10, 909-915 (2004), O. A. Ali et al. *Cancer research* 74, 1670-1681 (2014), J. Kim, et al. *Nano today* 6, 466-477 (2011), and O. A. Ali, et al. *Advanced functional materials* 23, 4621-4628 (2013)).

Materials and Methods

Tissue ECM Preparation

Porcine derived tissues (Wagner Meats, Mt. Airy Md.) were decellularized following a standard protocol. Samples were processed into a paste through the use of a knife-mill processor (Retsch, Germany) with particle sizes no larger than 5 mm$^2$, and rinsed thoroughly with running distilled water until blood was cleared from samples. Bone samples were pre-treated for decalcification by incubation in 10% formic acid (Sigma) for 3 days, which was verified by a colorimetric calcium test (STANBIO Laboratory). Tissues were then incubated in 3.0% peracetic acid (Sigma) on a shaker at 37° C. for 4 hours, with a change to fresh acid solution after 1 hour. The pH was adjusted to 7 with thorough water and PBS rinsing and pH was tested after solution was freshly changed and tissue rested for 20 minutes. Samples were washed once more with distilled water then transferred to a 1% Triton-X100 (Sigma)+2 mM sodium EDTA (Sigma) solution on a stir plate at 400 rpm, room temperature for 3 days, changing the solution daily. Tissues were rinsed thoroughly with distilled water until no bubbles formed from detergent upon agitation. Finally processed tissues were incubated in 600 U/ml DNase I (Roche Diagnostics)+10 mM MgCl$_2$ (J. T. Baker)+10% Antifungal-Antimycotic (Gibco®) for 24 hours. Tissues were rinsed thoroughly with distilled water, then frozen at −80° C. and lyophilized for 3 days. The dry sample was turned into a particulate form using SPEX SamplePrep Freezer/Mill (SPEX CertiPrep). ECM powder was stored between −20° C. and −80° C. and UV sterilized prior to use. Collagen from bovine tendon (Sigma) was cryomilled using the SPEX SamplePrep Freezer/Mill to form a particulate similar to the whole tissue ECM samples.

Volumetric Muscle Loss (VML) Surgery

Six to eight-week-old female wild type C57BL/6 (Charles River), B6.129S7-Rag1$^{tm1Mom}$/J, BALB/c-Il4ra$^{tm1Sz}$/J, or B6.129S2-Cd4$^{tm1Mak}$/J (Jackson Laboratories) female mice were anesthetized with 4.0% isoflurane and maintained under 2.5% isoflurane. Hair was removed from the lower extremities with an electric razor (Oster). After ethanol sterilization of the surrounding skin, a 1.5-cm incision was created between the knee and hip joint to access the quadriceps femoris muscle. Through the use of surgical scissors, a 3 mm 3 mm deep defect was created in the quadriceps femoris muscle group. The resulting bilateral defects were filled with 0.05 cc of a 250-350 mg/ml biomaterial scaffold (UV-sterilized ECM (manufactured in house) or Collagen (Sigma)) or 0.05 cc of a vehicle (saline) control. Mice were under anesthesia for 10-15 minutes during surgical preparation and procedure before return to cage and monitored until ambulatory. Directly after surgery, mice were given subcutaneous carprofen (Rimadyl®, Zoetis) at 5 mg/kg for pain relief and were maintained on Uniprim® antibiotic feed (275 ppm Trimethoprim and 1365 ppm Sulfadiazine, Harlan Laboratories) until the end of study to prevent opportunistic infections. After 1 (7 days), 3 (24 days) and 6 (42 days) weeks, the mice were sacrificed and their entire quadriceps femoris muscle was removed by cutting from the knee joint along the femur to the hip joint. Both inguinal and axillary/brachial lymph nodes and whole muscle samples for RNA isolation were flash frozen in liquid nitrogen and stored at −80° C. until RNA extraction. All animal procedures in this study were conducted in accordance with an approved Johns Hopkins University IACUC protocol.

T Cell Adoptive Transfer

CD4+ T cells were isolated from lymph nodes and spleens of wild type C57BL/6 and B6.Rictor$^{-/-}$ mice by crossing B6.Rictor$^{F/F}$ with B6.Cd4-cre) using MACS CD4+ T Cell Isolation Kit (Miltenyi Biotec) as per manufacturer's instructions. Purity was confirmed by staining with the following FACS antibody panel: CD3 AlexaFluor488, CD4 PE-Cy7, CD8 APC (Biolegend). 3 million CD4+ T cells were injected into B6.129S7-Rag1$^{tm1Mom}$/J. After 12 days post-injection, mice were tested for T cell presence and CD4/CD8 purity in peripheral blood to confirm repopulation. After 2 weeks, muscle surgery was performed as per previously described.

RT-PCR

In vivo inguinal and axillary/brachial lymph node samples from volumetric muscle loss (VML) studies were homogenized in TRIzol and RNA was extracted using a combination of TRIzol and RNeasy Mini (Qiagen) column-based isolations. cDNA was synthesized through the use of SuperScript Reverse Transcriptase III (Life Technologies) as per manufacturer's instructions. RT-PCR was conducted on an Applied Biosystems Real Time PCR Machine using SYBR Green (Life Technologies) as a reporter and the following primers: B2m forward CTC GGT GAC CCT GGT CTT TC (SEQ ID NO: 1), B2m reverse GGA TTT CAA TGT GAG GCG GG (SEQ ID NO: 2); Tnfa forward GTC CAT TCC TGA GTT CTG (SEQ ID NO: 3), Tnfa reverse GAA AGG TCT GAA GGT AGG (SEQ ID NO: 4); Il1β forward GTA TGG GCT GGA CTG TTT C (SEQ ID NO: 5), Il1β reverse GCT GTC TGC TCA TTC ACG (SEQ ID NO: 6); Retnla forward CTT TCC TGA GAT TCT GCC CCA G (SEQ ID NO: 7), Retnla reverse CAC AAG CAC ACC CAG TAG CA (SEQ ID NO: 8); Ifnγ forward TCA AGT GGC ATA GAT GTG GAA (SEQ ID NO: 9), Ifnγ reverse TGA GGT AGA AAG AGA TAA TCT GG (SEQ ID NO: 10); Il4 forward ACA GGA GAA GGG ACG CCA T (SEQ ID NO: 11), Il4 reverse ACC TTG GAA GCC CTA CAG A (SEQ ID NO: 12); Gata3 forward GAA GGC ATC CAG ACC CGA AAC (SEQ ID NO: 13), Gata3 reverse ACC CAT GGC GGT GAC CAT GC (SEQ ID NO: 14). Whole muscle samples were processed similarly to lymph nodes to isolate RNA and produce cDNA. Primers used included those previously described and: Arg1 forward CAG AAG AAT GGA AGA GTC AG (SEQ ID NO: 15), Arg1 reverse CAG ATA TGC AGG GAG TCA CC (SEQ ID NO: 16); Col1a1 forward CTG GCG GTT CAG GTC CAA T (SEQ ID NO: 17), Col1a1 reverse TTC CAG GCA ATC CAC GAG C (SEQ ID NO: 18); Fabp4 forward TCA CCT GGA AGA CAG CTC CT (SEQ ID NO: 19), Fabp4 reverse AAT CCC CAT TTA CGC TGA TG (SEQ ID NO: 20); AdipoQ forward TCC TGG AGA GAA GGG AGA GAA AG (SEQ ID NO: 21), AdipoQ reverse TCA GCT CCT GTC ATT CCA ACA T (SEQ ID NO: 22); Lep forward TTC ACA CAC GCA GTC GGT AT (SEQ ID NO: 23), Lep reverse ACA TTT TGG GAA GGC AGG CT (SEQ ID NO: 24); Actb forward ATG TGG ATC AGC AAG CAG GA (SEQ ID NO: 25), Actb reverse AAG GGT GTA AAA CGC AGC TCA (SEQ ID NO: 26) (Integrated DNA Technologies).

F4/80$^+$ and CD3$^+$ cells from volumetric muscle wounds were sorted directly into RNA lysis buffer; RLT buffer (Qiagen)+β-mercaptoethanol (Sigma). RNA was isolated using an RNeasy Micro Kit (Qiagen) with carrier RNA and on-column DNase treatment. cDNA synthesis was performed with a High Capacity cDNA Reverse Transcription Kit (Applied Biosystems). Isolated RNA underwent preamplification prior to plating in custom 96-well TaqMan® Array Fast Plates (Life Technologies) and gene expression was detected on an Applied Biosystems StepOne Real-Time PCR System.

Histology

Inguinal lymph nodes were harvested and fixed in formalin overnight before dehydration and paraffin embedding, microtome sectioning, then histological examination via hematoxylin and eosin staining. Muscle samples were prepared as fresh-frozen samples for cryosectioning by flash freezing in cold isopentane after mounting in Tragacanth gum (Sigma Life Sciences). A Microm HM 550 cryostat (Fisher Scientific) was used to obtain 10 μm cryosections from 5-7 different regions of each muscle roughly 300 μm apart. Sections were stained with a Hematoxylin and Eosin protocol (Sigma Aldrich) or with a Modified Masson's Trichrome protocol.

Flow Cytometry

Muscle wounds and surrounding area were harvested at 1 (7 days), 3 (24 days) and 6 (42 days) weeks post-surgery by cutting the quadriceps muscle from the hip to the knee and finely diced using a scalpel in 1×PBS. Resultant material was digested for 45 minutes at 37° C. in 1.67 Wünsch U/ml Liberase TL (Roche Diagnostics)+0.2 mg/ml DNase I (Roche Diagnostics) in serum-free RPMI-1640 medium (Gibco) on a shaker at 400 rpm. Digest was filtered through a 100 μm cell strainer (Fisher) then washed twice with 1×PBS. Cells were resuspended in 5 ml 1×PBS and layered atop 5 ml Lympholyte-M (Cedarlane), then spun for 20 minutes at 1200× g. Cellular interphase was washed twice with 1×PBS then transferred to a 96-well plate for antibody staining. Isolated cells were stained with the following antibody panel: LIVE/DEAD® Fixable Aqua Dead Cell Stain Kit (Life Technologies), CD19 BrilliantViolet 421 (BioLegend), CD3 AlexaFluor 488 (BioLegend), CD34 PerCP-Cy5.5 (BioLegend), CD11c APC-Cy7 (BD Biosciences), F4/80 PE-Cy7 (BioLegend), CD86 AlexaFluor700 (BioLegend), CD206 APC (BioLegend). After staining cells were fixed and analyzed On a BD LSR Analyszer (BD Biosciences). LIVE/DEAD® Fixable Aqua Dead Cell Stain negative (live) cells were evaluated based upon percent population of T cells (CD3+), B cells (CD19+), dendritic cells (CD11c+), and macrophages (F4/80+). Macrophages were further analyzed for polarization by mean fluorescence intensity of F4/80$^+$, CD11c$^+$ and F4/80+CD11c$^+$ cells in CD86 AlexaFluor700 and CD206 APC channels. All analyses were performed in FlowJo Flow Cytometry Analysis Software (Treestar). The T cell panel included LIVE/DEAD® Fixable Aqua Dead Cell Stain Kit (Life Technologies), CD3 AlexaFluor488 (BioLegend), CD4 PE-Cy7 (BioLegend), CD8 AlexaFluor 700 (BioLegend), FoxP3 Pacific Blue (BioLegend), IL4ra PE (BioLegend) and CCR5 APC (BioLegend). FoxP3 staining followed fixation and permeabilization with BD CytoFix/CytoPerm Kit (BD Biosciences). Myeloid compartment screening at 1 week was done with the following antibody panel: Fixable Viability Dye eFluor®780 (eBioscience), F4/80 PE-Cy7 (BioLegend), CD11b AlexaFluor700 (BioLegend), CD11c APC (BioLegend), Ly6C Per/CP-Cy5.5 (BioLegend), Ly6G PacificBlue (BioLegend), CD86 BrilliantViolet510 (BioLegend), CD206 PE (BioLegend), MHCII I-A/I-E AlexaFluor488 (BioLegend).

Samples prepared for sorting of F4/80$^+$ and CD3$^+$ cells followed the same isolation, then were stained with Fixable Viability Dye eFluor®780 (eBioscience), F4/80 PE-Cy7 (BioLegend), CD11c APC-Cy7 (BD Biosciences) and CD3 AlexaFluor488 (BioLegend). Samples were run on a BD FACS Aria and collected directly into RPE lysis buffer (Qiagen) containing β-mercaptoethanol (Sigma), and stored at −80° C. until RNA isolation.

Statistical Analysis

All samples are representative of n=4 mice. Data are displayed as mean±standard error of the mean. Statistical outliers were removed using Grubbs' outlier test at alpha=0.05 using GraphPad Prism v6 Software (GraphPad Software Inc., La Jolla, Calif.), this sample was not included in analysis of percent cell populations at 6 weeks. Two-way ANOVAs were performed (GraphPad Prismv6), with statistical significance designated at p<0.05. For multiple comparisons, Tukey or Dunnet post-test corrections were applied. For gene expression analyses of sorted CD3+, F4/80+WT, and F4/80+ Rag$^{-/-}$ cells, scatter plots, heat maps, and correlation matrices of gene expression levels were used to compare across different materials: Saline, Bone, Cardiac, Collagen. To distinguish which groups of genes were differentially expressed based on material vs. saline, a re-sampling based permutation test based on the maximum Wilcoxon Rank Sum statistic within the gene group was used. Individual gene expression was also compared across material and saline using the Wilcoxon Rank Sum test. Expression between F4/80 WT and Rag$^{-/-}$ was compared for each material using the Wilcoxon Rank Sum test. Additionally, the difference of each material and saline between F4/80 WT and Rag−/− was compared using linear regression models (material by Rag$^{-/-}$ status interaction). Due to the exploratory nature and the small sample size, adjustment for multiple comparisons was not considered. Statistical analyses were performed using the R statistical package (version 2.15.1). Power analysis was not conducted to determine sample size.

Rheology

Rheology was performed with an Ares G2 rheometer (TA Instruments New Castle, Del.). Experiments were conducted at physiological temperatures (37° C.) and performed in sequence. Sample was loaded in 400 mg (wet) amounts on the rheometer stage (25 mm geometry) and gap was set to 1.5 mm. The experimental design followed a frequency sweep from 0.1 rad/s to 15 rad/s, oscillation frequency (15 rad/s constant), creep test (0.5% strain) and axial force until failure (−1.5 mm delta length). 3 samples per group were tested under the same rheological protocol. Samples were kept hydrated during these rheology experiments with PBS.

Cell Culture

Murine immortalized bone marrow macrophages (iBMM, Michele de Palma, Ecole Polytechnique Federale Lausanne) were cultured as per developer's protocol in IMDM (Gibco®) media containing 20% FBS (Hyclone, GE Healthcare Life Sciences), 2.5 mM L-glutamine (Gibco®), 1% PenStrep (Life Technologies), and 50 ng/ml M-CSF (Recombinant Mouse, BioLegend). Polarization was compared to primary cells through the use of RT-PCR after 24 hours of polarization in conditioned media (M0, M1, or M2 media) and confirmed to be a reliable in vitro comparison to primary macrophages. iBMM macrophages were cultured on plates coated with ECM powder for 24 hours in growth medium, or medium supplemented with 200 ng/ml E. coli lipopolysaccharide (LPS 055:B5, Sigma) and 20 ng/ml interferon gamma (IFNγ, Peprotech) or 20 ng/ml interleukin-4 (IL-4, Peprotech), for M1 and M2 polarizations, respectively.

Flow Cytometry: In Vitro Screening

In vitro samples were harvested using Accutase (Life Technologies) and washed with cold 1×PBS. Then, cells were stained with the following antibody panel: F4/80 PE-Cy7 (BioLegend), CD11b Pacific Blue (BioLegend), CD11c APC-Cy7 (BD Biosciences), CD86 AlexaFluor700 (BioLegend), MHCII (I-A/I-E) AlexaFluor488 (BioLegend), CD206 APC (BioLegend) and LIVE/DEAD® Fixable Aqua Dead Cell Stain Kit (Life Technologies). Samples were fixed using the BD Cytofix/Cytoperm™ kit (BD Biosciences), and run on BD LSRII Cell Analyzer, data was analyzed using FlowJo Flow Cytometry Analysis Software (Treestar). M1/M2 polarization levels were determined by mean fluorescence intensity of CD86 and CD206 in LIVE/DEAD® Fixable Aqua Dead Cell Stain $^-$F4/80$^+$CD11c$^-$ cells.

Micro-CT Imaging

Imaging was conducted using the Sedecal SuperArgus 4R PET/CT system. 720 projection images over 360 degrees in 0.5 degree increments were acquired; the maximum resolution mode was used, which means each acquired projection image was magnified 5.5 times when compared with the object. The x-ray tube was set with 50 kVp and 100 µA. Exposure time for each projection was 350 ms. Projection images were stored in a matrix with dimensions 1536×972, with 0.15 mm pixel size. CT images were reconstructed using Cobra reconstruction software. Each CT image was stored in a matrix with size 1344×1344×864 with voxel size 0.031 mm. Each image in figure was contrast-enhanced to show defects, the same enhancements were applied for each image.

Treadmill Testing for Muscle Function 48 hours prior to testing mice were trained on treadmill apparatus running at 5 m/min and increased by 1 m/min every minute for a total of 5 minutes. Mice were run to exhaustion starting at 5 m/min and increased by 1 m/min every minute. Exhaustion was defined as when the mouse stayed on the pulsed shock grid for a continuous 30 seconds (Treat NMD: Brunelli et al 2007, Denti et al 2006). Animals were tested at least 48 hours prior to harvesting for analysis via FACS, PCR, or histology.

REFERENCES

1. T. A. Wynn, A. Chawla, and J. W. Pollard, Macrophage biology in development, homeostasis and disease. *Nature*, 496(7446):445-55. (2013).
2. J. A. Stefater, 3rd, et al., Metchnikoff's policemen: macrophages in development, homeostasis and regeneration. *Trends Mol Med*, 17(12):743-52. (2011).
3. J. A. Hubbell, Biomaterials in tissue engineering. *Biotechnology (N Y)*, 13(6):565-76. (1995).
4. P. Matzinger, Friendly and dangerous signals: is the tissue in control? *Nat Immunol*, 8(1):11-3. (2007).

5. P. Matzinger and T. Kamala, Tissue-based class control: the other side of tolerance. *Nat Rev Immunol*, 11(3):221-30. (2011).
6. Y. F. Peng, et al., Innate and Adaptive Immune Response to Apoptotic Cells. *J Autoimmun*, 29(4):303-9. (2007).
7. J. S. Otis, et al., Pro-inflammatory mediation of myoblast proliferation. *PLoS One*, 9(3):e92363. (2014).
8. S. Frantz, et al., Innate immunity and angiogenesis. *Circ Res*, 96(1):15-26. (2005).
9. S. Epelman, P. P. Liu, and D. L. Mann, Role of innate and adaptive immune mechanisms in cardiac injury and repair. *Nat Rev Immunol*, 15(2):117-29. (2015).
10. C. E. Lewis and J. W. Pollard, Distinct role of macrophages in different tumor microenvironments. *Cancer Res*, 66(2):605-12. (2006).
11. J. G. Tidball and S. A. Villalta, Regulatory interactions between muscle and the immune system during muscle regeneration. *Am J Physiol Regul Integr Comp Physiol*, 298(5):R1173-87. (2010).
12. V. Salmon-Ehr, et al., Implication of interleukin-4 in wound healing. *Lab Invest*, 80(8):1337-43. (2000).
13. J. E. Heredia, et al., Type 2 innate signals stimulate fibro/adipogenic progenitors to facilitate muscle regeneration. *Cell*, 153(2):376-88. (2013).
14. S. F. Badylak, et al., Macrophage phenotype as a determinant of biologic scaffold remodeling. *Tissue Eng Part A*, 14(11):1835-42. (2008).
15. A. J. Allman, et al., The Th2-restricted immune response to xenogeneic small intestinal submucosa does not influence systemic protective immunity to viral and bacterial pathogens. *Tissue Eng*, 8(1):53-62. (2002).
16. A. J. Allman, et al., Xenogeneic extracellular matrix grafts elicit a TH2-restricted immune response. *Transplantation*, 71(11):1631-40. (2001).
17. B. M. Sicari, et al., An acellular biologic scaffold promotes skeletal muscle formation in mice and humans with volumetric muscle loss. *Sci Transl Med*, 6(234): 234ra58. (2014).
18. D. Amsen, et al., Direct regulation of Gata3 expression determines the T helper differentiation potential of Notch. *Immunity*, 27(1):89-99. (2007).
19. T. C. Fang, et al., Notch directly regulates Gata3 expression during T helper 2 cell differentiation. *Immunity*, 27(1):100-10. (2007).
20. Y. Sun, et al., The anti-oxidative, anti-inflammatory, and protective effect of S100A8 in endotoxemic mice. *Mol Immunol*, 53(4):443-9. (2013).
21. M. E. Davis, et al., MMP inhibition as a potential method to augment the healing of skeletal muscle and tendon extracellular matrix. *J Appl Physiol* (1985), 115(6):884-91. (2013).
22. F. Mourkioti and N. Rosenthal, IGF-1, inflammation and stem cells: interactions during muscle regeneration. *Trends Immunol*, 26(10):535-42. (2005).
23. A. Musaro, et al., Localized Igf-1 transgene expression sustains hypertrophy and regeneration in senescent skeletal muscle. *Nat Genet*, 27(2):195-200. (2001).
24. J. P. Liu, et al., Mice carrying null mutations of the genes encoding insulin-like growth factor I (Igf-1) and type 1 IGF receptor (Igf1r). *Cell*, 75(1):59-72. (1993).
25. N. Arsic, et al., Vascular endothelial growth factor stimulates skeletal muscle regeneration in vivo. *Mol Ther*, 10(5):844-54. (2004).
26. J. Blackwell, et al., Changes in CEBPB expression in circulating leukocytes following eccentric elbow-flexion exercise. *J Physiol Sci*, 65(1):145-50. (2015).
27. D. Gosselin, et al., Environment drives selection and function of enhancers controlling tissue-specific macrophage identities. *Cell*, 159(6):1327-40. (2014).
28. Y. Lavin, et al., Tissue-resident macrophage enhancer landscapes are shaped by the local microenvironment. *Cell*, 159(6):1312-26. (2014).
29. S. J. Jenkins, et al., Local macrophage proliferation, rather than recruitment from the blood, is a signature of TH2 inflammation. *Science*, 332(6035):1284-8. (2011).
30. J. Kim and D. J. Mooney, In Vivo Modulation of Dendritic Cells by Engineered Materials: Towards New Cancer Vaccines. *Nano Today*, 6(5):466-77. (2011).
31. O. A. Ali, et al., Identification of immune factors regulating antitumor immunity using polymeric vaccines with multiple adjuvants. *Cancer Res*, 74(6):1670-81. (2014).
32. O. A. Ali, et al., Inflammatory cytokines presented from polymer matrices differentially generate and activate DCs in situ. *Adv Funct Mater*, 23(36):4621-8. (2013).
33. D. E. Discher, D. J. Mooney, and P. W. Zandstra, Growth factors, matrices, and forces combine and control stem cells. *Science*, 324(5935):1673-7. (2009).
34. A. J. Engler, et al., Matrix elasticity directs stem cell lineage specification. *Cell*, 126(4):677-89. (2006).
35. B. N. Brown, et al., Macrophage polarization: an opportunity for improved outcomes in biomaterials and regenerative medicine. *Biomaterials*, 33(15):3792-802. (2012).
36. B. N. Brown, B. M. Sicari, and S. F. Badylak, Rethinking regenerative medicine: a macrophage-centered approach. *Front Immunol*, 5:510. (2014).
37. D. M. Faulk, et al., ECM hydrogel coating mitigates the chronic inflammatory response to polypropylene mesh. *Biomaterials*, 35(30):8585-95. (2014).
38. M. T. Wolf, et al., Polypropylene surgical mesh coated with extracellular matrix mitigates the host foreign body response. *J Biomed Mater Res A*, 102(1):234-46. (2014).
39. W. C. Gause, T. A. Wynn, and J. E. Allen, Type 2 immunity and wound healing: evolutionary refinement of adaptive immunity by helminths. *Nat Rev Immunol*, 13(8):607-14. (2013).
40. B. Gaudilliere, et al., Clinical recovery from surgery correlates with single-cell immune signatures. *Sci Transl Med*, 6(255):255ra131. (2014).
41. S. Reinke, et al., Terminally differentiated CD8(+) T cells negatively affect bone regeneration in humans. *Sci Transl Med*, 5(177):177ra36. (2013).
42. J. W. Godwin, A. R. Pinto, and N. A. Rosenthal, Macrophages are required for adult salamander limb regeneration. *Proc Natl Acad Sci USA*, 110(23):9415-20. (2013).
43. D. Ruffell, et al., A CREB-C/EBPbeta cascade induces M2 macrophage-specific gene expression and promotes muscle injury repair. *Proc Natl Acad Sci USA*, 106(41): 17475-80. (2009).
44. G. Rigotti, et al., Clinical treatment of radiotherapy tissue damage by lipoaspirate transplant: a healing process mediated by adipose-derived adult stem cells. *Plast Reconstr Surg*, 119(5):1409-22; discussion 1423-4. (2007).
45. M. Nambu, et al., Accelerated wound healing in healing-impaired db/db mice by autologous adipose tissue-derived stromal cells combined with atelocollagen matrix. *Ann Plast Surg*, 62(3):317-21. (2009).
46. M. Klinger, et al., Fat injection for cases of severe burn outcomes: a new perspective of scar remodeling and reduction. *Aesthetic Plast Surg*, 32(3):465-9. (2008).

47. C. M. Cowan, et al., Adipose-derived adult stromal cells heal critical-size mouse calvarial defects. *Nat Biotechnol*, 22(5):560-7. (2004).
48. V. Horsley, et al., IL-4 acts as a myoblast recruitment factor during mammalian muscle growth. *Cell*, 113(4): 483-94. (2003).
49. S. A. Rosenberg, J. C. Yang, and N. P. Restifo, Cancer immunotherapy: moving beyond current vaccines. *Nat Med*, 10(9):909-15. (2004).
50. D. J. Irvine, et al., Synthetic Nanoparticles for Vaccines and Immunotherapy. *Chem Rev*. (2015).
51. N. K. Mehta, K. D. Moynihan, and D. J. Irvine, Engineering New Approaches to Cancer Vaccines. *Cancer Immunol Res*. (2015).
52. J. M. Anderson *Annual Review of Materials Research* 31, 81-110 (2001).
53. J. M. Anderson and K. M. *Biomaterials* 5, 5-10 (1984).
54. J. M. Anderson *ASAIO Journal* 34, 101-107 (1988).
55. V. J. Mase, Jr. et al. *Orthopedics* 33, 511 (2010).
56. B. N. Brown et al. *Acta biomaterialia* 8, 978-987 (2012).
57. B. M. Sicari et al. *Tissue engineering. Part A* 18, 1941-1948 (2012).
58. V. Z. Beachley et al. *Nat Meth advance online publication*, (2015).
29. P. J. Murray et al. *Immunity* 41, 14-20 (2014).
60. G. M. Delgoffe et al. *Nature immunology* 12, 295-303 (2011).

What is claimed is:

1. A method for treating a wound in a subject, the method comprising:
   administering to the subject an effective amount of a composition consisting of a collagen scaffold and interleukin-4 (IL-4);
   and wherein the interleukin-4 (IL-4) induces a pro-regenerative type-2 response, thereby treating the wound.

2. The method of claim 1, wherein the interleukin-4 (IL-4) induces an adaptive immune system response.

3. The method of claim 1, wherein a rate of wound healing is increased by 2%, 4%, 6%, 8%, or 10%.

4. The method of claim 1, wherein the scaffold is impregnated with the interleukin-4 (IL-4).

5. The method of claim 1, wherein the wound is an acute wound, a chronic wound, or a surgical wound.

6. A pharmaceutical composition, the composition consisting of:
   an effective amount of interleukin-4 (IL-4) and a collagen scaffold.

7. A method for promoting wound healing or tissue regeneration in a subject, the method comprising:
   administering to said subject an effective amount of a composition consisting of 1) a collagen scaffold and 2) interleukin-4 (IL-4);
   wherein the interleukin-4 (IL-4) induces a pro-regenerative type-2 response, thereby increasing the rate of at which the wound heals or the tissue regenerates.

8. The method or composition of claim 1, wherein the wound is selected from the group consisting of a skin wound, a muscle wound, a cartilage wound, and a nervous system wound.

* * * * *

```
                            SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: B2m forward primer

<400> SEQUENCE: 1
ctcggtgacc ctggtctttc                                                    20

<210> SEQ ID NO 2
<211> LENGTH: 20
<212> TYPE: DNA
<213> ORGANISM: Artificial Sequence
<220> FEATURE:
<223> OTHER INFORMATION: B2m reverse primer

<400> SEQUENCE: 2
ggatttcaat gtgaggcggg                                                    20

<210> SEQ ID NO 3
<211> LENGTH: 18
<212> TYPE: DNA
<213> ORGANISM: Artificial Sequence
<220> FEATURE:
<223> OTHER INFORMATION: Tnfalpha forward primer

<400> SEQUENCE: 3
gtccattcct gagttctg                                                      18

<210> SEQ ID NO 4
<211> LENGTH: 18
<212> TYPE: DNA
<213> ORGANISM: Artificial Sequence
<220> FEATURE:
<223> OTHER INFORMATION: Tnfalpha reverse primer

<400> SEQUENCE: 4
gaaaggtctg aaggtagg                                                      18

<210> SEQ ID NO 5
<211> LENGTH: 19
<212> TYPE: DNA
<213> ORGANISM: Artificial Sequence
<220> FEATURE:
<223> OTHER INFORMATION: IL1beta forward primer

<400> SEQUENCE: 5
gtatgggctg gactgtttc                                                     19
```

<210> SEQ ID NO 6
<211> LENGTH: 18
<212> TYPE: DNA
<213> ORGANISM: Artificial Sequence
<220> FEATURE:
<223> OTHER INFORMATION: IL1beta reverse primer

<400> SEQUENCE: 6
gctgtctgct cattcacg                                              18

<210> SEQ ID NO 7
<211> LENGTH: 22
<212> TYPE: DNA
<213> ORGANISM: Artificial Sequence
<220> FEATURE:
<223> OTHER INFORMATION: Retnla forward primer

<400> SEQUENCE: 7
ctttcctgag attctgcccc ag                                         22

<210> SEQ ID NO 8
<211> LENGTH: 20
<212> TYPE: DNA
<213> ORGANISM: Artificial Sequence
<220> FEATURE:
<223> OTHER INFORMATION: Retnla reverse primer

<400> SEQUENCE: 8
cacaagcaca cccagtagca                                            20

<210> SEQ ID NO 9
<211> LENGTH: 21
<212> TYPE: DNA
<213> ORGANISM: Artificial Sequence
<220> FEATURE:
<223> OTHER INFORMATION: Ifngamma forward

<400> SEQUENCE: 9
tcaagtggca tagatgtgga a                                          21

<210> SEQ ID NO 10
<211> LENGTH: 23
<212> TYPE: DNA
<213> ORGANISM: Artificial Sequence
<220> FEATURE:
<223> OTHER INFORMATION: Ifngamma reverse primer

<400> SEQUENCE: 10
tgaggtagaa agagataatc tgg                                        23

<210> SEQ ID NO 11
<211> LENGTH: 19
<212> TYPE: DNA
<213> ORGANISM: Artificial Sequence
<220> FEATURE:
<223> OTHER INFORMATION: IL4 forward primer

<400> SEQUENCE: 11
acaggagaag ggacgccat                                             19

<210> SEQ ID NO 12
<211> LENGTH: 19
<212> TYPE: DNA
<213> ORGANISM: Artificial Sequence
<220> FEATURE:

<223> OTHER INFORMATION: IL4 reverse primer

<400> SEQUENCE: 12
accttggaag ccctacaga                                                19

<210> SEQ ID NO 13
<211> LENGTH: 21
<212> TYPE: DNA
<213> ORGANISM: Artificial Sequence
<220> FEATURE:
<223> OTHER INFORMATION: Gata3 forward primer

<400> SEQUENCE: 13
gaaggcatcc agacccgaaa c                                             21

<210> SEQ ID NO 14
<211> LENGTH: 20
<212> TYPE: DNA
<213> ORGANISM: Artificial Sequence
<220> FEATURE:
<223> OTHER INFORMATION: Gata3 reverse primer

<400> SEQUENCE: 14
acccatggcg gtgaccatgc                                               20

<210> SEQ ID NO 15
<211> LENGTH: 20
<212> TYPE: DNA
<213> ORGANISM: Artificial Sequence
<220> FEATURE:
<223> OTHER INFORMATION: Arg1 forward primer

<400> SEQUENCE: 15
cagaagaatg gaagagtcag                                               20

<210> SEQ ID NO 16
<211> LENGTH: 20
<212> TYPE: DNA
<213> ORGANISM: Artificial Sequence
<220> FEATURE:
<223> OTHER INFORMATION: Arg1 reverse primer

<400> SEQUENCE: 16
cagatatgca gggagtcacc                                               20

<210> SEQ ID NO 17
<211> LENGTH: 19
<212> TYPE: DNA
<213> ORGANISM: Artificial Sequence
<220> FEATURE:
<223> OTHER INFORMATION: Col1a1 forward primer

<400> SEQUENCE: 17
ctggcggttc aggtccaat                                                19

<210> SEQ ID NO 18
<211> LENGTH: 19
<212> TYPE: DNA
<213> ORGANISM: Artificial Sequence
<220> FEATURE:
<223> OTHER INFORMATION: Col1a1 reverse primer

<400> SEQUENCE: 18
ttccaggcaa tccacgagc                                                19

```
<210> SEQ ID NO 19
<211> LENGTH: 20
<212> TYPE: DNA
<213> ORGANISM: Artificial Sequence
<220> FEATURE:
<223> OTHER INFORMATION: Fabp4 forward primer

<400> SEQUENCE: 19
tcacctggaa gacagctcct                                               20

<210> SEQ ID NO 20
<211> LENGTH: 20
<212> TYPE: DNA
<213> ORGANISM: Artificial Sequence
<220> FEATURE:
<223> OTHER INFORMATION: Fabp4 reverse primer

<400> SEQUENCE: 20
aatccccatt tacgctgatg                                               20

<210> SEQ ID NO 21
<211> LENGTH: 23
<212> TYPE: DNA
<213> ORGANISM: Artificial Sequence
<220> FEATURE:
<223> OTHER INFORMATION: AdipoQ forward primer

<400> SEQUENCE: 21
tcctggagag aagggagaga aag                                           23

<210> SEQ ID NO 22
<211> LENGTH: 22
<212> TYPE: DNA
<213> ORGANISM: Artificial Sequence
<220> FEATURE:
<223> OTHER INFORMATION: AdipoQ reverse primer

<400> SEQUENCE: 22
tcagctcctg tcattccaac at                                            22

<210> SEQ ID NO 23
<211> LENGTH: 20
<212> TYPE: DNA
<213> ORGANISM: Artificial Sequence
<220> FEATURE:
<223> OTHER INFORMATION: Lep forward primer

<400> SEQUENCE: 23
ttcacacacg cagtcggtat                                               20

<210> SEQ ID NO 24
<211> LENGTH: 20
<212> TYPE: DNA
<213> ORGANISM: Artificial Sequence
<220> FEATURE:
<223> OTHER INFORMATION: Lep reverse primer

<400> SEQUENCE: 24
acattttggg aaggcaggct                                               20

<210> SEQ ID NO 25
<211> LENGTH: 20
<212> TYPE: DNA
<213> ORGANISM: Artificial Sequence
<220> FEATURE:
<223> OTHER INFORMATION: Actb forward primer
```

```
<400> SEQUENCE: 25
atgtggatca gcaagcagga                                          20

<210> SEQ ID NO 26
<211> LENGTH: 21
<212> TYPE: DNA
<213> ORGANISM: Artificial Sequence
<220> FEATURE:
<223> OTHER INFORMATION: Actb reverse primer

<400> SEQUENCE: 26
aagggtgtaa aacgcagctc a                                        21
```